US 11,014,918 B2

(12) United States Patent
Tazi et al.

(10) Patent No.: US 11,014,918 B2
(45) Date of Patent: *May 25, 2021

(54) COMPOUNDS AND PHARMACEUTICAL COMPOSITIONS CONTAINING AT LEAST ONE OF THE COMPOUNDS

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Jamal Tazi, Clapiers (FR); Florence Mahuteau, Saint Remy les Chevreuses (FR); Romain Najman, L'Hay-les-Roses (FR); Didier Scherrer, Castelnau le lez (FR); Julien Santo, Montpellier (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/787,471

(22) Filed: Feb. 11, 2020

(65) Prior Publication Data
US 2020/0172525 A1 Jun. 4, 2020

Related U.S. Application Data

(60) Continuation of application No. 16/050,551, filed on Jul. 31, 2018, now Pat. No. 10,683,284, which is a division of application No. 15/486,836, filed on Apr. 13, 2017, now Pat. No. 10,253,020, which is a continuation-in-part of application No. 14/789,149, filed on Jul. 1, 2015, now Pat. No. 9,637,475, which is a continuation of application No. 14/087,762, filed on Nov. 22, 2013, now Pat. No. 9,108,919, which is a continuation of application No. 13/377,745, filed as application No. PCT/IB2010/052650 on Jun. 14, 2010, now abandoned, said application No. 15/486,836 is a continuation-in-part of application No. 14/789,250, filed on Jul. 1, 2015, now Pat. No. 10,017,498, which is a continuation of application No. 13/377,760, filed as application No.
(Continued)

(30) Foreign Application Priority Data

Jun. 12, 2009 (EP) .................................... 09162630
Jun. 12, 2009 (EP) .................................... 09305540

(51) Int. Cl.
| | | |
|---|---|---|
| C07D 413/04 | (2006.01) |
| C07D 215/38 | (2006.01) |
| C07D 241/44 | (2006.01) |
| C07D 401/12 | (2006.01) |
| C07D 403/12 | (2006.01) |
| C07D 217/02 | (2006.01) |
| A61K 31/4709 | (2006.01) |
| A61K 31/4985 | (2006.01) |
| C07D 213/74 | (2006.01) |
| C07D 215/42 | (2006.01) |
| C07D 215/46 | (2006.01) |

(52) U.S. Cl.
CPC ........ *C07D 413/04* (2013.01); *A61K 31/4709* (2013.01); *A61K 31/4985* (2013.01); *C07D 213/74* (2013.01); *C07D 215/38* (2013.01); *C07D 215/42* (2013.01); *C07D 215/46* (2013.01); *C07D 217/02* (2013.01); *C07D 241/44* (2013.01); *C07D 401/12* (2013.01); *C07D 403/12* (2013.01)

(58) Field of Classification Search
None
See application file for complete search history.

(56) References Cited

U.S. PATENT DOCUMENTS 2,605,182 A 7/1952 Peterson
4,738,710 A * 4/1988 Serban .................. A01N 43/42
504/247

(Continued)

FOREIGN PATENT DOCUMENTS

DE 958 647 C 2/1957
EP 0 394 112 A2 10/1990
(Continued)

OTHER PUBLICATIONS

Solekhova et al., Russian Journal of Organic Chemistry (Translation of Zhurnal Organicheskoi Khimii), 38(8), pp. 1192-1194 (Year: 2002).*

(Continued)

*Primary Examiner* — Zinna Northington Davis
(74) *Attorney, Agent, or Firm* — Oliff PLC

(57) ABSTRACT

The present disclosure is generally directed to the manufacture and use of compounds described herein for preventing, inhibiting or treating cancer, AIDS and/or premature aging, or the manufacture and use of a pharmaceutical composition comprising at least one of the compounds, or a pharmaceutically acceptable salt thereof, and a pharmaceutically acceptable carrier for preventing, inhibiting or treating cancer, AIDS and/or premature aging.

10 Claims, 2 Drawing Sheets

Specification includes a Sequence Listing.

Related U.S. Application Data

PCT/IB2010/052651 on Jun. 14, 2010, now Pat. No. 9,145,367, said application No. 15/486,836 is a continuation-in-part of application No. 14/256,334, filed on Apr. 18, 2014, now Pat. No. 9,908,869, which is a continuation of application No. 13/377,760, filed as application No. PCT/IB2010/052651 on Jun. 14, 2010, now Pat. No. 9,145,367, said application No. 15/486,836 is a continuation-in-part of application No. 13/377,753, filed as application No. PCT/IB2010/052652 on Jun. 14, 2010, now abandoned.

(60) Provisional application No. 61/186,552, filed on Jun. 12, 2009, provisional application No. 61/186,544, filed on Jun. 12, 2009.

(56) References Cited

U.S. PATENT DOCUMENTS

| | | |
|---|---|---|
| 6,180,632 B1 | 1/2001 | Myers et al. |
| 7,019,147 B1 | 3/2006 | Barth et al. |
| 9,061,999 B2 | 6/2015 | Tazi et al. |
| 9,108,919 B2 | 8/2015 | Roux et al. |
| 9,145,367 B2 | 9/2015 | Tazi et al. |
| 9,637,475 B2 | 5/2017 | Roux et al. |
| 10,017,498 B2 | 7/2018 | Tazi et al. |
| 10,253,020 B2 | 4/2019 | Tazi et al. |
| 10,435,370 B2 | 10/2019 | Tazi et al. |
| 10,683,284 B2 * | 6/2020 | Tazi ................. A61K 31/4709 |
| 2003/0207886 A1 | 11/2003 | Plucker et al. |
| 2004/0038969 A1 | 2/2004 | Doherty et al. |
| 2005/0085482 A1 | 4/2005 | Ramurthy et al. |
| 2005/0119225 A1 | 6/2005 | Schumacher et al. |
| 2006/0089380 A1 | 4/2006 | Barnham et al. |
| 2008/0161353 A1 | 7/2008 | Barnham et al. |
| 2008/0318984 A1 | 12/2008 | Verkman et al. |
| 2011/0003843 A1 | 1/2011 | Lejeune et al. |

FOREIGN PATENT DOCUMENTS

| | | |
|---|---|---|
| EP | 1 897 914 A1 | 3/2008 |
| EP | 2 075 309 A2 | 7/2009 |
| EP | 2 266 972 A1 | 12/2010 |
| EP | 2 465 502 A1 | 6/2012 |
| EP | 2 757 161 A1 | 7/2014 |
| FR | 2 387 229 A1 | 11/1978 |
| FR | 2 436 786 A1 | 4/1980 |
| FR | 2 627 493 A1 | 8/1989 |
| FR | 2 645 861 A1 | 10/1990 |
| FR | 2 849 474 A3 | 7/2004 |
| FR | 2 859 474 A1 | 3/2005 |
| FR | 2 859 475 A1 | 3/2005 |
| GB | 585362 A | 2/1947 |
| JP | H09-508642 A | 9/1997 |
| JP | 2005-507365 A | 3/2005 |
| JP | 2006-504646 A | 2/2006 |
| JP | 2006-519846 A | 8/2006 |
| JP | 2008-519814 A | 6/2008 |
| JP | 2009-174368 A | 8/2009 |
| JP | 6378802 B2 | 8/2018 |
| WO | 95/21613 A1 | 8/1995 |
| WO | 00/59875 A2 | 10/2000 |
| WO | 2002/074726 A2 | 9/2002 |
| WO | 2004/007461 A1 | 1/2004 |
| WO | 2004/078731 A1 | 9/2004 |
| WO | 2004/080463 A1 | 9/2004 |
| WO | 2005/023255 A2 | 3/2005 |
| WO | 2005/051302 A2 | 6/2005 |
| WO | 2006/051311 A1 | 5/2006 |
| WO | 2006/081444 A2 | 8/2006 |
| WO | 2007/000876 A1 | 1/2007 |
| WO | 2007/147217 A1 | 12/2007 |
| WO | 2008/003864 A1 | 1/2008 |
| WO | 2008/008234 A1 | 1/2008 |
| WO | 2008/089459 A1 | 7/2008 |
| WO | 2008/101935 A2 | 8/2008 |
| WO | 2008/115870 A2 | 9/2008 |
| WO | 2008/143440 A1 | 11/2008 |
| WO | 2009/021696 A1 | 2/2009 |
| WO | 2009/023844 A2 | 2/2009 |
| WO | 2009/029617 A1 | 3/2009 |
| WO | 2009/087238 A2 | 7/2009 |
| WO | 2010/143168 A2 | 12/2010 |
| WO | 2010/143169 A2 | 12/2010 |
| WO | 2010/143170 A2 | 12/2010 |
| WO | 2010/151755 A2 | 12/2010 |
| WO | 2012/080953 A1 | 6/2012 |
| WO | 2014/055944 A1 | 4/2014 |

OTHER PUBLICATIONS

Jun. 10, 2015 Notice of Allowance issued in U.S. Appl. No. 13/377,760.
Jul. 18, 2014 Office Action issued in U.S. Appl. No. 13/377,760.
Nov. 21, 2013 Office Action issued in U.S. Appl. No. 13/377,760.
Jun. 27, 2014 Office Action issued in U.S. Appl. No. 13/993,990.
Mar. 25, 2016 Office Action issued in U.S. Appl. No. 14/256,334.
Aug. 3, 2016 Office Action issued in U.S. Appl. No. 14/256,334.
Aug. 24, 2016 Office Action issued in U.S. Appl. 14/789,250.
Oct. 3, 2016 Office Action issued in U.S. Appl. No. 13/377,753.
Sep. 27, 2016 Office Action issued in Chinese Application No. 201510023109.1.
CAS Registry No. 330663-16-6 added on STN on Apr. 10, 2001.
Jul. 15, 2016 Office Action issued in Japanese Application No. 2015-120567.
Jun. 21, 2016 Office Action issued in U.S. Appl. No. 14/789,149.
Oct. 27, 2014 Office Action issued in U.S. Appl. No. 13/993,990.
Molina et al., "C=C-Conjugated Carbodiimides as 2-Azadienes in Intramolecular [4+2] Cycloadditions. One-Pot Preparation of Quinoline, alpha-Cabroline, and Quinindoline Derivatives," J. Org. Chem., 1992, vol. 57, pp. 929-939.
Desai et al., "Some Quinoline, Quinazoline and Pyrazine Derivatives as Antitubercular-Antibacterial Agents," Asian Journal of Chemistry, vol. 10, No. 4 (1998), pp. 993-994.
Desai et al., "2-Methyl-4-quinoline-hydrazide Derivatives as Antitubercular/Antibacterial Agents—Part I," Asian Journal of Chemistry, vol. 10, No. 2, (1998), pp. 370-372.
Katoh et al. "Isolation of the intermediates and improved synthesis of pyrido[1',2':1 ,2]imidazo[4, 5b]pyrazines and -quinoxalines", Heterocycles, 1992, 34(10), p. 1965-1972.
Carter et al., "Quinoxalines and related compounds-X-1", Tetrahedron, 34(7), p. 981-988, 1978.
Lombardino. "Some 3-Arylaminoquinoxaline-2-carboxylic Acids", Journal of Medicinal Chemistry, 9(5), p. 770-771, 1996.
CAS Registry No. 1004363-48-7 added on STN on Feb. 19, 2008.
CAS Registry No. 438481-24-4 added on STN on Jul. 12, 2002.
CAS Registry No. 933238-11-0 added on STN on Apr. 29, 2007.
CAS Registry No. 1011408-51-7 added on STN on Apr. 1, 2008.
CAS Registry No. 1135230-99-7 added on STN on Apr. 16, 2009.
CAS Registry No. 374598-11-5 added on STN on Dec. 10, 2001.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Dec. 5, 2016 Office Action issued in U.S. Appl. No. 14/256,334.
Nov. 16, 2016 Office Action in Japanese Patent Application No. 2016-006102.
Nov. 17, 2016 Office Action in Japanese Patent Application No. 2016-006104.
Nov. 17, 2016 Office Action issued in Japanese Patent Application No. 2016-006105.
Jan. 31, 2017 Office Action Issued in U.S. Appl. No. 14/902,935.
Hernandez-Lopez et al., "Alternative splicing in human tumour viruses: a therapeutic target?" Biochemical Journal, 2012, Biochemical Society, vol. 445, pp. 145-156.
Edwards et al., "Orf-I amd Orf-II—Encoded Proteins in HTLV-1 Infection and Persistence", Viruses, 2011, MDPI, vol. 3, pp. 861-885.

(56) References Cited

OTHER PUBLICATIONS

Bisset et. al., "Combined effect of zidovudine (ZDV), lamivudine (3TC) and abacavir (ABC) antiretoviral therapy in suppressing in vitro FIV replication," Antiviral Research, 2002, Elsevier, vol. 53 pp. 35-45.
Powell et. al., "Expression, characterisation and mutagensis of the aspartic proteinase from equine infections anaemia virus," European Journal of Biochemistry, 1996, FEBS, vol. 241, pp. 664-674.
U.S. Appl. No. 14/087,762, filed Nov. 22, 2013 in the name of Roux et al.
U.S. Appl. No. 14/256,334, filed Apr. 18, 2014 in the name of Tazi et al.
U.S. Appl. No. 14/789,250, filed Jul. 1, 2015 in the name of Tazi et al.
U.S. Appl. No. 14/789,149, filed Jul. 1, 2015 in the name of Roux et al.
U.S. Appl. No. 14/902,935, filed Jan. 5, 2016 in the name of Tazi et al.
U.S. Appl. No. 15/326,698, filed Jan. 17, 2017 in the name of Tazi et al.
Jan. 17, 2017 International Preliminary Report on Patentability issued in International Patent Application No. PCT/EP2015/066462.
Sep. 22, 2015 International Search Report issued in International Patent Application No. PCT/EP2015/066462.
Apr. 6, 2017 Office Action Issued in U.S. Appl. No. 13/377,753.
Ex Parte Gerard Marguierie and Eric Malaud, PTAB 2016, Appeal 2013-004606 issued in U.S. Appl. No. 10/587,697.
Jun. 27, 2017 Office Action issued in U.S. Appl. No. 14/789,250.
May 5, 2017 Office Action issued in Chinese Application No. 201510023124.6.
Oct. 3, 2017 Office Action issued in U.S. Appl. No. 14/789,250.
Nov. 6, 2017 Office Action issued in U.S. Appl. No. 15/326,698.
File Registry on STN, 408510-56-5, entered on Apr. 29, 2002.
CAS (Chemical Abstracts Service) Registry No. 92873-44-4, American Chemical Society, added on STN on Dec. 7, 1984, 1 page.
Gordon et al., "Hutchinson-Gilford Progeria Syndrome," NCBI Bookshelf, 2003, accessed Http://www.ncbi.nlm.gov/books/NBK1121/ on Jan. 26, 2016,21 pages.
Feb. 16, 2016 Office Action Issued in U.S. Appl. No. 13/377,753.
Loriga et al. "Quinoxaline Chemistry. Part 8. 2-[Anilino]-3-[Carboxy]-6(7)-Substituted Quinoxalines as Non Classical Antifolate Agents. Synthesis and Evaluation of Invitro Anticancer, Anti-HIV and Antifungal Activity". Farmaco, vol. 52, pp. 531-37, 1997.
CAPLUS Record for Loriga et al., "Part 8." (Retrieved Nov. 2013).
Loriga et al. "Quinoxaline Chemistry. Part 7. 2-[Aminobenzoates]- and 2-[Aminobenzoylglutamate]-Quinoxalines as Classical Antifolate Agents. Synthesis and Evaluation of In Vitro Anticancer, Anti-HIV and Antifungal Activity." Farmaco, vol. 52, pp. 157-166, (PubMed Abstract No. 9212450), 1997.
CAPLUS Record for Loriga et al., "Part 7." (Retrieved Nov. 2013).
Boganyi et al.,"Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.
Loones et al. "Synthesis of Pyrido[2, 1:2,3]Imidazo[4,5-B]Quinoline and Pyrido[1,2:1,2]Imidazo[4,5-B]Quinoline and Their Benzo and Aza Analogs via Tandem Catalysis". Tetrahedron, vol. 63, pp. 3954-3961, 2007.
Perry et al. "AIDS dementia: a review of the literature". Alzheimer Dis. Assoc. Disord 1, pp. 221-235, (PubMed Abstract 3331119), 1987.
Pauwels. "Aspects of Successful Drug Discovery and Development". Antiviral Res. vol. 71, pp. 77-89, 2006.
Respess et al., "Evaluation of an Ultrasensitive p24 Antigen Assay as a Potential Alternative to Human Immunodeficiency Virus Type 1 RNA Viral Load Assay in Resource-Limited Settings," Journal of Clinical Microbiology, vol. 43, No. 1, pp. 506-508, 2005.
Jun. 27, 2011 International Search Report issued in International Patent Application No. PCT/IB2010/052652.
Jun. 27, 2011 Written Opinion of the International Searching Authority issued in International Patent Application No. PCT/IB2010/052652.
Aug. 9, 2011 International Search Report issued in International Patent Application No. PCT/IB2010/052651.
Aug. 9, 2011 Written Opinion of the International Searching Authority issued in International Patent Application No. PCT/IB2010/052651.
Apr. 13, 2011 International Search Report issued in International Patent Application No. PCT/IB2010/052650.
Apr. 13, 2011 Written Opinion of the International Searching Authority issued in International Patent Application No. PCT/IB2010/052650.
Dec. 10, 2009 Partial European Search Report issued in European Patent Application No. 09162630.9.
Nov. 19, 2009 European Search Report issued in European Patent Application No. 09305540.
Vulliamy et al., "Mutations in the Telomerase Component NHP2 Cause the Premature Ageing Syndrome Dyskeratosis Congenita," PNAS, 2008, vol. 105, No. 23, pp. 8073-8078.
Brune et al., "Progeria: A New Kind of Laminopathy—Clinical and Molecular Update of the Hutchinson-Gilford Syndrome," 1st European Symposium, 2003.
Park et al. "Efficient Palladium-Catalyzed Amination of Aryl Chlorides Using Dicyclo-Hexylamino[(2,6-Dimethyl)Morpholino]Phenylphosphine as a PN.SUB.2 Ligand". Synthesis, No. 5, pp. 0815-0823, 2009.
Loones et al. "Examination of the Mechanism of the Intramolecular Amination of N-(3-Bromopyridin-2-YL)Azaheteroarylamines and N-(2-Chloropyridin-3-YL)Azaheteroarylamines: A Pd-Catalyzed Amination and/or a Base-Assisted Nucleophilic; Aromatic Substitution?". Tetrahedron, vol. 63, pp. 3818-3825, 2007.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Jonckers et al. "Selective Palladium-Catalyzed Aminations of Dicholoropyridines," Tetrahedron, 2001, vol. 57, pp. 7027-7034.
Kaczmarek et al. "Synthesis and Antineoplastic Properties of Some Benzoiso-.Alpha.-Carbolines". Archiv Der Pharmazie, Weinheim, Germany, vol. 321, No. 8, pp. 463-467, 1988.
Solekhova et al. "Reductive Amination of Quinoline N-Oxide With Aminopyridines and Their N-Tosyl Derivatives". Russian Journal of Organic Chemistry, vol. 38, No. 8, pp. 1192-1194, 2002.
Nguyen et al., "Synthesis and Biological Evaluation of Amino-Substituted Benzo [f]pyrido[4,3-b] and Pyrido [3,4-b] quinoxalines: a New Class of Antineoplastic Agents," Anti-Cancer Drug Design, 1995, vol. 10, No. 4, 277-97.
Baklanov et al., "Photocyclization of (o-haloaryl)hetarylamines," Zhurnal Organicheskoi Khimii, 1991, vol. 27, No. 3, pp. 638-649.
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Prostakov et al., "Schiff Bases in Syntheses of Substituted Naphthylamines, Napthyridines, Azophenanthrenes, and Benzocarbazole," Khimiya Geterotsiklicheskikh Soedinenii, 1972, vol. 10, pp. 1400-1403.
Grout et al., "Polyazabenzo[a]pyrenes," Journal of the Chemical Society [Section] C: Organic, 1968, vol. 21, pp. 2689-2693.
Talik et al., "2-Chloro-3, 5-dinitropyridine. 1. Exchange Reactions of the Chlorine Atom," Bulletin de L'Academie Polonaise des Sciences, Serie Des Sciences Chimiques, 1960, vol. 8, No. 5, pp. 219-222.
Deuerleine, "Dipryridyl-, diquinolyl-, and Pyridylquinolylamines," Journal fuer Praktische Chemie (Liepzig), 1923, vol. 106, pp. 53-65.
Kondratenko et al. "Bactericidal Activity of Some Derivatives of N-Heteroaromatic Compounds". Mikrobiologichnii Zhurnal, 1934-1977, vol. 40, No. 3, pp. 368-370 (abstract only), 1978.
Gritsenko et al., "Synthesis in Phenothiazines. XXXIX. Dimethylpyridophenothiazines," Khimiya Geterotsiklicheskikh Soedinenii,1975, vol. 1, pp. 50-54.

(56) References Cited

OTHER PUBLICATIONS

Buchmann et al., "The Preparation and Reactivity of 4-hydroxy-7-chloroquinaldine," Journal fuer Praktische Chemie, 1962, vol. 17, pp. 135-146.
Khalifa. "Hutchinson-Gilford Progeria Syndrome: Report of a Libyan Family and Evidence of Autosomal Recessive Inheritance". Clinical Genetics, vol. 35, pp. 125-132, 1989.
De Sandre-Giovannoli et al. "Lamin A Truncation in Hutchinson-Gilford Progeria". Science, vol. 300, p. 2055, 2003.
Pendas et al. "Defective Prelamin A Processing and Muscular and Adipocyte Alterations in Zmpste24 Metalloproteinsase-Deficient Mice". Nature Genetics, vol. 31, pp. 94-99, 2002.
De Sandre-Giovannoli et al., "Altered Splicing in Prelamin A-associated Premature Aging Phenotypes," Progress in Molecular and Subcellular Biology, 2006, pp. 199-232.
Fong et al., "A Protein Farnesyltransferase Inhibitor Ameliorates Disease in a Mouse Model of Progeria," Science, 2006, vol. 311, pp. 1621-1623.
Varela et al., "Combined Treatment with Statins and Aminobisphosphonates Extends Longevity in a Mouse Model of Human Premature Aging," Nature Medicine, 2008, vol. 14, No. 7, pp. 767-772.
Labourier et al. "Recognition of Exonic Splicing Enhancer Sequences by the *Drosophila* Splicing Repressor RSF1". Nucleic Acids Research, vol. 27, No. 11, pp. 2377-2386, 1999.
Dignam et al., "Eukaryotic Gene Transcription with Purified Components," Methods in Enzymology, 1983, vol. 101, pp. 582-598.
Tazi et al. "A Protein That Specifically Recognizes the 3' Splice Site of Mammalian Pre-MRNA Introns Is Associated With a Small Nuclear Ribonucleoprotein" Cell, vol. 47, pp. 755-766, 1986.
Sanchez-Martin et al. "Symmetrical Bis-Quinolinium Compounds: New Human Choline Kinase Inhibitors with Antiproliferative Activity against the HT-29 Cell Line". Journal of Medicinal Chemistry, vol. 48, No. 9, pp. 3354-3363, 2005.
Cottet et al., "Recommendable Routes to Trifluoromethyl-Substituted Pyridine-and Quinolinecarboxylic Acids," Eur. J. Org. Chem., 2003, pp. 1559-1568.
Balkau et al., "Syntheis of Ellipticine Intermediates: 6-Amino-, 6-hydroxy-, and 6-Methoxy-5,8-Dimethylisoquinoline," Australian. J. Chem., 1969, vol. 22, pp. 2489-2492.
Sharp. "Split Genes and RNA Splicing". Cell, vol. 77, pp. 805-815, 1994.
Black, "Mechanisms of Alternative Pre-Messenger RNA Splicing," Annu. Rev. Biochem., 2003, vol. 72, pp. 291-336.
Manley et al. "SR Proteins and Splicing Control". Genes & Development, vol. 10, pp. 1569-1579,1996.
Graveley, "Sorting out the Complexity of SR Protein Functions," RNA, 2000, vol. 6, pp. 1197-1211.
Wang et al. "SC35 Plays a Role in T Cell Development and Alternative Splicing of CD45". Molecular Cell, vol. 7, pp. 331-342, 2001.
Ewing et al., "Analysis of Expressed Sequence Tags Indicates 35,000 Human Genes," Nature Genetics, 2000, vol. 25, pp. 232-234.
Cartegni et al., "Listening to Silence and Understanding Nonsense: Exonic Mutations that Affect Splicing," Nature Reviews—Genetics, Apr. 2002, vol. 3, pp. 285-298.
Tazi et al. "The Spliceosome: A Novel Multi-Faceted Target for Therapy". Trends in Biochemical Sciences, vol. 30, No. 8, pp. 469-478, 2005.
Nissim-Rafinia et al., "Cellular and Viral Splicing Factors Can Modify the Splicing Pattern of CFTR Transcripts Carrying Splicing Mutations," Human Molecular Genetics, 2000, vol. 9, No. 12, pp. 1771-1778.
Hofmann et al., "Htra2-ß1 Stimulates an Exonic Splicing Enhancer and can Restore Full-length SMN Expression to Survival Motor Neuron 2 (SMN2)," PNAS, 2000, vol. 97, No. 17, pp. 9618-9623.
Sazani et al. "Systemically Delivered Antisense Oligomers Upregulate Gene Expression in Mouse Tissues". Nature Biotechnology, vol. 20, pp. 1228-1233, 2002.

Sazani et al. "Modulation of Alternative Splicing by Antisense Oligonucleotides". Prog. Mol. Subcell. Biol., vol. 31, pp. 217-239, 2003.
Cartegni et al., "Correction of Disease-associated Exon Skipping by Synthetic Exon-specific Activators," Nature Structural Biology, 2003, vol. 10, No. 2, pp. 120-125.
Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.
Liu et al. "Partial Correction of Endogenous F508 CFTR in Human Cystic Fibrosis Airway Epithelia by Spliceosome-Mediated RNA Trans-Splicing". Nature Biotechnology, vol. 20, pp. 47-52, 2002.
Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.
Connor et al., "Vpr is Required for Efficient Replication of Human Immunodeficiency Virus type-1 in Mononuclear Phagocytes," Virology, 1995, vol. 206, pp. 935-944.
Dec. 23, 2013 Office Action issued in U.S. Appl. No. 13/377,753.
Wang et al. "Alternative Isoform Regulation in Human Tissue Transcriptomes". Nature, vol. 456, pp. 470-476, 2008.
Pan et al., "Deep surveying of alternative splicing complexity in the human transcriptome by high-throughput sequencing, "Nature Genetics, vol. 40, No. 12, pp. 1413-1415, Dec. 2008.
F. J. Leinweber, "Possible Physiological Roles of Carboxylic Ester Hydrolases," Drug Metabolism Reviews, vol. 18, No. 4, pp. 379-439, 1987.
Mar. 9, 2012 International Search Report issued in International Patent Application No. PCT/IB2011/055643.
Jun. 18, 2013 International Preliminary Report on Patentability issued in International Patent Application No. PCT/IB2011/055643.
U.S. Appl. No. 13/377,753, filed Jun. 4, 2012 in the name of Tazi et al.
U.S. Appl. No. 13/377,745, filed Jul. 5, 2012 in the name of Roux et al.
U.S. Appl. No. 13/993,990, filed Jun. 13, 2013 in the name of Tazi et al.
Johnson et al., "Genome-Wide Survey of Human Alternative Pre-mRNA Splicing with Exon Junction Microarrays," Science, vol. 302, pp. 2141-2144, 2003.
Aug. 15, 2014 Office Action issued in U.S. Appl. No. 13/377,751.
El-Sayed et al. "Synthesis of Some Novel Quinoline-3-Carboxylic Acids and Pyrimidoquinoline Derivatives As Potential Antimicrobial Agents". Archiv der Pharmize, vol. 335, No. 9, pp. 403-410, 2002.
Silberg et al. "N-Acyl-N, N-Dipyridyl and N-Acyl-N-Pyridyl-N-Quinoyl Amine Based Palladium Complexes. Synthesis, X-Ray Structures, Heterogenization and Use in Heck Couplings". Journal of Organmetallic Chemistry, vol. 622, pp. 6-18, 2001.
File Registry on STN, 195876-33-6/RN, entered on Oct. 23, 1997.
File Registry on STN, 70125-24-5/RN, entered on Nov. 16, 1984.
Dec. 5, 2014 Office Action issued in U.S. Appl. No. 14/087,762.
CAS Registry No. 215589-34-7 added on STN on Dec. 15, 1998.
CAS Registry No. 208661-32-9 added on STN on Jul. 19, 1998.
CAS Registry No. 204851-25-2 added on STN on Apr. 30, 1998.
CAS Registry No. 138386-77-3 added on STN on Jan. 17, 1992.
CAS Registry No. 70682-97-2 added on STN on Nov. 16, 1984.
CAS Registry No. 10562-04-6 added on STN on Nov. 16, 1984.
CAS Registry No. 5468-85-9 added on STN on Nov. 16, 1984.
CAS Registry No. 313266-85-2 added on STN on Jan. 9, 2001.
CAS Registry No. 294668-01-2 added on STN on Oct. 11, 2000.
CAS Registry No. 342653-87-6 added on STN on Jun. 20, 2001.
CAS Registry No. 449780-95-4 added on Stn on Sep. 12, 2002.
CAS Registry No. 449780-94-3 added on STN on Sep. 12, 2002.
CAS Registry No. 324526-73-0 added on STN on Feb. 27, 2001.
Jan. 13, 2015 Russian Office Action issued in Russian Application No. 2011149572/04(074427).
Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.

(56) References Cited

OTHER PUBLICATIONS

U.S. Appl. No. 13/377,760, filed Jul. 2, 2012 in the name of Tazi et al.
Nov. 10, 2014 International Search Report issued in International Application No. PCT/IB2014/062849.
Nov. 10, 2014 Written Opinion issued in International Application No. PCT/IB2014/062849.
File Registry on STN, 92873-44-4, entered on Dec. 7, 1984.
File Registry on STN, 94541-69-2, entered on Feb. 3, 1985.
File Registry on STN, 97978-62-6, entered on Sep. 16, 1985.
File Registry on STN, 67412-46-8, entered on Nov. 16, 1984.
File Registry on STN, 55360-88-8, entered on Nov. 16, 1984.
File Registry on STN, 101350-67-8, entered on Apr. 5, 1986.
Jan. 24, 2018 Office Action issued in U.S. Appl. No. 15/486,836.
Feb. 1, 2018 Office Action issued in U.S. Appl. No. 13/377,753.
Fors et al., "An Efficient Process for Pd-Catalyzed C—N Cross-Coupling Reactions of Aryl Iodides: Insight Into Controlling Factors," J. Am. Chem. Soc., 2009, 131, 5766-5768.
Jun. 14, 2018 Office Action Issued in U.S. Appl. No. 15/326,698.
Walker et al., "Rheumatic conditions in human immunodeficiency virus infection," (Rheumatology 2008;47:952-959). (Year: 2008).
U.S. Appl. No. 15/486,836, filed Apr. 13, 2017 in the name of Tazi et al.
J. Tazi et al., "Alternative Splicing and Disease," Biochimica et Biophysica Acta, 1792 (2009), 14-26.
Yanborisova et al., "Synthesis and Antiinflammatory Activity of 2-Arylaminocinchoninic Acids and Amides of 1,2-Dihydro-2-Oxocinchoninic Acid," Pharmaceutical Chemistry Journal, vol. 29, No. 6, Jun. 1995, pp. 404-405.
Etukala et al., "A Short and Convenient Synthesis and Evaluation of the Antiinfective Properties of Indoloquinoline Alkaloids: 10H-Indolo[3,2-b]quinoline and 7H-Indolo[2,3-c]quinolines," Journal of Heterocyclic Chemistry, No. 45, Mar. 2008, pp. 507-511.
Feb. 5, 2019 Office Action Issued in U.S. Appl. No. 15/326,698.
STN Database Registration No. 933238-11-0, Chemical Abstracts Service, American Chemical Society, Registered Apr. 29, 2007, pp. 1-4.
S.D. Carter et al. "Quinoxalines and Related Compounds—X: The Formation of Indolo[2,3-b]Quinoxalines and 2-p-Aminophenyl-3-Anilinoquinoxalines from 2-Anilinoquinoxalines." Tetrahedron, Pergamon Press, vol. 34, Issue No. 7, 1978, pp. 981-988.
STN Database Registration No. 374598-11-5, Chemical Abstracts Service, American Chemical Society, Registered Oct. 1, 2007, pp. 1-10.
G. Bhattancharjee et al. "Synthesis of physiologically important quinoxaline derivatives using conventional method and microwave irradiation." Indian Journal of Chemical Technology, Council of Scientific & Industrial Research, vol. 15, No. 1, Jan. 2008, pp. 72-74.
STN Database Registration No. 397881-66-2, Chemical Abstracts Service, American Chemical Society, Registered Mar. 4, 2002, 1 page.
Wang et al. "A Direct Intramolecular C—H Amination Reaction Cocatalyzed by Copper (II) and Iron (III) as Part of an Efficient Route for the Synthesis of Pyrido[1,2-a]benzimidazoles from N-Aryl-2-aminopyridines." Journal of the American Chemical Society, ACS Publications, vol. 132, Sep. 2010, pp. 13217-13219.
Hostyn et al. "Synthesis of ?—Carbolines Starting from 2,3-Dichloropyridines and Substituted Anilines." Advanced Synthesis & Catalysis, Wiley, vol. 350, Oct. 2008, pp. 2653-2660.
Organ et al. "Pd-Catalyzed Aryl Amination Mediated by Well Defined, N-Heterocyclic Carbene (NHC)-Pd Precatalysts, PEPPSI**." Chemistry: A European Journal, Wiley, vol. 14, Feb. 2008, pp. 2443-2452.
Maes et al. "The First Rapid Palladium-Catalyzed Aminations of (Azahetero)aryl Chlorides under Temperature-Controlled Microwave Heating." Synlett, Thieme Medical Publishers, No. 12, Sep. 2003, pp. 1822-1825.
Schmittel et al. "Two Novel Thermal Biradical Cyclizations in Theory and Experiment: New Synthetic Routes to 6H-Indolo[2,3-b]quinolines and 2-Amino-quinolines from Enyne-Carbodiimides**." Angewandte Chemie International Edition, Wiley, vol. 37, No. 17, Dec. 1998, pp. 2371-2373.
Rauws et al. "Synthesis of new tetracyclic azaheteroaromatic cores via auto-tandem Pd-catalyzed and one-pot Pd-and Cu-catalyzed double C—N bond formation." Tetrahedron, Elsevier, vol. 66, Jun. 2010. 6958-6964.
CAS (Chemical Abstracts Service) Registry No. 1011408-51-7, American Chemical Society, added on STN on Apr. 1, 2008, 1 page.
CAS (Chemical Abstracts Service) Registry No. 92873-44-4, American Chemical Society, added on STN on 7 Dec. 1984, 1 page.
CAS (Chemical Abstracts Service) Registry No. 94541-69-2, American Chemical Society, added on STN on Feb. 3, 1985, 1 page.
Dobson, J. et al., "Attempts to find new antimalarials. XXVII. Derivatives of various benzacridines and pyridoacridines", Journal of the Chemical Society, pp. 123-126, Jan. 1948.
Jan. 22, 2020 Office Action issued in U.S. Appl. No. 16/502,663.
Lin Min et al., "Nonsense-mediated mRNA decay and tumors," Journal of International Pathology and Clinical Medicine, vol. 26, No. 4, pp. 291-294. (Aug. 31, 2006).
Nov. 16, 2020 Office Action issued in Japanese Patent Application No. 2019-191500.

* cited by examiner

COMPOUNDS AND PHARMACEUTICAL COMPOSITIONS CONTAINING AT LEAST ONE OF THE COMPOUNDS

This is a divisional of U.S. application Ser. No. 16/050,551 filed Jul. 31, 2018, which is a divisional of U.S. application Ser. No. 15/486,836 filed Apr. 13, 2017 (now U.S. Pat. No. 10,253,020), which is a continuation-in-part of:

U.S. application Ser. No. 14/789,149 filed Jul. 1, 2015,
U.S. application Ser. No. 14/789,250 filed Jul. 1, 2015,
U.S. application Ser. No. 14/256,334 filed Apr. 18, 2014, and
U.S. application Ser. No. 13/377,753 filed Jun. 4, 2012;

U.S. application Ser. No. 14/789,149 filed Jul. 1, 2015, is a continuation of U.S. application Ser. No. 14/087,762 filed Nov. 22, 2013, now U.S. Pat. No. 9,108,919, which is a continuation of application Ser. No. 13/377,745 filed Jul. 5, 2012, now abandoned, which is a National Stage Application of PCT/IB2010/052560 filed Jun. 14, 2010, and claims the benefit of U.S. Provisional Application Nos. 61/186,552 and 61/186,544 and European Application Nos. 09305540.8 and 09162630.9, all of which were filed on Jun. 12, 2009;

U.S. application Ser. No. 14/789,250 filed Jul. 1, 2015, is a continuation of U.S. application Ser. No. 13/377,760 filed Jul. 2, 2012, now U.S. Pat. No. 9,145,367, which is a National Stage Application of PCT/IB2010/052651 filed Jun. 14, 2010, and claims the benefit of U.S. Provisional Application Nos. 61/186,544 and 61/186,552 and European Application Nos. 09162630.9 and 09305540.8, all of which were filed on Jun. 12, 2009;

U.S. application Ser. No. 14/256,334 filed Apr. 18, 2014 is a continuation of U.S. application Ser. No. 13/377,760 filed Jul. 2, 2012, now U.S. Pat. No. 9,145,367, which is a National Stage Application of PCT/IB2010/052651 filed Jun. 14, 2010, and claims the benefit of U.S. Provisional Application Nos. 61/186,544 and 61/186,552 and European Application Nos. 09162630.9 and 09305540.8, all of which were filed on Jun. 12, 2009; and U.S. application Ser. No. 13/377,753 filed Jun. 4, 2012 is a National Stage Application of PCT/IB2010/052652 filed Jun. 14, 2010, and claims the benefit of U.S. Provisional Application Nos. 61/186,544 and 61/186,552 and European Application Nos. 09162630.9 and 09305540.8, all of which were filed on Jun. 12, 2009. The entire disclosures of each of the above-mentioned prior applications are hereby incorporated by reference herein in their entireties.

FIELD OF THE INVENTION

The present disclosure is generally directed to the manufacture and use of compounds described herein for preventing, inhibiting or treating cancer, AIDS and/or premature aging.

BACKGROUND OF THE INVENTION

Cancer

In most cancers, mortality is not due to the primary tumor but rather to the derived metastases. This malignant progression is clinically defined by the appearance of metastatic cells. Tumor metastases are typically defined by a primary loss of cell adhesion and an increase of cell motility, which allows for invasive cell to leave the initial tumor site and colonize various target tissues.

Metastases are considered as a recurrent feature of uncontrolled malignant progression of cancer. During this process, tumor cells complete their malignant transformation by increasing their migratory capacity. Cancer cells can then disseminate and establish new tumor foci in far away sites. This event is termed "metastatic cascade," which, as indicated immediately above, is marked by invasion of tissues around the tumor, venous or lymphatic intravasation, migration and establishment of new tumors in distant places of an organism that may escape from all innate defense mechanisms.

Because no efficient therapeutic options presently exist for the treatment or prevention of metastatic tumors, metastatic invasion a major cause of death worldwide. Due to the frequency of cancers diagnosed at the metastatic stage and the lack of viable therapeutic options at this stage of the disease, the development of molecules that specifically target metastatic invasion is crucial for a major breakthrough in cancer treatments.

The compounds and methods of use as described herein are consistent with numerous published reports during the last twenty years that demonstrate a link between changes in RNA alternative splicing and metastatic invasion, which has opened new avenues for therapeutic strategies.

AIDS

Certain indole derivative compounds such as ellipticine derivatives and aza-ellipticine derivatives are already known as intercalating molecules for correcting dysfunctions in gene expression, notably in DNA replication. They have been more specifically described for treating diseases such as cancer, leukemia or AIDS (see in particular patents FR 2 627 493, FR 2 645 861, FR 2 436 786).

Concerning current treatments for AIDS, the various approaches aimed at reducing viral load in patients infected by HIV utilize molecules intended to inhibit the enzymatic activity of viral reverse transcriptase or of the protease involved in virus protein maturation. Regarding reverse transcriptase inhibitors, these can be nucleosidic (NRTIs), non-nucleosidic (NNRTIs) or nucleotidic in nature. The purpose of using these compounds is to prevent a DNA copy of the retroviral genome from being produced and, consequently, from being integrated into the genome of the host cell. Protease inhibitors (PIs) interfere with the proper maturation of viral proteins and cause the production of incomplete particles with altered infectious capacities. There is another type of anti-retroviral compound used for its ability to prevent viruses from entering the cell. These entry inhibitors can be either peptides that interfere with the fusion of viral glycoproteins gp41 or gp120 with the membrane of CD4 cells or molecules that target HIV cellular co-receptors CCR5 and CXCR4. The absence of cellular proteins resembling HIV integrase has also been exploited to develop novel anti-HIV molecules that inhibit this enzymatic activity. Although a number of integrase inhibitors are in the clinical trial phase, no molecule is yet available on the market.

The intracellular splicing process consists of eliminating introns in pre-messenger RNAs to produce mature messenger RNAs that can be used by the translation mechanism of the cell (SHARP, Cell, vol. 77, p. 805-815, 1994). In the case of alternative splicing, the same precursor can be the source of messenger RNAs coding for proteins with distinct functions (BLACK, Annu. Rev. Biochem. vol. 72, p. 291-336, 2003). The precise selection of 5' and 3' splicing sites is thus a mechanism that generates diversity and that can lead to the regulation of gene expression according to the type of tissue or during the development of an organism. The factors involved in this selection include a family of proteins called SR, characterized by the presence of one or two RNA recognition motifs (RRM) and a domain rich in arginine and serine residues called an RS domain (MANLEY & TACKE, *Genes Dev.*, vol. 10, p. 1569-1579, 1996). By binding to short exon or intron sequences of the pre-mRNA, called ESE (exonic splicing enhancer) or ISE (intronic splicing enhancer), SR proteins are able to activate, in a dose-dependant manner, sub-optimal splicing sites and to enable the inclusion of exons (GRAVELEY, *RNA*, vol. 6, p. 1197-1211, 2000). The activity of an SR protein in alternative splicing is specific insofar as the inactivation of the corresponding gene is lethal (WANG et al., *Mol. Cell*, vol. 7, p. 331-342, 2001).

Sequencing of the human genome and analysis of EST (expressed sequence tag) banks has revealed that 65% of genes are expressed in the form of alternatively spliced variants (EWING & GREEN, *Nat. Genet.*, vol. 25, p. 232-234, 2000; JOHNSON et al., *Science*, vol. 302, p. 2141-2144, 2003). This mechanism is thus a favored target of modifications that can affect the factors involved in regulating splicing and of mutations that affect the sequences necessary for this regulation. At present, it is estimated that roughly 50% of the point mutations responsible for genetic diseases induce aberrant splicing. These mutations can interfere with splicing by inactivating or creating splicing sites, but also by modifying or generating regulating elements such as splicing enhancers or splicing silencers in a particular gene (CARTEGNI et al., *Nat. Rev. Genet.*, vol. 3, p. 285-298, 2002; TAZI et al., *TIBS*, vol. 40, p. 469-478, 2005).

The strategies currently developed to correct these splicing defects rest on the use of various types of molecules (TAZI et al., cited above, 2005).

One strategy aimed at developing novel molecules to correct or eliminate abnormal splicing, for example, rests on the overexpression of proteins that interfere with this type of splicing (NISSIM-RAFINIA et al., *Hum. Mol. Genet.*, vol. 9, p. 1771-1778, 2000; HOFINANN et al., *Proc. Natl. Acad. Sci. U.S.A.*, vol. 97, p. 9618-9623, 2000).

Other strategies rest on the use of antisense oligonucleotides (SAZANI et al., *Nat. Biotechnol.*, vol. 20, p. 1228-1233, 2002; SAZANI & KOLE, *Prog. Mol. Subcell. Biol.*, vol. 31, p. 217-239, 2003) or of PNA (CARTEGNI et al., *Nat. Struct. Biol.*, vol. 10, p. 120-125, 2003) enabling, respectively, the inhibition or activation of a splicing event.

Yet another strategy rests on the identification of compounds that influence the splicing efficiency of the pre-mRNA of interest (ANDREASSI et al., *Hum. Mol. Genet.*, vol. 10, p. 2841-2849, 2001).

Lastly, a strategy based on the use of trans-splicing to replace mutant exons has been described (LIU et al., *Nat. Biotechnol.*, vol. 20, p. 47-52, 2002).

One of the disadvantages of the developed strategies cited above to correct or eliminate abnormal splicing is their production cost. Indeed, the cost of producing antisense oligonucleotides that must be modified to improve their stability, and that of PNA molecules, is high.

Another disadvantage of the developed strategies cited above is that they require the use of expression vectors, such as, for example, for the strategy based on the use of trans-splicing.

International application WO05023255, under French priority of applications FR0310460 and FR0400973, filed by the Applicant, disclosed the use of indole derivatives to treat diseases related to the pre-messenger RNA splicing process in the cell.

Thus it was recently shown that certain indole derivatives prove particularly effective in treating metastatic cancer and in treating AIDS (BAKKOUR et al., *PLoS Pathogens*, vol. 3, p. 1530-1539, 2007).

However, the compounds described have a flat structure with four rings that have the disadvantage of intercalating between DNA bases and can thus lead to cellular toxicity.

Premature Aging

Premature aging may be encountered in patients suffering from various diseases and in particular from the Hutchinson-Gilford progeria syndrome (HGPS) and from the HIV infection.

Hutchinson-Gilford progeria syndrome (HGPS) is a rare genetic disorder phenotypically characterized by many features of premature aging. It is clinically characterized by postnatal growth retardation, midface hypoplasia, micrognathia, premature atherosclerosis, absence of subcutaneous fat, alopecia and generalized osteodysplasia (Khalifa, 1989—Hutchinson-Gilford progeria syndrome: report of a Libyan family and evidence of autosomal recessive inheritance. Clin. Genet. 35, 125-132). At birth, the appearance of patients is generally normal, but by 1 year of age patients show severe growth retardation, balding and sclerodermatous skin changes. They average about lm in height and usually weigh less than 15 kg even as teenagers. The age at death ranges from 7 to 28 years, with a median of 13.4 years. Over 80% of deaths are due to heart attacks or congestive heart failure.

Premature aging syndrome has been observed in patients suffering from HIV infections. One mechanical pathway underlying said premature aging could be associated, as for the HGPS and as exposed beneath, with an aberrant splicing of the nuclear lamin A gene. Indeed it has recently been hypothesized that protease inhibitors against HIV also block the transformation of prelamin A into lamin A as it turned out in HGPS.

Most of the patients suffering from premature aging carry a heterozygous silent mutation that activates the use of a cryptic 5' splice site in exon 11 of LMNA pre-mRNA. This aberrant splicing event leads to the production of a truncated protein (progerin) with a dominant negative effect which is responsible for the observed phenotype (De Sandre-Giovannoli et al., 2003—Lamin A truncation in Hutchinson-Gilford progeria. Science 300, 2055/Pendas et al., 2002a—Defective prelamin A processing and muscular and adipocyte alterations in Zmpste24 metalloproteinase-deficient mice. Nat. Genet. 31, 94-99).

Most of the premature aging syndromes in particular associated with Hutchinson-Gilford progeria and HIV infection are due to a recurrent, de novo point mutation in LMNA exon 11: c. 1824C>T. This mutation is localized in the part of the gene specifically encoding lamin A (De Sandre-Giovannoli et al., 2003/De Sandre-Giovannoli and Levy, 2006—Altered splicing in prelamin A-associated premature aging phenotypes. Prog. Mol. Subcell. Biol. 44, 199-232). Its predicted effect is a silent amino acid change at codon 608 (p.G608G). In fact, this sequence variation is not silent as it occurs in a probable exon splicing enhancer. As a result, a cryptic splice site is activated in transcripts issued from the mutated allele, which is located 5 nucleotides upstream of the mutation.

So far, therapeutic approaches have been mainly focused on progerin which is attached to a lipid anchor (a farnesyl lipid anchor). This lipid anchor is attached to progerin by a specific cellular enzyme, protein farnesyltransferase. Experiments in mouse models suggest that farnesyltransferase inhibitors (FTIs) may have beneficial effects in humans with progeria (Fong et al., 2006—A protein farnesyltransferase inhibitor ameliorates disease in a mouse model of progeria. Science 311, 1621-1623). More recently, Nicolas Levy's team has used a combination of a statin and an aminobisphosphonate to prevent the fixation of the fatty acid to the progerin, and thus reduce its toxicity (Varela et al., 2008—Combined treatment with statins and aminobisphosphonates extends longevity in a mouse model of human premature aging. Nat. Med. 14, 767-772).

In WO2006/081444 has been reported a method for reducing at least one cellular defect in a cell from a subject susceptible to a disease or condition characterized by farnesylation on an abnormally farnesylated form of a lamin, comprising administering to the cell a therapeutically effective dose of farnesylstransferase inhibitor.

It has been recently reported in WO2008/003864 the use of a hydroxymethylglutaryl-coenzyme A (HMG-CoA) reductase inhibtor and a farnesyl-pyrophosphate synthase inhibitor, or one of their associated physiologically acceptable salts, in the preparation of a composition, for use in the treatment of human or animal, pathological or nonpathological situations related to the accumulation and/or the persistence of prenylated proteins in cells, such as during progeria, restrictive dermopathy or physiological aging.

In WO 2008/115870 substituted quinoline are described, which are useful for treating cancer.

In US 2008/0161353 other substituted quinoline are disclosed as agents to treat neurological conditions.

SUMMARY OF THE INVENTION

In certain aspects, the compounds described herein may be administered in methods of preventing, inhibiting or treating cancer, AIDS and premature aging. For example, such methods can include administering an effective amount of a compound selected from the group consisting of

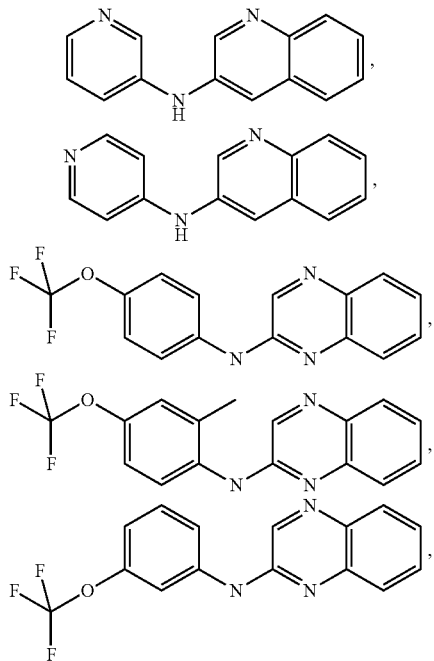

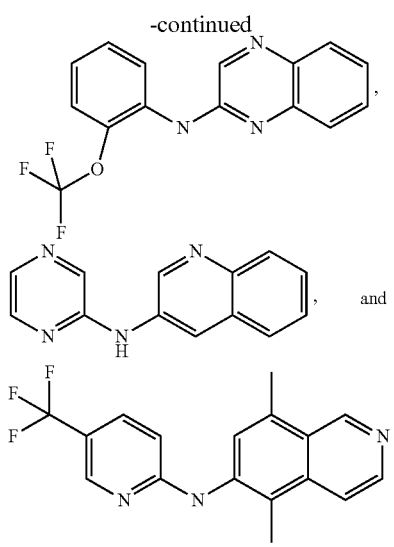

or any derivative thereof as described below or one of its pharmaceutically acceptable salts to a patient. As described in greater detail below, the compounds described herein can be included in pharmaceutical compositions.

DETAILED DESCRIPTION OF THE INVENTION

Embodiment I (Cancer)

Figure 1A:
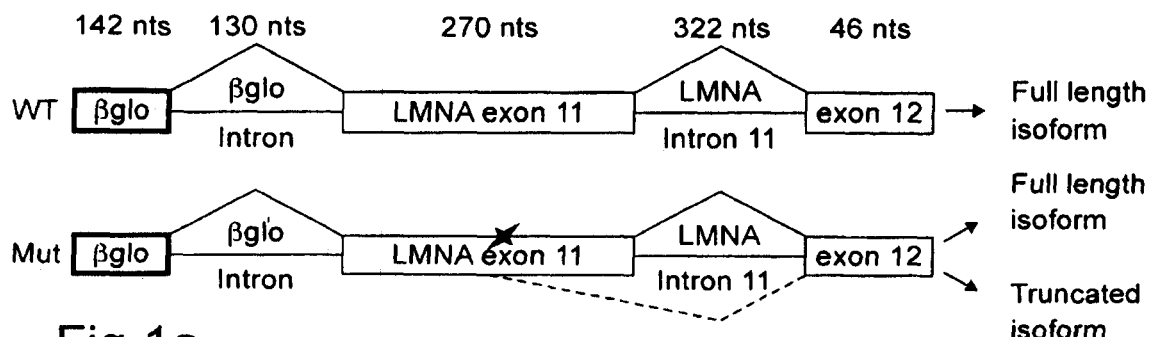
FIG. 1a is schematic representation of the cloning of mutant and wild type constructs carried out using a TOPO-TA cloning vector in which is inserted a minigene containing 142 nts of β-Globin first exon, 130 nts β-Globin first intron, 270 nts LMNA exon 11 either wild type or mutant, 322 nts intron 11 and 46 nts exon 12.

According to a first aspect, the subject-matter described herein relates to a compound of formula (I)

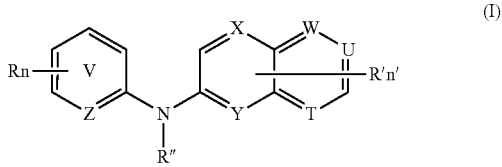

wherein:

means an aromatic ring wherein V is C or N and when V is N, V is in an ortho, meta or para position with respect to Z, i.e. forms respectively a pyridazine, a pyrimidine or a pyrazine group, R independently represents a hydrogen atom, a halogen atom or a group chosen among a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, a ($C_1$-$C_4$)alkoxy group, a phenoxy group and a ($C_1$-$C_3$)alkyl group, the alkyl being optionally mono-substituted by a hydroxyl group, R$_1$ and R$_2$ are independently a hydrogen atom or a ($C_1$-$C_3$)alkyl group, n is 1, 2 or 3, n' is 1 or 2, R' is a hydrogen atom or a group chosen among a ($C_1$-$C_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a ($C_1$-$C_3$)fluoroalkyl group, a ($C_1$-$C_4$) alkoxy group and a —CN group, R" is a hydrogen atom or a ($C_1$-$C_4$)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salt, for use as an agent for preventing, inhibiting or treating cancer.

According to one aspect, formula (I) as defined above includes a compound wherein Z is N, V is C, Y is N, X is C, T is C, U is C and W is C, which can be used as an agent for preventing, inhibiting or treating cancer.

According to another aspect, formula (I) as defined above includes a compound wherein Z is C, V is C, Y is N, X is C, T is C, U is C and W is C, which can be used as an agent for preventing, inhibiting or treating cancer.

According to another aspect, formula (I) as defined above includes a compound wherein Z is N, V is C, Y is C, X is N, T is C, U is C and W is C, which can be used as an agent for preventing, inhibiting or treating cancer.

According to another aspect, formula (I) as defined above includes a compound wherein Z is N, V is C, Y is C, X is C, T is C, U is C and W is N, which can be used as an agent for preventing, inhibiting or treating cancer.

According to another aspect, formula (I) as defined above includes a compound, wherein Z is N, V is N and is in the para position with respect to Z, Y is N, X is C, T is C, U is C and W is C, which can be used as an agent for preventing, inhibiting or treating cancer.

According to another aspect, formula (I) as defined above includes a compound, wherein Z is C, V is N and is in the para position with respect to Z, Y is C, X is N, T is C, U is C and W is C, which can be used as an agent for preventing, inhibiting or treating cancer.

According to another aspect, formula (I) as defined above includes a compound, wherein Z is C, V is N and is in the meta position with respect to Z and is in the para position with respect to the bond linked to NR", Y is N, X is C, T is C, U is C and W is C, for use as an agent for preventing, inhibiting or treating cancer.

According to another aspect, formula (I) as defined above includes a compound, wherein Z is C, V is N and is in the meta position with respect to Z and is in the para position with respect to the bond linked to NR", Y is C, X is N, T is C, U is C and W is C, for use as an agent for preventing, inhibiting or treating cancer.

According to another aspect, formula (I) as defined above includes a compound, wherein Z is C, V is C, Y is C, X is N, T is C, U is C and W is C, for use as an agent for preventing, inhibiting or treating cancer.

According to another aspect, formula (I) as defined above includes a compound, wherein Z is C, V is C, Y is N, X is N, T is C, U is C and W is C, for use as an agent for preventing, inhibiting or treating cancer.

According to another aspect, formula (I) as defined above includes a compound, wherein Z is N, V is N and is in the meta position with respect to Z and in the ortho position with respect to the bond linked to NR", Y is N, X is C, T is C, U is C and W is C, for use as an agent for preventing, inhibiting or treating cancer.

According to another aspect, formula (I) as defined above includes a compound, wherein Z is N, V is N and is in the para position with respect to Z, Y is C, X is C, T is C, U is C and W is N, for use as an agent for preventing, inhibiting or treating cancer.

According to another aspect, formula (I) as defined above includes a compound, wherein Z is N, V is N and is in the para position with respect to Z, Y is C, X is N, T is C, U is C and W is C, for use as an agent for preventing, inhibiting or treating cancer.

According to another aspect, formula (I) as defined above includes a compound, wherein Z is N, V is C, Y is N, X is N, T is C, U is C and W is C, for use as an agent for preventing, inhibiting or treating cancer.

According to another aspect, formula (I) as defined above includes a compound, wherein Z is N, V is N and is in the meta position with respect to Z and is in the ortho position with respect to the bond linked to NR", Y is N, X is N, T is C, U is C and W is C, for use as an agent for preventing, inhibiting or treating cancer.

According to another aspect, formula (I) as defined above includes a compound, wherein Z is C, V is C, Y is C, X is C, T is N, U is C and W is C, for use as an agent for preventing, inhibiting or treating cancer.

According to another aspect, formula (I) as defined above includes a compound, wherein Z is N, V is C, Y is C, X is C, T is N, U is C and W is C, for use as an agent for preventing, inhibiting or treating cancer.

According to another aspect, formula (I) as defined above includes a compound, wherein Z is N, V is C, Y is C, X is C, T is C, U is N and W is C, for use as an agent for preventing, inhibiting or treating cancer.

According to one preferred aspect, formula (I) as defined above, wherein Z is N, V is C, Y is N, X is C, T is C, U is C and W is C, for use as an agent for preventing, inhibiting or treating cancer.

According to another preferred aspect, formula (I) as defined above includes a compound, wherein Z is N, V is N and is in the para position with respect to Z, Y is N, X is C, T is C, U is C and W is C, for use as an agent for preventing, inhibiting or treating cancer.

According to another preferred aspect, formula (I) as defined above includes a compound, wherein Z is C, V is C, Y is C, X is C, T is N, U is C and W is C, for use as an agent for preventing, inhibiting or treating cancer.

According to another preferred aspect, formula (I) as defined above includes a compound, wherein Z is N, V is C, Y is C, X is C, T is C, U is N and W is C, for use as an agent for preventing, inhibiting or treating cancer.

The compounds described herein may exist in the form of free bases or of addition salts with pharmaceutically acceptable acids.

The compounds of formula (I) can include physiologically acceptable acid addition salts such as hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates (e.g. hydrates) and the compounds describe herein can include all such solvates.

In the context of EMBODIMENT I of the present disclosure, the term:

"halogen" is understood to mean chlorine, fluorine, bromine, or iodine, and in particular denotes chlorine, fluorine or bromine, "$(C_1-C_3)$alkyl" as used herein respectively refers to $C_1-C_3$ normal, secondary or tertiary saturated hydrocarbon. Examples are, but are not limited to, methyl, ethyl, 1-propyl, 2-propyl, "$(C_1-C_3)$alkoxy" as used herein respectively refers to O—$(C_1-C_3)$alkyl moiety, wherein alkyl is as defined above. Examples include, but are not limited to, methoxy, ethoxy, 1-propoxy, 2-propoxy, "fluoroalkyl group" and "fluoroalkoxy group" refers respectively to alkyl group and alkoxy group as above-defined, the groups being substituted by at least one fluorine atom. Examples of perfluoroalkyl groups include, but are not limited to, trifluoromethyl or perfluoropropyl.

"patient" may extend to humans or mammals. For example, the term "patient" can include cats or dogs.

In one aspect, the compounds described herein include a compound of formula (Ia)

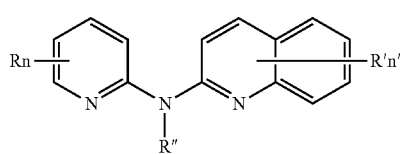

wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group,
R" is as defined above and is advantageously a hydrogen atom,
n is as defined above and is advantageously 1,
n' is as defined above and is advantageously 1,
R' is a hydrogen atom, a halogen atom or a group chosen among a $(C_1-C_3)$alkyl group, a —NO$_2$ group, a $(C_1-C_3)$alkoxy group and a —NR$_1$R$_2$ group,
R$_1$ and R$_2$ are a hydrogen atom or a $(C_1-C_3)$alkyl group, or one of its pharmaceutically acceptable salt,
for use as an agent for preventing, inhibiting or treating cancer.

In one aspect, the compounds described herein include a compound of formula (Ib)

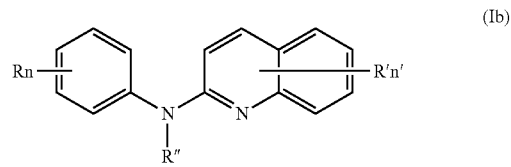

wherein:
R independently represent a hydrogen atom, a halogen atom or a group chosen among a $(C_1-C_3)$alkyl group, a —NR$_1$R$_2$ group, a $(C_1-C_3)$fluoroalkoxy group, a —NO$_2$ group, a phenoxy group and a $(C_1-C_4)$alkoxy group,
R$_1$ and R$_2$ are independently a hydrogen atom or a $(C_1-C_3)$alkyl group,
R" is as defined above and is advantageously a hydrogen atom,
n is as defined above and is preferably 1 or 2,
n' is as defined above and is preferably 1,
R' is a hydrogen atom, a halogen atom or a group chosen among a $(C_1-C_3)$alkyl group and a $(C_1-C_4)$alkoxy group,
or one of its pharmaceutically acceptable salt,
for use as an agent for preventing, inhibiting or treating cancer.

In one aspect, the compounds described herein include a compound of formula (Ic)

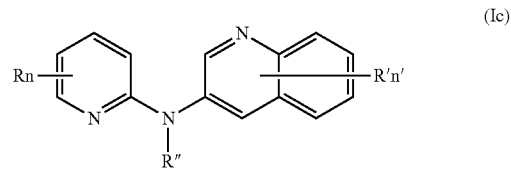

wherein:
R independently represent a hydrogen atom or a group chosen among a $(C_1-C_3)$alkyl group, a $(C_1-C_3)$fluoroalkyl group, a —NR$_1$R$_2$ group, a —COOR$_1$ group, a —NO$_2$ group and a $(C_1-C_3)$alkoxy group,
R" is as defined above and is advantageously a hydrogen atom,
n is as defined above and is advantageously 1,
n' is as defined above and is advantageously 1,
R' is a hydrogen atom,
R$_1$ and R$_2$ are independently a hydrogen atom or a $(C_1-C_3)$alkyl group,
or one of its pharmaceutically acceptable salt,
for use as an agent for preventing, inhibiting or treating cancer.

In one aspect, the compounds described herein include a compound of formula (Id)

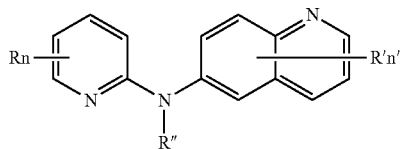

(Id)

wherein:
R independently represents a hydrogen atom or a group chosen among a $(C_1-C_3)$alkyl group, a $(C_1-C_3)$fluoroalkyl group and a $(C_1-C_3)$alkoxy group,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In certain aspects, the compounds described herein include a compound of formula (Ie)

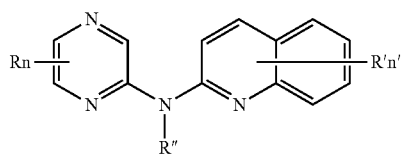

(Ie)

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a group chosen among a $(C_1-C_3)$alkyl group and a $(C_1-C_3)$alkoxy group,
or one of its pharmaceutically acceptable salt,
for use as an agent for preventing, inhibiting or treating cancer.

In another aspect, the compounds described herein include a compound of formula (If)

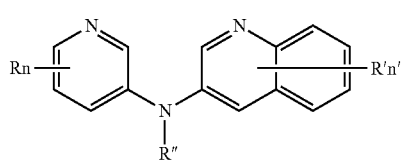

(If)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ig)

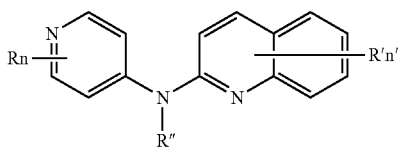

(Ig)

wherein:
R represents a hydrogen atom,
R" is as defined above and is advantageously a hydrogen atom,
n is as defined above and is advantageously 1,
n' is as defined above and is advantageously 1,
R' is a hydrogen atom or a halogen atom,
or one of its pharmaceutically acceptable salt,
for use as an agent for preventing, inhibiting or treating cancer.

In one aspect, the compounds described herein include a compound of formula (Ih)

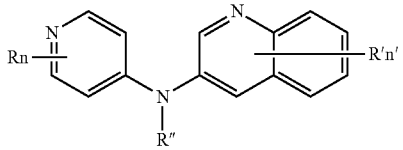

(Ih)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ii)

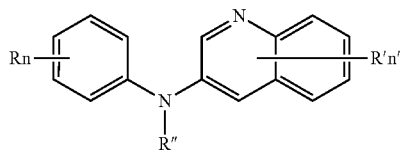

(Ii)

wherein:
R independently represents a hydrogen atom or a group chosen among a $(C_1-C_3)$fluoroalkoxy group and a $(C_1-C_3)$alkoxy group,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ij)

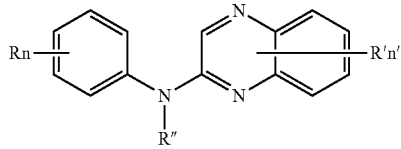

(Ij)

wherein:
R independently represents a hydrogen atom or a group chosen among a $(C_1-C_3)$fluoroalkoxy group and a $(C_1-C_3)$alkyl group,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ik)

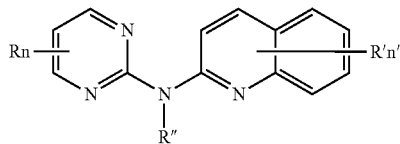

(Ik)

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a $(C_1-C_3)$alkyl group,
or one of its pharmaceutically acceptable salt,
for use as an agent for preventing, inhibiting or treating cancer.

In one aspect, the compounds described herein include a compound of formula (Il)

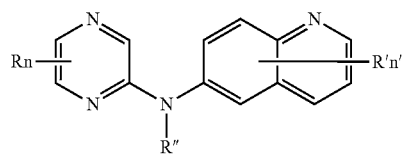

(Il)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Im)

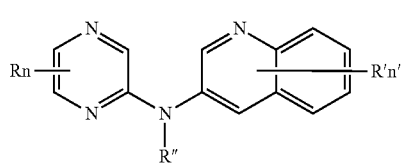

(Im)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Io)

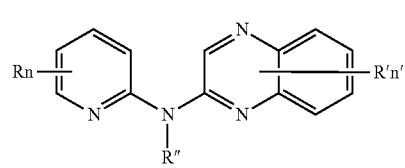

(Io)

wherein:
R independently represent a hydrogen atom or a halogen atom or a group chosen among, a —$NO_2$ group, a —CN group and a $(C_1-C_3)$alkyl group, said alkyl being optionally mono-substituted by a hydroxyl group,
R" is as defined above and is advantageously a hydrogen atom,
n is as defined above and is advantageously 1,
n' is as defined above and is advantageously 1,
R' is a hydrogen atom, a halogen atom or a $(C_1-C_3)$ fluoroalkyl group,
or one of its pharmaceutically acceptable salt,
for use as an agent for preventing, inhibiting or treating cancer.

In one aspect, the compounds described herein include a compound of formula (Ip)

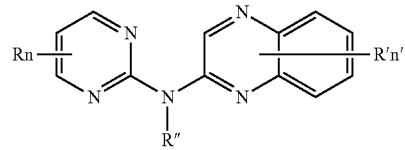

(Ip)

wherein:
R represents a hydrogen atom,
R" is as defined above and is advantageously a hydrogen atom,
n is as defined above and is advantageously 1, n' is as defined above and is advantageously 1, R' is a hydrogen atom, or one of its pharmaceutically acceptable salt, for use as an agent for preventing, inhibiting or treating cancer.

In one aspect, the compounds described herein include a compound of formula (Iq)

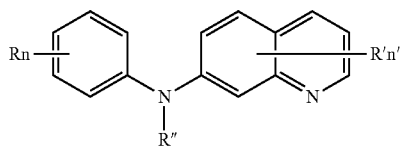

(Iq)

wherein:

R independently represents a hydrogen atom, a $(C_1$-$C_3)$ alkoxy group or a $(C_1$-$C_3)$fluoroalkoxy group, R" is as defined above and is advantageously a hydrogen atom, n is as defined above and is advantageously 1, n' is as defined above and is advantageously 1, R' is a hydrogen atom or a group chosen among a —$NR_1R_2$ group, a N-methylpiperazinyl group, a $(C_1$-$C_3)$alkoxy group and a morpholino group, $R_1$ and $R_2$ are independently a hydrogen atom or a $(C_1$-$C_3)$alkyl group, or one of its pharmaceutically acceptable salt, for use as an agent for preventing, inhibiting or treating cancer.

In one aspect, the compounds described herein include a compound of formula (Ir)

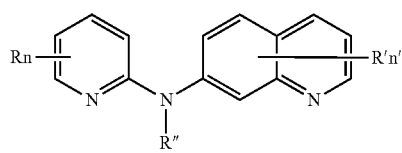

(Ir)

wherein:

R independently represents a hydrogen atom or a $(C_1$-$C_3)$ alkyl group,

R" is as defined above and is advantageously a hydrogen atom, n is as defined above and is advantageously 1, n' is as defined above and is advantageously 1, R' is a hydrogen atom or a group chosen among a —$NR_1R_2$ group, a morpholino group and a $(C_1$-$C_3)$ alkoxy group, $R_1$ and $R_2$ are independently a hydrogen atom or a $(C_1$-$C_3)$alkyl group, or one of its pharmaceutically acceptable salt, for use as an agent for preventing, inhibiting or treating cancer.

In one aspect, the compounds described herein include a compound of formula (Iee)

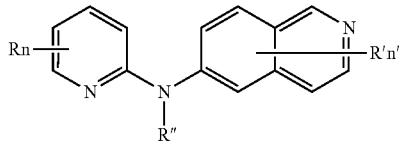

(Iee)

wherein:

R independently represents a hydrogen atom, a $(C_1$-$C_3)$ alkyl group or a $(C_1$-$C_3)$fluoroalkyl group, R" is as defined above and is advantageously a hydrogen atom, n is as defined above and is advantageously 1, n' is as defined above and is advantageously 2, R' is a hydrogen atom or a $(C_1$-$C_3)$alkyl group, or one of its pharmaceutically acceptable salt, for use as an agent for preventing, inhibiting or treating cancer.

Among the previous defined families of compounds of formulae (Ia) to (Iee), some are more particularly preferred for their use as an agent for preventing, inhibiting or treating cancer. These preferred compounds particularly belong to formulae (Ia), (Ie), (Iq) and (Iee), as defined above or one of its pharmaceutically acceptable salts.

Accordingly, the portions below further relate to a compound chosen among compounds of formulae (Ia), (Ie), (Iq) and (Iee), and their pharmaceutically acceptable salts for use as an agent for preventing, inhibiting or treating cancer.

In certain aspects, the compounds described herein include a compound of formula (Ia)

wherein:

R independently represents a hydrogen atom, a halogen atom or a group chosen among a $(C_1$-$C_3)$alkyl group, a —CN group, a —$COOR_1$ group and a $(C_1$-$C_3)$fluoroalkyl group, R" is as defined above and more preferably is a hydrogen atom, $R_1$ is as defined above, n is as defined above, n' is as defined above, R' is a halogen atom, a $(C_1$-$C_4)$alkyl group, a $(C_1$-$C_4)$ alkoxy group or a —$NO_2$ group, or one of its pharmaceutically acceptable salt, for use as an agent for preventing, inhibiting or treating cancer.

In certain aspects, the compounds described herein include a compound of formula (Ie) wherein:

R represents a hydrogen atom or a $(C_1$-$C_4)$alkyl group,

R" is as defined above and more preferably is a hydrogen atom, n is as defined above, n' is as defined above, R' is a halogen atom, or one of its pharmaceutically acceptable salt, for use as an agent for preventing, inhibiting or treating cancer.

In certain aspects, the compounds described herein include a compound of formula (Iq)

wherein:

R', R", n and n' are as defined in formula (I), and

R is a $(C_1$-$C_3)$fluoroalkoxy group, or one of its pharmaceutically acceptable salt, for use as an agent for preventing, inhibiting or treating cancer.

In certain aspects, the compounds described herein include a compound of formula (Iee) wherein:
R is independently a hydrogen atom or a $(C_1-C_4)$alkyl group,
R', R", n and n' are as defined in formula (I),
or one of its pharmaceutically acceptable salt,
for use as an agent for preventing, inhibiting or treating cancer.

In certain aspects, the compounds described herein include a compound of formula (Ia) or (Ie) as defined above or one of its pharmaceutically acceptable salts, for use as an agent for preventing, inhibiting or treating cancer.

According to a preferred embodiment, the compounds described herein for use as an agent for preventing, inhibiting or treating cancer, is chosen from:

(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-aine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N,1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N, 1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine

(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine
(112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N,1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine and their pharmaceutically acceptable salts.

Among the compounds described above, compounds (6), (18), (30), (35), (36), (37), (45), (48), (51), (52), (53), (55), (56), (58), (61), (63), (64), (109), (110), (112), (143), (144) and (148) are of particular interest.

As discussed above, the compounds described herein include compound (6), (18), (30), (35), (36), (37), (45), (48), (51), (52), (53), (55), (56), (58), (61), (63), (64), (109), (110), (112), (143), (144) and (148) or one of its pharmaceutically acceptable salts for use as an agent for preventing, inhibiting or treating cancer.

The compounds of formulae (I), (Ia), (Ib), (Ic), (Id), (Ie), (If), (Ig), (Ih), (Ii), (Ij), (Ik), (Il), (Im), (Io), (Ip), (Iq), (Ir) and (Iee) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compound of formula (I) and the derivatives thereof can include their pharmaceutically acceptable salts, which include hydrobromide, tartrate, citrate, trifluoroacetate, ascorbate, hydrochloride, tartrate, triflate, maleate, mesylate, formate, acetate and fumarate.

In certain aspects, the compounds described herein includes compounds of formula (Ig)
wherein:
R independently represent a hydrogen atom, a halogen atom or a group chosen among a $(C_1-C_3)$alkyl group, a —CN group, a hydroxyl group, a —COOR$_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, with the proviso that R and R' are not simultaneously a hydrogen atom, and when n and n' are 1 and R is a hydrogen atom then R' is not a —COOH group, or anyone of its pharmaceutically acceptable salt.

In certain aspects, the compounds described herein includes compounds of formula (If)

wherein:

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, or anyone of its pharmaceutically acceptable salt.

In certain aspects, the compounds described herein includes compounds of formula (Ih)

wherein:

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, or anyone of its pharmaceutically acceptable salt.

In certain aspects, the compounds described herein includes compounds of formula (Il)

wherein:

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, with the proviso that R and R' are not simultaneously a hydrogen atom, or anyone of its pharmaceutically acceptable salt.

In certain aspects, the compounds described herein includes compounds of formula (Im)

wherein:

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, with the proviso that when n and n' are 1 and R is a hydrogen atom, R' is not a chlorine atom, or anyone of its pharmaceutically acceptable salt.

For simplification, the following compounds and their corresponding definitions are called "new compounds".

In certain aspects, the compounds described herein includes compounds of formula (Ia), as such

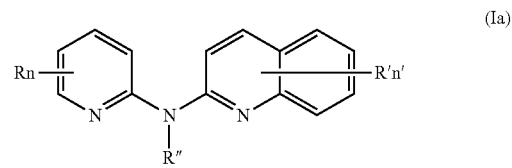

(Ia)

wherein:

R" and n are as defined in formula (Ia), n' is 1,

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a —$NO_2$ group, a ($C_1$-$C_3$)fluoroalkoxy group and a ($C_1$-$C_3$)alkoxy group, R' is a hydrogen atom or a halogen atom or a group chosen among a ($C_1$-$C_3$)alkyl group, a —$COOR_1$ group, and a —CN group, $R_1$ is a hydrogen atom or a ($C_1$-$C_3$)alkyl group:

with the proviso that when R and R' are not simultaneously a hydrogen atom, when n is 1, R is not a methyl group in the ortho or para positions with respect to Z, Z being N, when R' is a hydrogen atom, R is not a bromine atom or a chlorine atom, when R is a hydrogen atom, R' is not a methyl or ethyl group, a —COOH group, a $COOC_2H_5$ group or a bromine atom, said bromine atom being in the ortho position with respect to the bond linked to NR", or one of its pharmaceutically acceptable salt.

Still according to this particular embodiment, the present invention more particularly focuses on compounds of formula (Ia), as such, wherein, R independently represents a hydrogen atom or a $(C_1-C_3)$ alkyl group,
R" is as defined in formula (Ia),
R' is a hydrogen atom, a halogen atom, a $(C_1-C_3)$alkoxy group or a —$NO_2$ group,
n' is 1,
n is 1,
with the proviso that
when n is 1, R is not a methyl group in the ortho or para positions with respect to Z, Z being N,
or one of its pharmaceutically acceptable salt.

In this aspect the compounds described herein can include compounds of formula (Ia'), as such,

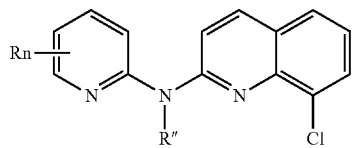

(Ia')

wherein,
R independently represents a hydrogen atom, a $(C_1-C_3)$ alkyl group, a $(C_1-C_3)$fluoroalkyl group, a halogen atom or a hydroxyl group,
R" is as defined in formula (Ia),
n is 1 or 2,
or one of its pharmaceutically acceptable salt.

In certain aspects, the compounds described herein includes compounds of formula (Ie)

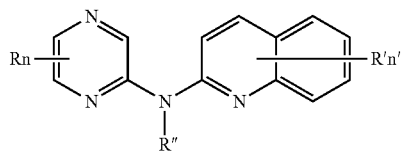

(Ie)

wherein:
R, R', R" n and n' are as defined in formula (I),
with the proviso that
when R is a hydrogen atom, R' is not a bromine atom,
or one of its pharmaceutically acceptable salt.

The compounds described herein further relate to a compound of formula (Iq) as defined above, as such

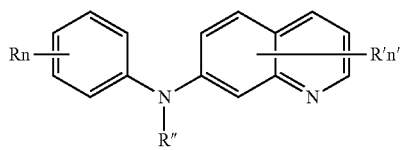

(Iq)

wherein:
R, R', R" and n' are as defined in formula (I),
n is 1 or 2,
with the proviso that
R' and R are not simultaneously a hydrogen atom, when R' is a hydrogen atom, R is not a —$NO_2$ group or a —$NH_2$ group,
when n is 2 and R' is a hydrogen atom, R is not a $COOC_2H_5$ group or a chlorine atom,
or one of its pharmaceutically acceptable salt.

Still according to this particular embodiment, the compounds described herein include compounds of formula (Iq), as such, wherein
R', R", n and n' are as defined in formula (I), and
R is a $(C_1-C_3)$fluoroalkoxy group,
or one of its pharmaceutically acceptable salt.

Still according to this particular embodiment, the compounds described herein include compounds of formula (Iq), as such, wherein
R, R", n and n' are as defined in formula (I), and
R' is a —$NR_1R_2$ group,
$R_1$ and $R_2$ are independently a hydrogen atom or a $(C_1-C_3)$alkyl group,
or one of its pharmaceutically acceptable salt.

Still according to this particular embodiment, the compounds described herein include compounds of formula (Iq), as such, wherein
R, R", n and n' are as defined in formula (I), and
R' is a morpholinyl group, a morpholino group or a N-methylpiperazinyl group,
or one of its pharmaceutically acceptable salt.

In a further aspect, the compounds described herein includes a compound of formula (Iee) as defined above, as such

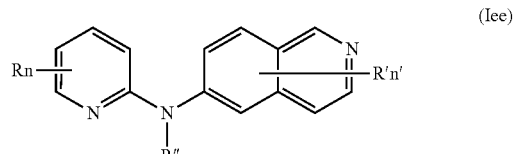

(Iee)

wherein:
R, R', R", n and n' are as defined in formula (I),
or one of its pharmaceutically acceptable salt,
with the exclusion of the following compound

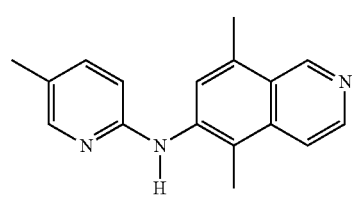

(148)

and with the exclusion of compounds wherein R is a —$NO_2$ group or a —$NH_2$ group when R' is a hydrogen or a methyl group.

Still according to this particular embodiment, the compounds described herein include compounds of formula (Iee), as such, wherein
R', R", n and n' are as defined in formula (I), and
R is a $(C_1-C_3)$fluoroalkyl group,
or one of its pharmaceutically acceptable salt.

Among the compounds discussed above, compounds (1), (2), (5)-(8), (10)-(16), (18), (21)-(44), (46)-(75), (77)-(84), (86)-(119), (121), (124)-(130), (132), (135)-(141), (143)-

(147), (149)-(168) and their pharmaceutically acceptable salts are of particular interest.

As discussed above, the compounds described herein include compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts, as such.

More preferably, compounds (143), (144), (149), (166), (167) and their pharmaceutically acceptable salts are of particular interest.

For example, the compounds described herein can include compounds (143), (144), (149), (166), (167) and their pharmaceutically acceptable salts, where the pharmaceutically acceptable salts include, but are not limited to, hydrobromide, tartrate, citrate, trifluoroacetate, ascorbate, hydrochloride, tartrate, triflate, maleate, mesylate, formate, acetate and fumarate.

In certain aspects, the compounds described herein include compounds (143) and (144) and their pharmaceutically acceptable salts, which include, but are not limited to, hydrobromide, tartrate, citrate, trifluoroacetate, ascorbate, hydrochloride, tartrate, triflate, maleate, mesylate, formate, acetate and fumarate.

The compounds described herein, e.g. compounds of formulae (Ia), (Ie), (Iq) and (Iee) and the specific compounds as listed above, are not only useful as agent for inhibiting, preventing or treating cancer but can also be useful for inhibiting, preventing or treating premature aging or progeria and for inhibiting, preventing or treating AIDS.

According to an aspect of the invention, the compounds may be useful to inhibit, prevent and/or treat diseases with premature aging and that are likely related to aberrant splicing of the nuclear lamin A gene. For example, such diseases may include Hutchinson Guilford Progeria Syndrome (HGPS), progeria, premature aging associated with HIV infection, muscular dystrophy, Charcot-Marie-Tooth disorder, Werner syndrome, but the diseases may also include atherosclerosis, insulin resistant type II diabetes, cataracts, osteoporosis and aging of the skin such as restrictive dermopathy.

The compounds described herein can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

Scheme 1

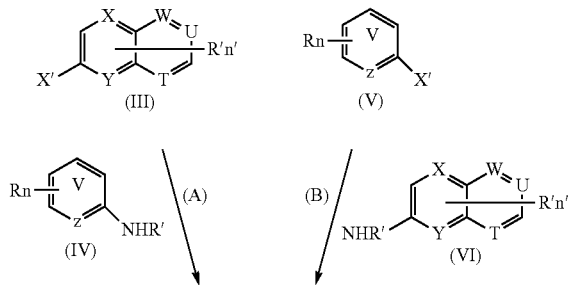

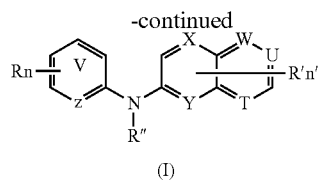

As appears in the scheme, two routes are available for recovering a compound of formula (I) according to the present invention.

The synthesis is based on a coupling reaction alternatively starting from a halogeno-bicycle of formula (III), wherein X, Y, W, T, U, n', R' and R" are as defined above and X' is a chlorine atom or a bromine atom or from a chloro-monocycle of formula (V), wherein Z, V, n and R are as defined above and X' is a chlorine atom or a bromine atom.

According to route (A), the compound of formula (III) is placed in a protic solvent such as tert-butanol. The compound of formula (IV) is then added in a molar ratio ranging from 1 to 1.5 with respect to the compound of formula (III) in presence of an inorganic base, such as $Cs_2CO_3$ or $K_2CO_3$ in a molar ratio ranging from 1 and 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (III), and in the presence of a catalyst, such as $Pd(OAc)_2$ or $Pd_2dba_3$ in an amount ranging from 2 mol % to 10 mol % relative to the total amount of compound of formula (III). The reaction mixture can then be heated at a temperature ranging from 80 to 120° C., for example at 90° C. and stirred for a time ranging form 15 to 25 hours, for example during 20 hours under inert gas and for example argon. The reaction mixture can be concentrated under reduced pressure.

According to route (B) the compound of formula (V) is placed in a protic solvent such as tert-butanol. The compound of formula (VI) is then added in a molar ratio ranging from 1 to 1.5 with respect to the compound of formula (V) in presence of an inorganic base, such as $Cs_2CO_3$ or $K_2CO_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (V), and in the presence of a catalyst, such as $Pd(OAc)_2$ or $Pd_2dba_3$ in an amount ranging from 2 mol % to 10 mol % relative to the total amount of compound of formula (V). The reaction mixture can then be heated at a temperature ranging from 80 to 120° C., for example at 90° C. and stirred for a time ranging form 15 to 25 hours, for example during 20 hours under inert gas and for example argon. The reaction mixture can be concentrated under reduced pressure.

The starting compounds of formula (III), (IV), (V) and (VI) are commercially available or can be prepared according to methods known to the person skilled in the art. The chemical structures and spectroscopic data of some compounds of formula (I) are illustrated respectively in the following Table I and Table II.

TABLE I
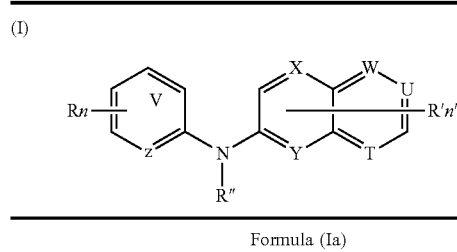
Formula (Ia)
1
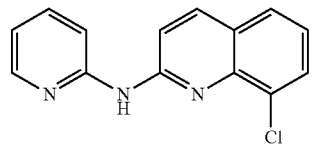 [SMILES: Clc1cccc2ccc(Nc3ccccn3)nc12]
2
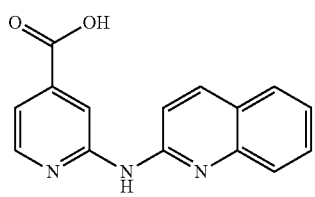 [SMILES: O=C(O)c1ccnc(Nc2ccc3ccccc3n2)c1]
3
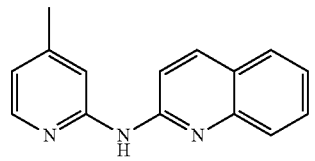 [SMILES: Cc1ccnc(Nc2ccc3ccccc3n2)c1]
4
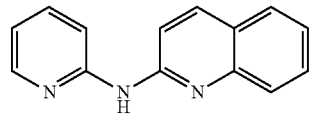 [SMILES: c1ccc(Nc2ccc3ccccc3n2)nc1]
5
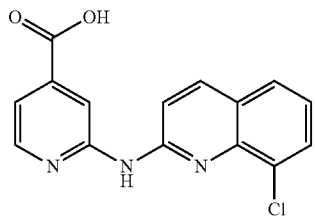 [SMILES: O=C(O)c1ccnc(Nc2ccc3cccc(Cl)c3n2)c1]
6
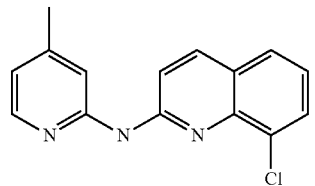 [SMILES: Cc1ccnc(Nc2ccc3cccc(Cl)c3n2)c1]
7
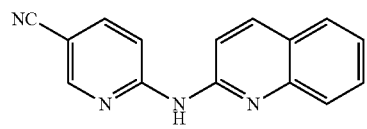 [SMILES: N#Cc1ccc(Nc2ccc3ccccc3n2)nc1]
17
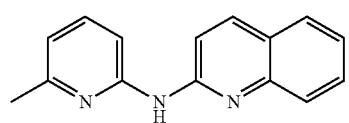 [SMILES: Cc1cccc(Nc2ccc3ccccc3n2)n1]
TABLE I-continued
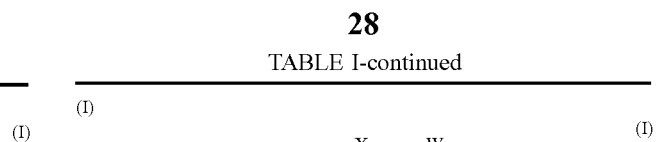
18
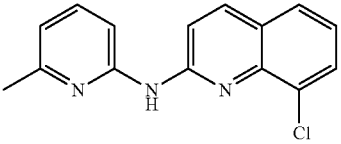 [SMILES: Cc1cccc(Nc2ccc3cccc(Cl)c3n2)n1]
19
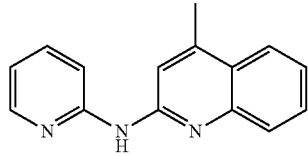 [SMILES: Cc1cc(Nc2ccccn2)nc2ccccc12]
20
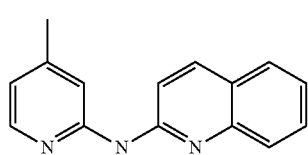
21
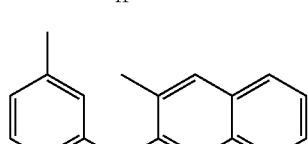
22
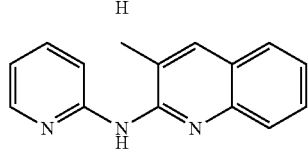
23
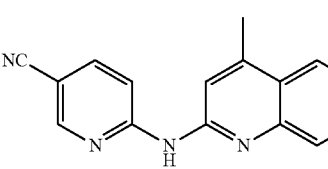
24
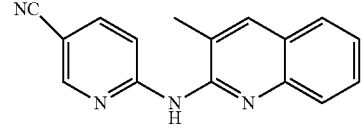 [SMILES: Cc1cc2ccccc2nc1Nc1ccc(C#N)cn1]
25
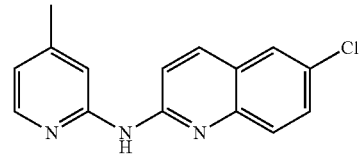 [SMILES: Cc1ccnc(Nc2ccc3cc(Cl)ccc3n2)c1]
26
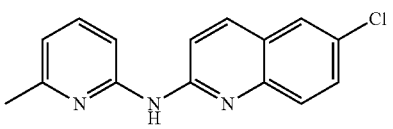 [SMILES: Cc1cccc(Nc2ccc3cc(Cl)ccc3n2)n1]

TABLE I-continued
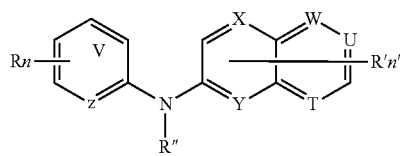
| | |
|---|---|
| 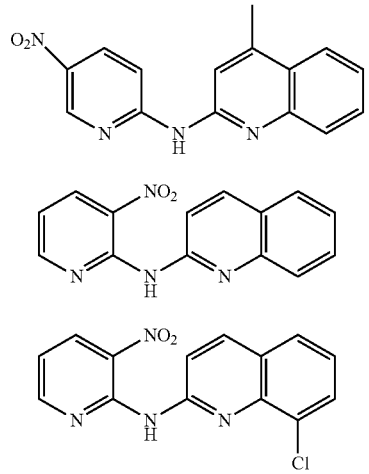 | 27 28 29 30 31 32 33 34 35 |
TABLE I-continued
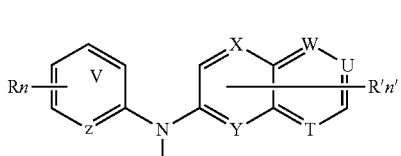
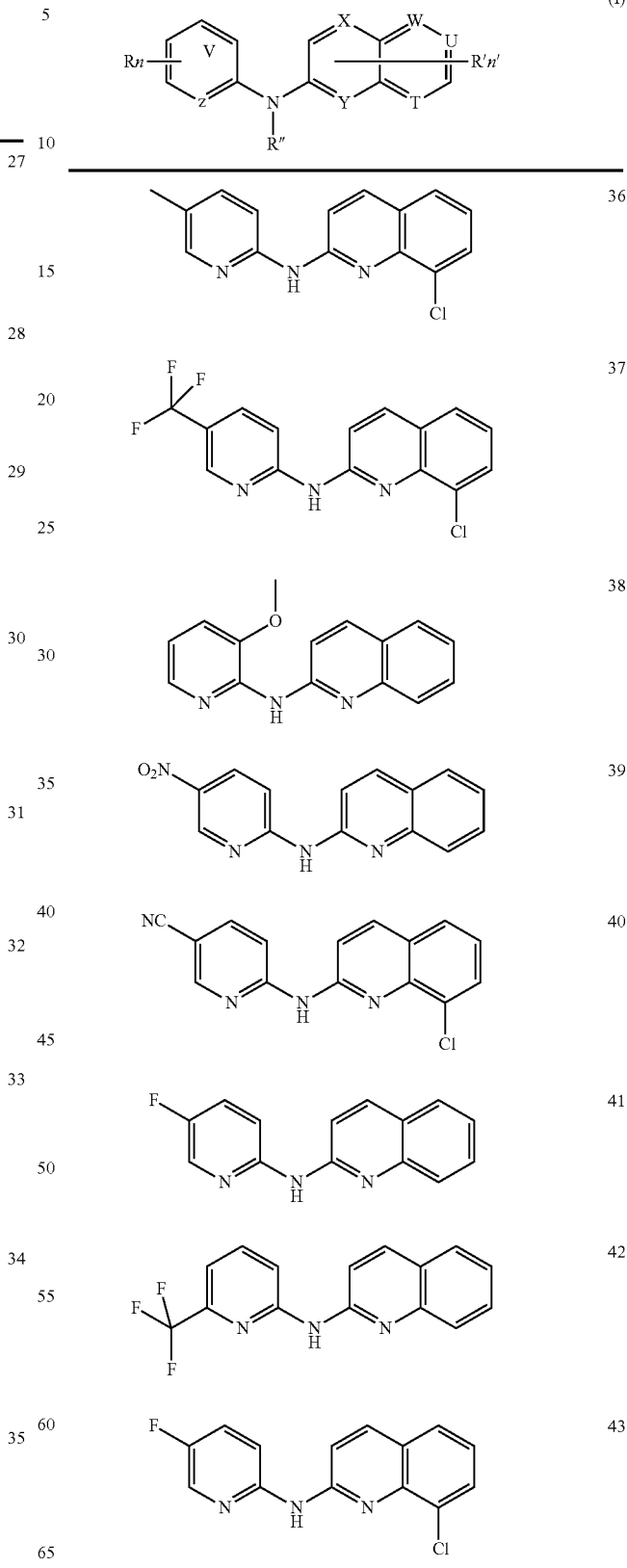

TABLE I-continued
(I)
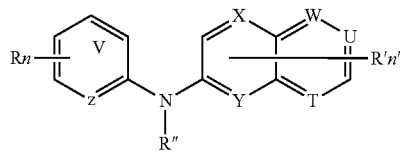
| | |
|---|---|
| 44 | 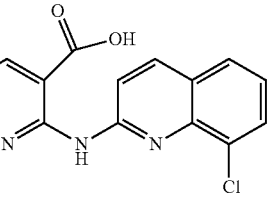 |
| 45 | 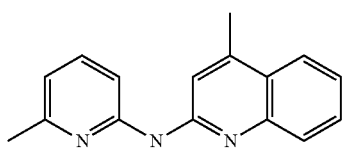 [SMILES: Cc1cccc(Nc2cc(C)c3ccccc3n2)n1] |
| 46 | 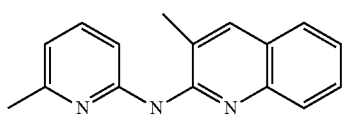 [SMILES: Cc1cccc(Nc2nc3ccccc3cc2C)n1] |
| 47 | 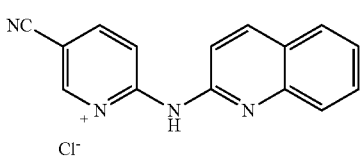 |
| 48 | 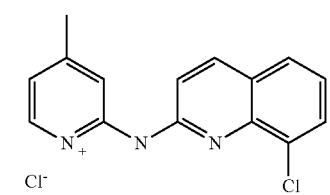 |
| 49 | 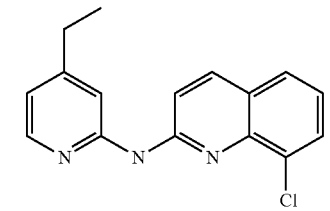 [SMILES: CCc1ccnc(Nc2ccc3cccc(Cl)c3n2)c1] |
| 50 | 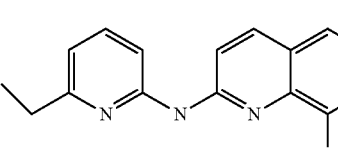 |
| 51 | 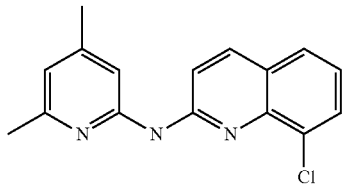 [SMILES: Cc1cc(C)nc(Nc2ccc3cccc(Cl)c3n2)c1] |
TABLE I-continued
(I)
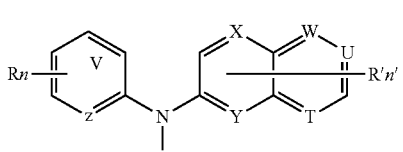
| | |
|---|---|
| 52 | 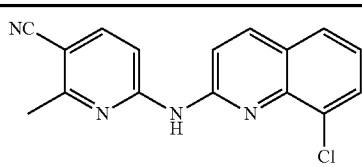 |
| 53 | 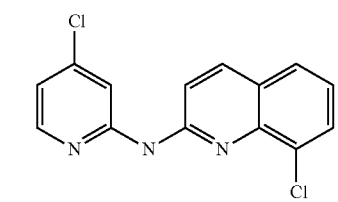 [SMILES: Clc1ccnc(Nc2ccc3cccc(Cl)c3n2)c1] |
| 54 | 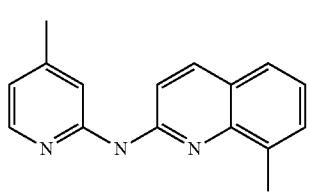 [SMILES: Cc1ccnc(Nc2ccc3cccc(C)c3n2)c1] |
| 55 | 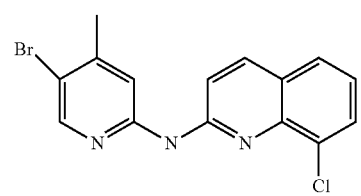 [SMILES: Cc1cc(Nc2ccc3cccc(Cl)c3n2)ncc1Br] |
| 56 | 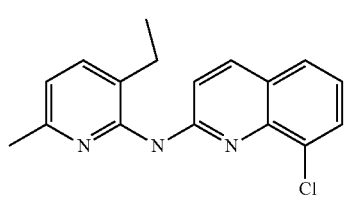 [SMILES: CCc1ccc(C)nc1Nc1ccc2cccc(Cl)c2n1] |
| 57 | 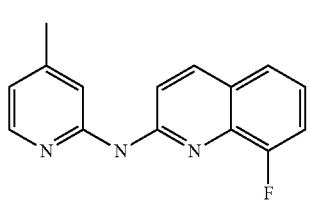 [SMILES: Cc1ccnc(Nc2ccc3cccc(F)c3n2)c1] |
| 58 | 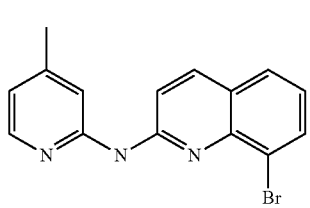 [SMILES: Cc1ccnc(Nc2ccc3cccc(Br)c3n2)c1] |

TABLE I-continued
(I)
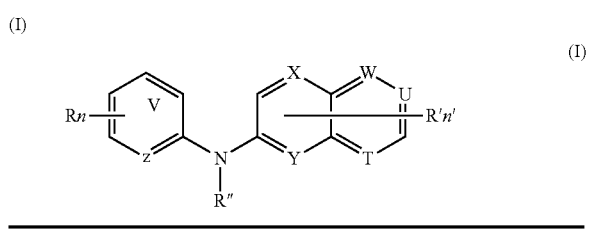
| | |
|---|---|
| 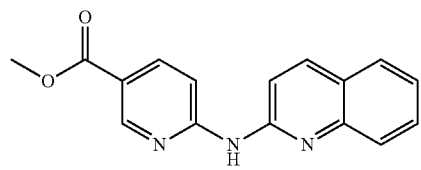 [SMILES: COC(=O)c1ccc(Nc2ccc3ccccc3n2)nc1] | 59 |
| 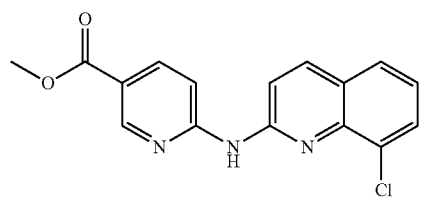 [SMILES: COC(=O)c1ccc(Nc2ccc3cccc(Cl)c3n2)nc1] | 60 |
| 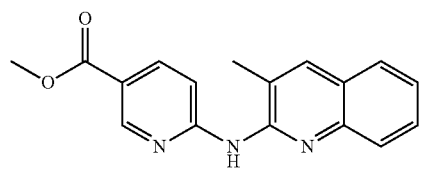 [SMILES: COC(=O)c1ccc(Nc2nc3ccccc3cc2C)nc1] | 61 |
| 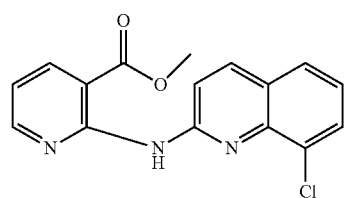 [SMILES: COC(=O)c1cccnc1Nc1ccc2cccc(Cl)c2n1] | 62 |
| 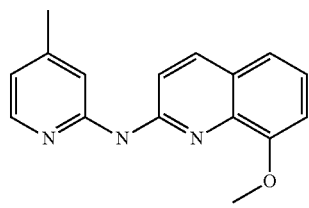 [SMILES: COc1cccc2ccc(Nc3cc(C)ccn3)nc12] | 63 |
| 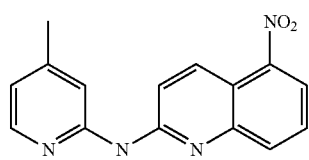 [SMILES: Cc1ccnc(Nc2ccc3c([N+](=O)[O-])cccc3n2)c1] | 64 |
| 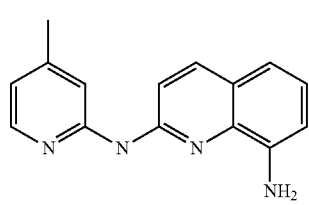 [SMILES: Cc1ccnc(Nc2ccc3cccc([N+](=O)[O-])c3n2)c1] | 65 |
TABLE I-continued
(I)
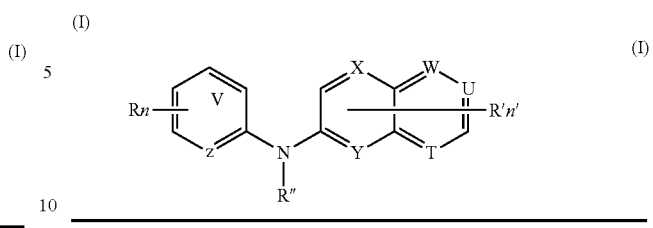
| | |
|---|---|
| 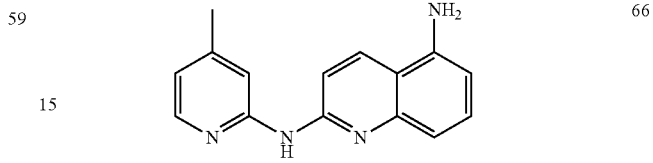 | 66 |
| 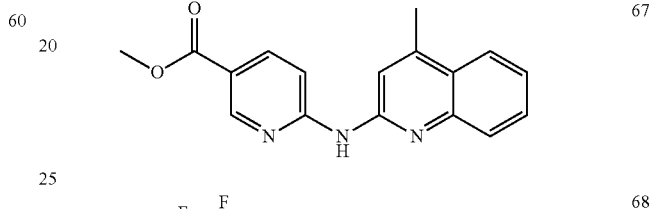 | 67 |
| 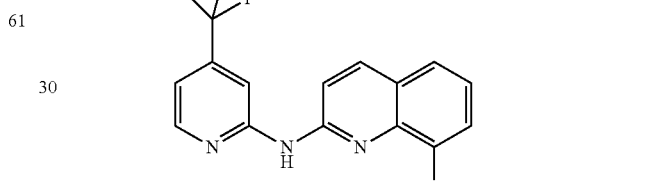 | 68 |
| 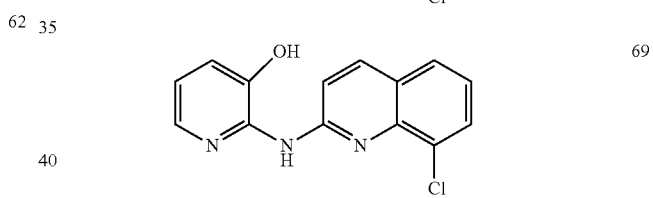 | 69 |
| 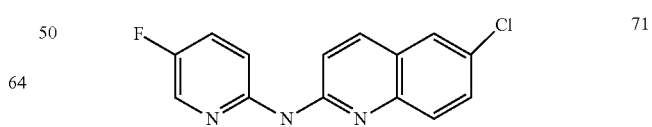 | 70 |
| 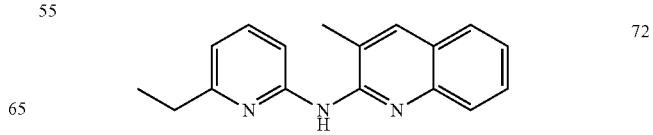 | 71 |
| 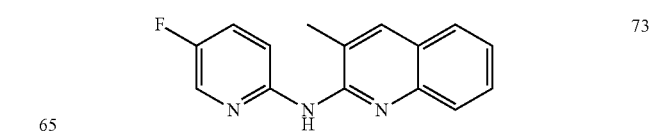 | 72 |

TABLE I-continued
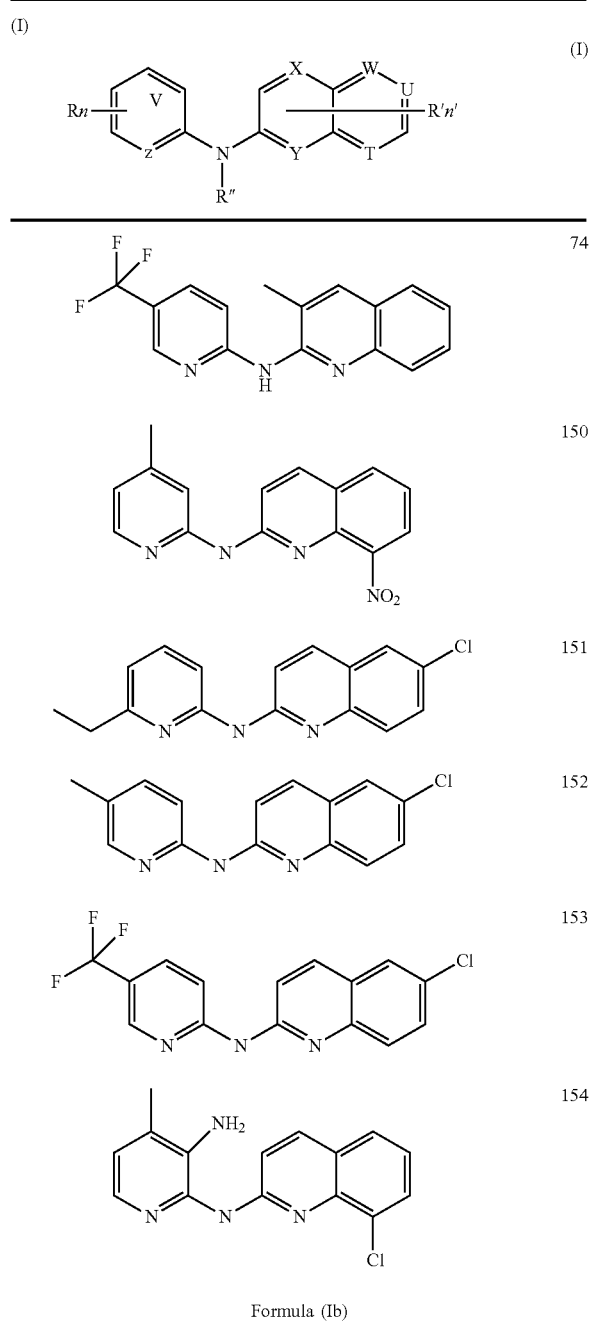
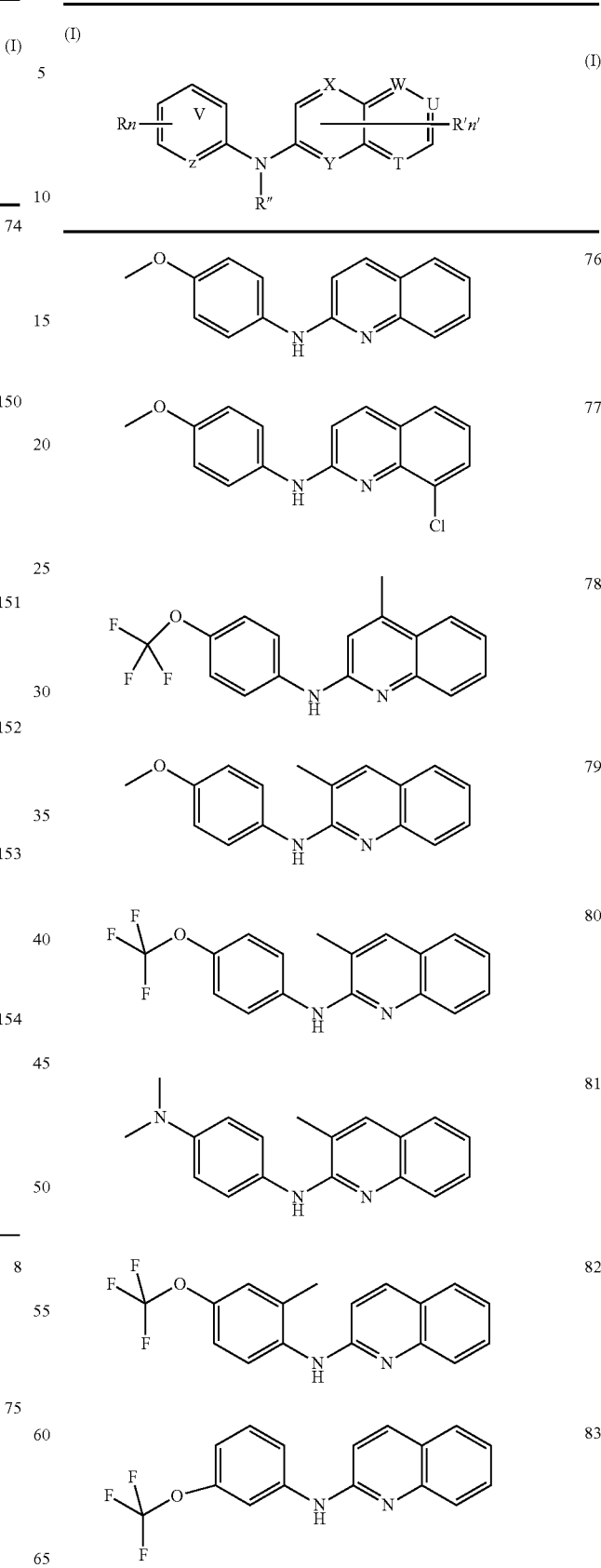

TABLE I-continued
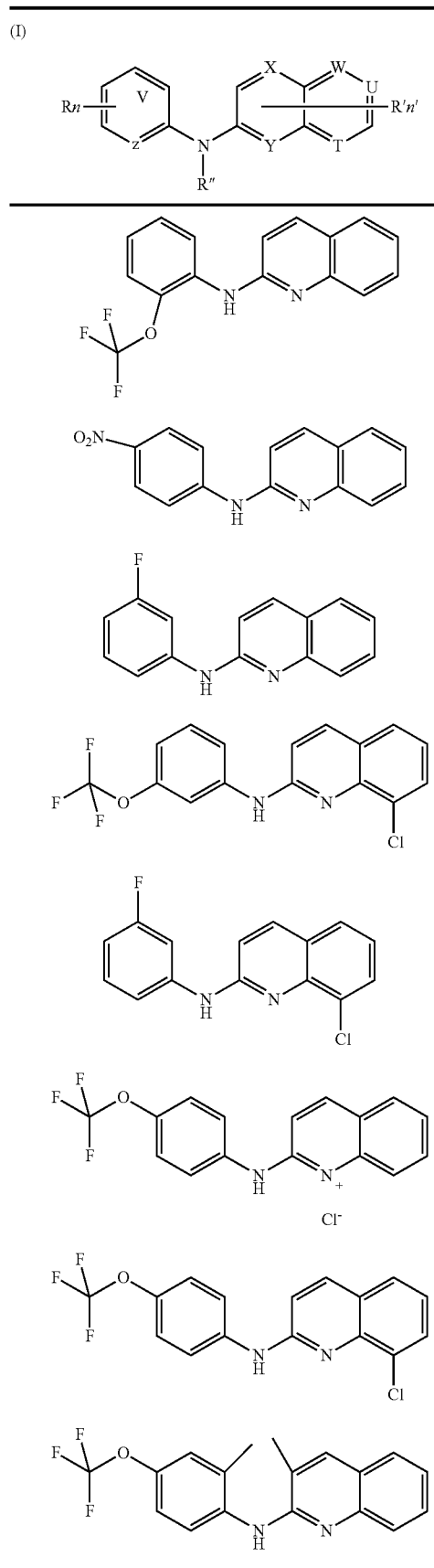
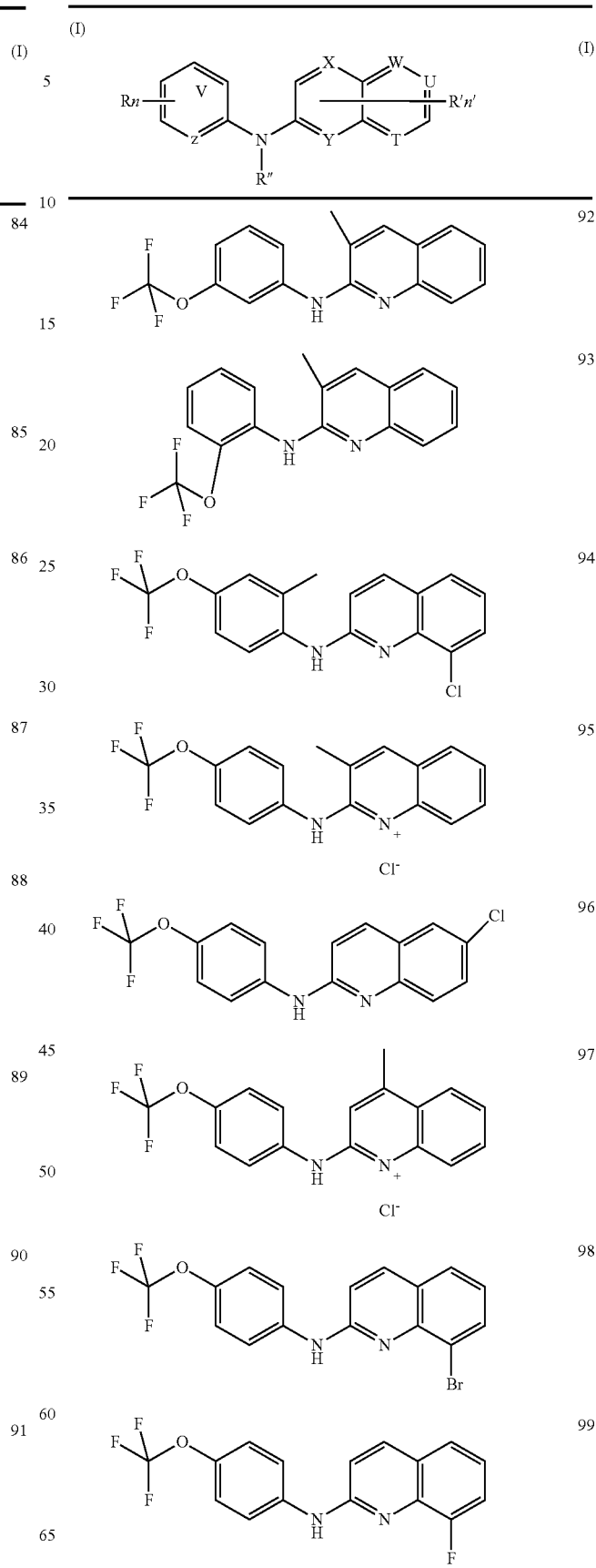

TABLE I-continued
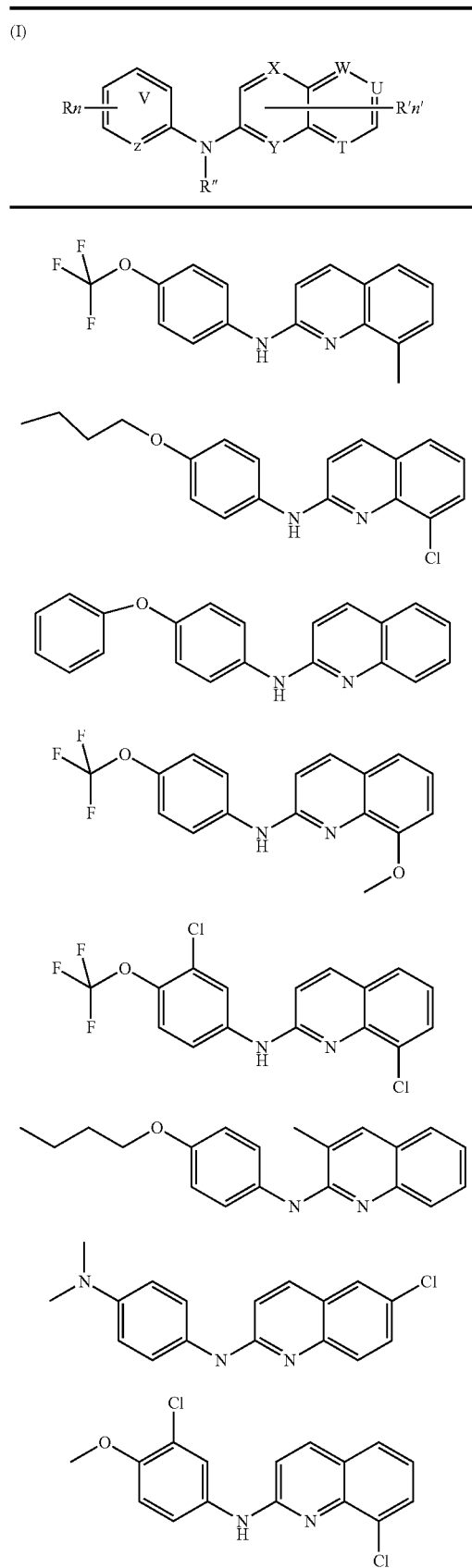
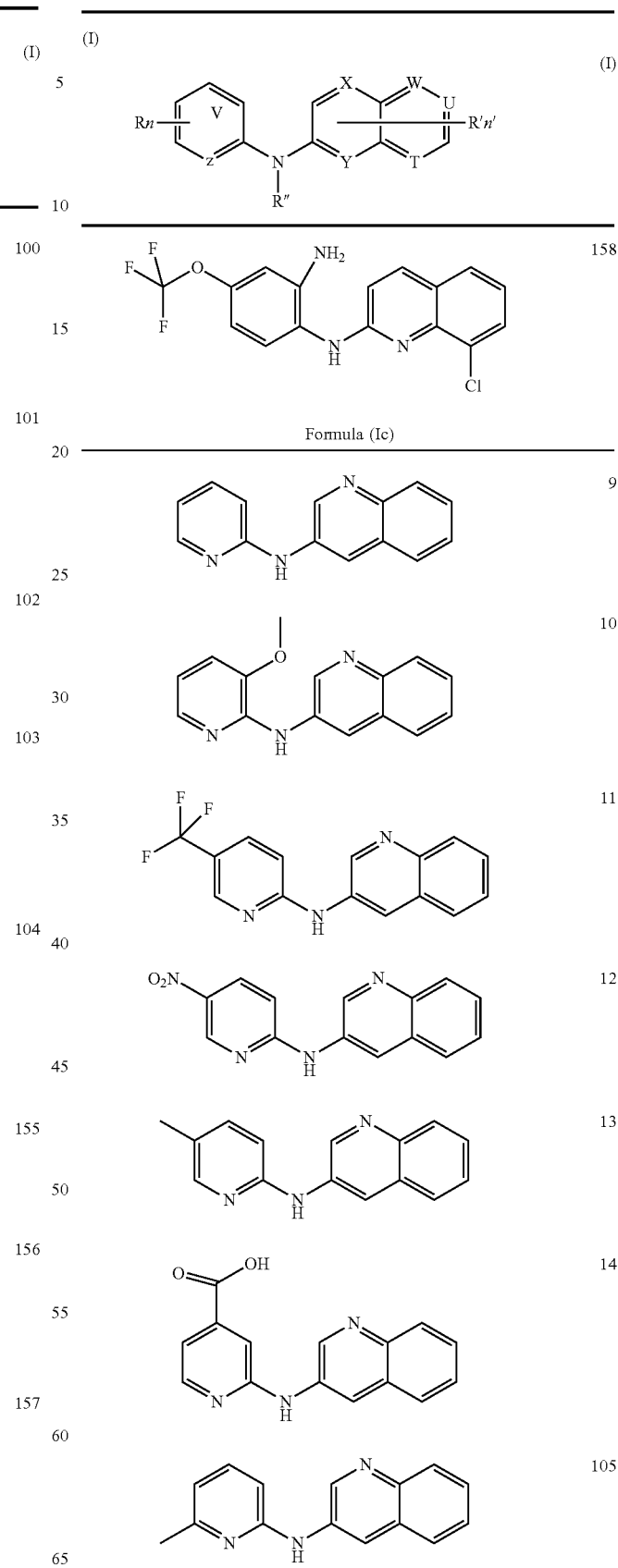

TABLE I-continued
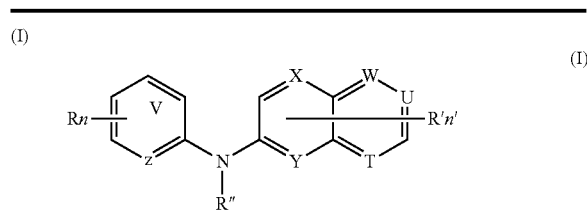
| | |
|---|---|
| 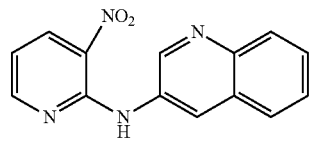 [SMILES: O=[N+]([O-])c1cccnc1Nc1cnc2ccccc2c1] | 106 |
| 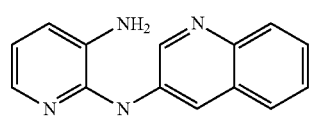 [SMILES: Nc1cccnc1Nc1cnc2ccccc2c1] | 159 |
Formula (Id)
| | |
|---|---|
| 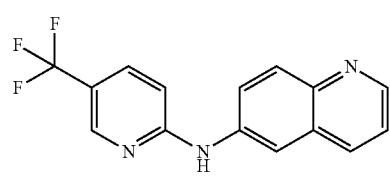 [SMILES: FC(F)(F)c1ccc(Nc2ccc3ncccc3c2)nc1] | 15 |
| 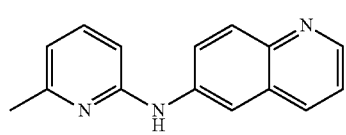 [SMILES: Cc1cccc(Nc2ccc3ncccc3c2)n1] | 16 |
| 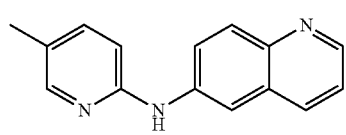 [SMILES: Cc1ccc(Nc2ccc3ncccc3c2)nc1] | 107 |
| 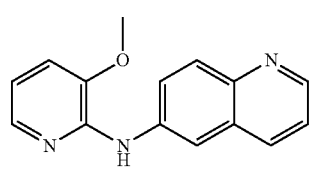 [SMILES: COc1cccnc1Nc1ccc2ncccc2c1] | 108 |
Formula (Ie)
| | |
|---|---|
| 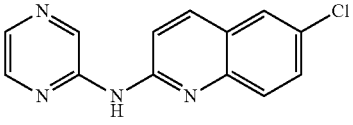 [SMILES: Clc1ccc2nc(Nc3cnccn3)ccc2c1] | 109 |
| 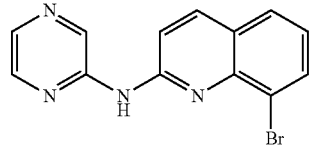 [SMILES: Brc1cccc2ccc(Nc3cnccn3)nc12] | 110 |
| 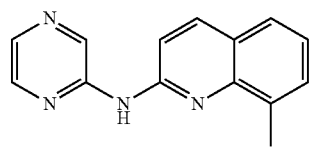 [SMILES: Cc1cccc2ccc(Nc3cnccn3)nc12] | 111 |
TABLE I-continued
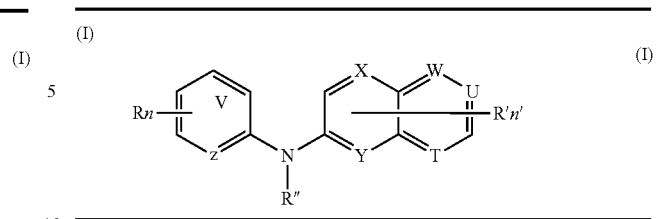
| | |
|---|---|
|  | 112 |
| 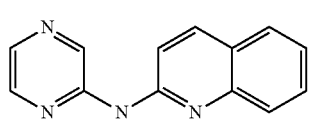 | 113 |
| 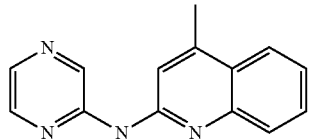 | 114 |
| 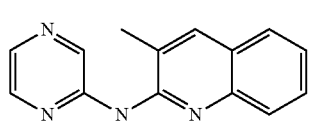 | 115 |
| 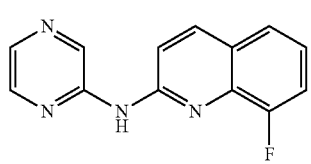 [SMILES: Fc1cccc2ccc(Nc3cnccn3)nc12] | 116 |
| 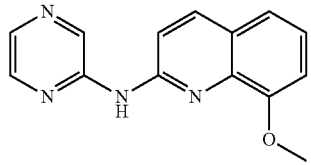 [SMILES: COc1cccc2ccc(Nc3cnccn3)nc12] | 117 |
Formula (If)
| | |
|---|---|
| 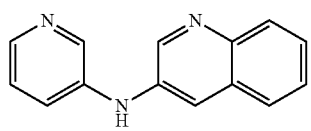 [SMILES: c1cncc(Nc2cnc3ccccc3c2)c1] | 118 |
Formula (Ig)
| | |
|---|---|
| 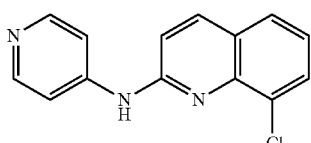 | 119 |
| 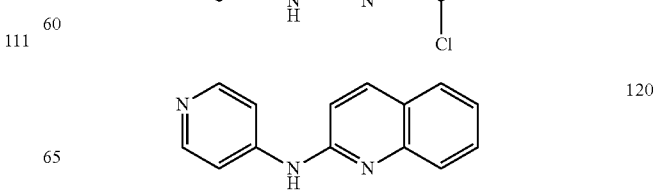 | 120 |

TABLE I-continued (I)

| | |
|---|---|
| Formula (Ih) | 121 |
| Formula (Ii) | 122 |
| | 123 |
| Formula (Ij) | 124 |
| | 125 |
| | 126 |
| | 127 |
| Formula (Ik) | 128 |
| | 129 |
| | 130 |
| Formula (Il) | 131 |
| Formula (Im) | 132 |
| Formula (Io) | 135 |
| | 136 |
| | 137 |
| | 138 |

TABLE I-continued
(I)
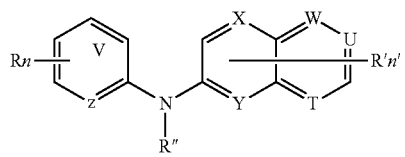
| | |
|---|---|
| 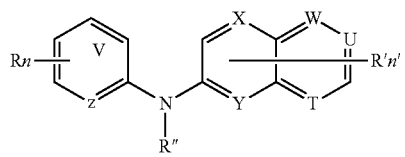 | 139 |
|  | 140 |
| 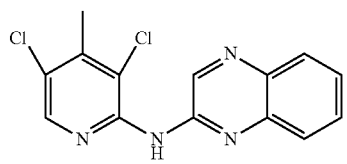 [SMILES: Cc1c(Cl)cnc(Nc2cnc3ccccc3n2)c1Cl] | 141 |
| 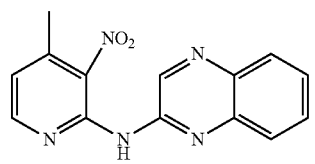 [SMILES: Cc1ccnc(Nc2cnc3ccccc3n2)c1[N+](=O)[O-]] | 160 |
| 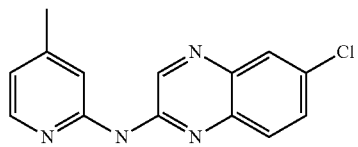 [SMILES: Cc1ccnc(Nc2cnc3cc(Cl)ccc3n2)c1] | 161 |
| 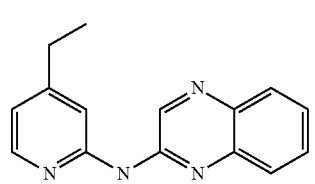 [SMILES: CCc1ccnc(Nc2cnc3ccccc3n2)c1] | 162 |
| 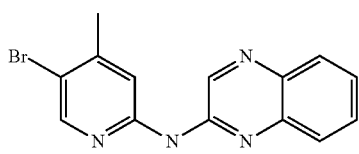 [SMILES: Cc1cc(Nc2cnc3ccccc3n2)ncc1Br] | 163 |
| 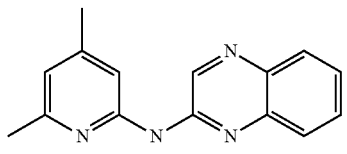 [SMILES: Cc1cc(C)nc(Nc2cnc3ccccc3n2)c1] | 164 |
TABLE I-continued
(I)
| | |
|---|---|
| 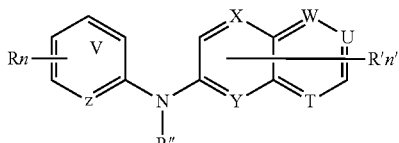 | 165 |
| Formula (Ip) | |
| 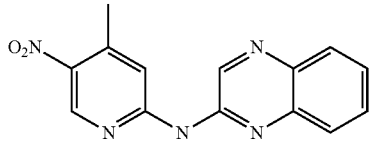 [SMILES: Cc1cc(Nc2cnc3ccccc3n2)ncc1[N+](=O)[O-]] | 142 |
| Formula (Iq) | |
| 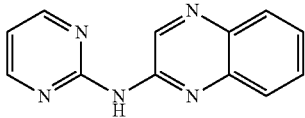 [SMILES: c1cnc(Nc2cnc3ccccc3n2)nc1] | 143 |
| 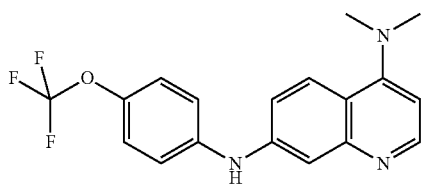 [SMILES: CN(C)c1ccnc2cc(Nc3ccc(OC(F)(F)F)cc3)ccc12] | 144 |
| 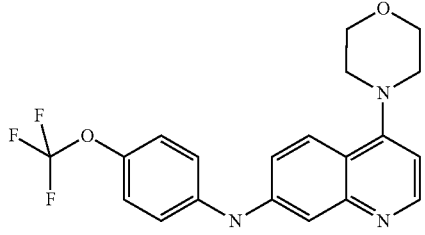 [SMILES: FC(F)(F)Oc1ccc(Nc2ccc3c(N4CCOCC4)ccnc3c2)cc1] | 166 |
| 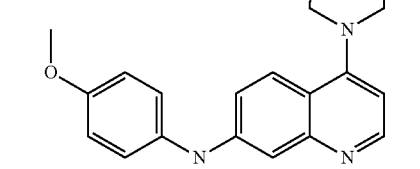 | 167 |

TABLE I-continued

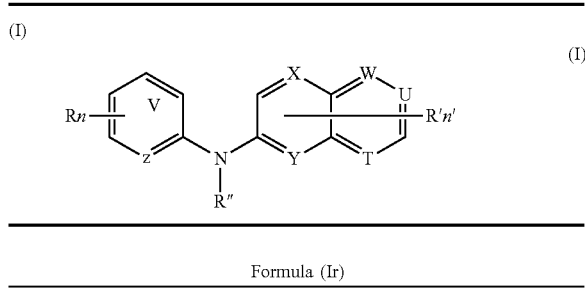

Formula (Ir)

| | |
|---|---|
| 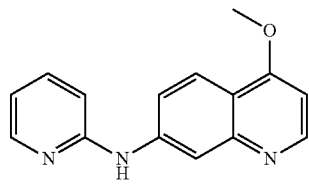 [SMILES: COc1ccnc2cc(Nc3ccccn3)ccc12] | 145 |
| 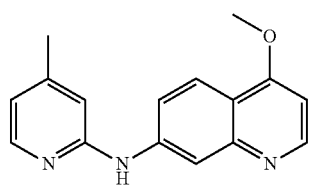 [SMILES: COc1ccnc2cc(Nc3cc(C)ccn3)ccc12] | 146 |
| 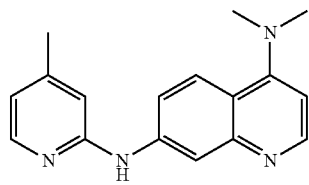 [SMILES: Cc1ccnc(Nc2ccc3c(N(C)C)ccnc3c2)c1] | 147 |

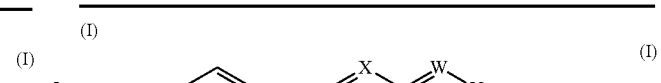

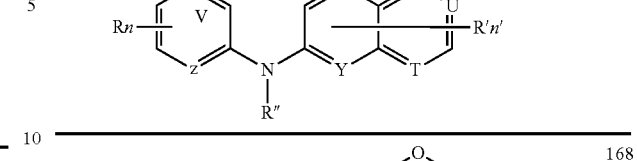

168

Formula (Iee)

| | |
|---|---|
| 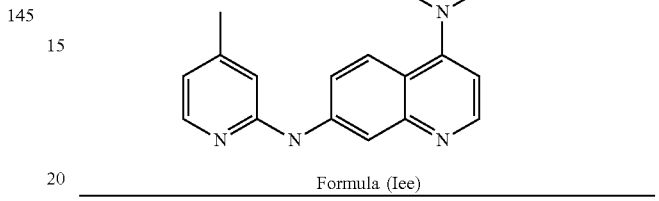 | 148 |
| 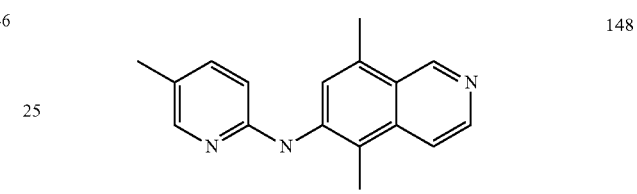 | 149 |

TABLE II

| Ex | Characterizations |
|---|---|
| 1 | MS (ESI) [M + H]⁺ = 256 |
| 2 | $^1$H NMR (300 MHz, D$_2$O) δ 8.31 (d, H = 5.1, 1H). 8.21 (d, 7 = 9.3, 1H). 7.60 (d. J = 7.5, 3H), 7.34 (dd, J = 6.2, 15.6, 2H), 7.18(s, 1H), 6.99 (d, J = 9.1, 1H)<br>MS (ESI) [M + H]⁺ = 266 |
| 5 | MS (ESI) [M + H]⁺ = 300 |
| 6 | $^1$H NMR (300 MHz, DMSO) δ 10.23 (s, 1H). 8.96 (s, 1H), 8.18 (d. 7 = 8.8. 2H),7.78 (dd, 7 = 7.7, 13.7, 2H), 7.46 (d, 7 = 8.9. 1H), 7.31 (t, 7 = 7.8, 1H), 6.86 (d, J = 4.3, 1H), 2.37 (s, 3H).<br>$^{13}$C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24.<br>MS (ESI) (M + H)⁺ = 270 |
| 7 | $^1$H NMR (300 MHz, DMSO) δ 10.71 (s, 1H), 8.71 (d, J = 1.4. 1H), 8.62 (d, J = 8.9, 1H), 8.24 (d, J = 8.9. 1H), 8.17 (dd, J = 1.9. 8.9. 1H), 7.89-7.74 (m, 2H), 7.66 (dd, J = 7.9. 14.2, 2H), 7.42 (t, J = 7.3, 1H).<br>$^{13}$C NMR (75 MHz, DMSO) δ 156.09, 152.40. 152.11, 146.24, 141.07, 137.83, 129.87, 127.67, 126.78, 124.50, 124.21, 118.04, 114.49, 111.67, 100.12.<br>MS (ESI) (M+H)⁺ = 247 |
| 8 | $^1$H NMR (300 MHz, CDCl$_3$) δ 7.92 (d, J = 8.9, 1H). 7.79 (d, J = 8.4, 1H). 7.65 (t, J = 7.7, 3H), 7.59 (dd, J = 7.1, 8.3, 1H), 7.31 (t, J = 7.0. 1H), 7.20 (d, J = 8.5, 2H), 6.88 (d, J = 8.9, 1H), 6.80 (s, 1H)<br>$^{13}$C NMR (75 MHz, CDCl$_3$) δ 153.88, 147.62, 144.35, 139.26, 138.11, 130.13. 127.65, 127.12, 124.43, 123.70, 122.20, 120.95, 112.25.<br>MS (ESI) [M + H]⁺ = 305 |
| 10 | $^1$H NMR (300 MHz, CDCl$_3$,) δ 9.10 (d, J = 2.5, 1H). 8.83 (d, J = 2.6, 1H). 8.02 (d, J = 7.9, 1H), 7.94 (dd, J = 1.3, 5.0. 1H), 7.85-7.79 (m, 1H), 7.52 ( pd, J = 1.5. 6.9. 2H), 7.33 (s, 1H), 7.04 (dd, J = 1.2, 7.9, 1H), 6.81 (dd, J = 5.1, 7.9, 1H), 3.95 (s, 3H) |
| 11 | MS (ESI) [M + H]⁺ = 290 |
| 12 | $^1$H NMR (300 MHz, CDCl$_3$) δ 9.18 (d, J = 2.7, 1H), 8.86 (d, J = 2.5, 1H), 8.56 (d, J = 2.3, 1H), 8.33 (dd, J = 2.7, 9.2, 1H), 8.08 (d, J = 8.5, 1H), 7.83 (d, J = 8.5, 1H), 7.71-7.63 (m, 2H), 7.57 (t, J = 7.4, 2H), 6.82 (d, J = 9.1. 1H) |

TABLE II-continued

| Ex | Characterizations |
|---|---|
| 13 | $^1$H NMR (300 MHz, CDCl$_3$) δ 8.83 (d, J = 2.6. 1H), 8.37 (d, J = 2.3. 1H), 8.00 (d, J = 8.2. 1H), 7.71 (d, J = 7.7. 1H), 7.59-7.51 (m, 1H), 7.46 (dd, J = 7.3, 15.1, 2H), 6.71 (d, J = 8.3, 1H), 6.67 (d, J = 7.4, 1H), 2.49 (s, 3H). <br> $^{13}$C NMR (75 MHz, CDCl$_3$) δ 157.13, 154.59, 145.81, 144.43, 138.78, 134.54, 129.22, 128.86, 127.41, 127.27, 121.48, 115.41, 106.50, 24.18. <br> MS (ESI) [M + H]$^+$ = 236 |
| 14 | MS (ESI) [M + H]$^+$ = 266 |
| 15 | MS (ESI) [M + H]$^+$ = 290 |
| 16 | $^1$H NMR (300 MHZ, CDCl$^3$) δ 8.77 (dd. J = 1.5, 4.2, 1H), 8.04 (dd, J = 4.7, 8.7, 2H), 7.92 (d, J = 2.4, 1H), 7.59 (dd, J = 2.5, 9.1, 1 H), 7.47 (t, J = 7.8, 1H), 7.35 (dd, J = 4.2, 8.3, 1H), 6.87 (s, 1H), 6.81 (d, J = 8.2. 1H), 6.70 (d, J = 7.4, 1H), 2.50 (s, 3H) <br> MS (ESI) [M + H]$^+$ = 236 |
| 18 | $^1$H NMR (300 MHz, CDCl$_3$, δ 8.53 (d, J = 59.9. 2H), 7.76 (d, J = 8.6, 1H), 7.58 (t, J = 8.3, 2H), 7.42 (d, J = 7.8, 1H), 7.09 (t, J = 7.7, 1H), 6.95 (d, J = 8.7, 1H), 6.71 (d, J = 7.3, 1H), 2.38 (s, 3H) |
| 21 | $^1$H NMR (300 MHz, CDCl$_3$) δ 8.78 (s, 1H), 8.13 (d, J = 5.1, 1H), 7.89 (d, J = 8.3. 1H), 7.79 (s, 1H), 7.63 (d, J = 8.0. 1H), 7.56 (d, J = 7.3, 1H), 7.38 (s, 1H), 7.33 (1.7 = 7.5, 1H), 6.79 (d, J = 4.9, 1H), 2.44 (s, 6H) |
| 22 | $^1$H NMR (300 MHz, CDCl$_3$) δ 8.95 (d, J = 8.4, 1H), 8.28 (d, J = 5.7, 1H), 7.87 (d, J = 8.3, 1H), 7.78 (s, 1H), 7.76-7.70 (m, 1H), 7.62 (d, J = 8.0, 1H), 7.60-7.52 (m, 1H), 7.42 (s, 1H), 7.32 (t, J = 7.4. 1H), 6.95 (dd, J = 5.1, 6.5, 2H), 2.45 (s, 3H) |
| 23 | $^1$H NMR (300 MHz, CDCl$_3$) δ 8.64 (d, J = 8.4, 1H), 8.55 (d, J = 2.1, 1H), 8.03 (s, 1H), 7.90 (d, J = 8.5, 4H), 7.66 (t, J = 7.6. 1H), 7.44 (t, J = 7.6, 1H), 7.06 (s, 1H), 2.67 (s, 4H) |
| 24 | $^1$H NMR (300 MHz, CDCl$_3$) δ 9.09 (d, 7 = 8.9, 1H). 8.53 (d, J = 1.7, 1H), 7.94 (dd, J = 2.2. 8.9, 1H), 7.92-7.84 (m, 2H), 7.67 (d, J = 8.6. 2H), 7.65-7.58 (m, 1H), 7.40 (1.7 = 7, 1H), 2.49 (s, 3H) |
| 25 | $^1$H NMR (300 MHz, CDCl$_3$) δ 8.16 (d, J = 5.2, 1H), 8.10 (s, 1H). 7.90 (d, J = 8.8, 1H), 7.79 (d, J = 9.0, 1H), 7.66 (d, J = 2.2, 1H), 7.55 (dd, J = 2.3, 8.9, 1H), 7.39 (d, J = 9.0, 1H), 6.79 (d, 7 = 5.2. 1H), 2.42 (s, 3H) <br> MS (ESI) [M + H]$^+$ = 270 |
| 26 | $^1$H NMR (300 MHz, CDCl$_3$) δ 8.06 (d, J = 8.3, 1H), 7.70 (d, J = 9.0, 1H), 7.64 (d, 7 = 8.9, 1H), 7.49 (t, J = 7.9, 2H), 7.40 (dd, J = 2.3, 8.9, 1H), 7.18 (d, J = 8.9, 1H), 6.68 (d, 7 = 7.4, 1H), 2.38 (s, 3H) <br> MS (ESI) [M + H]$^+$ = 270 |
| 27 | $^1$H NMR (300 MHz, CDCl$_3$) δ 9.17 (d, J = 2.5, 1H), 8.71 (s, 1H), 8.49 (dd, J = 2.6, 9.0, 1H), 7.99 (s, 1H), 7.93 (d, J = 8.9, 2H), 7.74-7.64 (m, 1H), 7.48 (dd, J = 4.2, 11.4, 1H), 7.09 (s, 1H), 2.71 (s, 3H) |
| 28 | $^1$H NMR (300 MHz, CDCl$_3$) δ 8.64-8.51 (m, 3H), 8.18 (d, J = 9.0. 1H), 7.93 (d, J = 8.4, 1H), 7.79 (d, 7 = 8.1, 1H), 7.73-7.64 (m, 1H), 7.51-7.41 (m, 1H), 7.00 (dd, J = 4.6, 8.2. 1H), 6.75 (dd, J = 4.6, 8.3, 0H) |
| 29 | $^1$H NMR (300 MHz, CDCl$_3$) δ 10.77 (s, 1H), 8.60 (s, 3H), 8.19 (d, J = 8.2. 1H), 7.76 (dd, J = 6.6, 25.5, 2H), 7.38 (d, J = 7.2, 1H), 7.04 (d, J = 4.4, 1H) |
| 30 | $^1$H NMR (300 MHz, CDCl$_3$, δ 8.46 (dd, J = 1.9, 5.0. 1H), 7.87 (dd, J = 2.0, 7.6, 1H). 7.82 (d, 7 = 7.3, 1H), 7.60 (t, J = 7.3, 2H), 7.43-7.33 (m, 1H), 6.90 (dd, J = 5.0, 7.6, 1H), 2.64 (s, 3H) |
| 31 | $^1$H NMR (300 MHz, CDCl3) δ 8.44 (d, J = 9.1, 1H), 8.1 7 (d, J = 4.8, 1H). 8.03 (d, J = 9.1, 1H), 7.78 (d, J = 8.4, 1H), 7.68 (d, J = 8.0. 1H), 7.62-7.54 (m, 1H), 7.39 (d, J = 7.3, 1H), 7.32 (t, J = 7.5, 1H), 6.82 (dd, J= 5.0, 7.3, 1H), 2.31 (s, 3H) <br> MS (ESI) [M + H]$^+$ = 236_ |
| 32 | $^1$H NMR (300 MHz, CDCl$_3$) δ 8.23 (d, J = 8.5, 1H), 8.10 (s, 1H), 7.91 (d, J = 8.9, 1H), 7.82 (d, J = 8.4, 1H), 7.62 (d. J = 8.3, 1H), 7.56 (d, J = 7.3, 1H), 7.50 (dd, J = 1.8, 8.5, 1H), 7.37-7.24 (m, 2H), 2.26 (s, 3H) <br> MS (ESI) [M + H]$^+$ = 236 |
| 33 | $^1$H NMR (300 MHz, CDCl$_3$ δ 8.87 (s, 1H), 8.32 (d, J = 5.0, 1H), 7.95 (d, J = 8.8, 1H), 7.84 (d, J = 8.3, 1H), 7.60 (dd, J = 7.4, 14.1, 2H), 7.32 (t, J = 7.5, 1H), 7.04 (dd, J = 5.0, 9.0, 2H) <br> MS (ESI) [M + H]$^+$ = 247 |
| 34 | $^1$H NMR (300 MHz, CDCl$_3$) δ 8.52 (s, 1H), 8.45 (d, J = 8.6, 1H), 8.01 (d, J = 8.8, 1H), 7.87 (dd, J = 2.5, 8.5, 2H), 7.72-7.56 (m, 2H), 7.39 (d, J = 9.0, 2H) <br> MS (ESI) [M + H]$^+$ = 290 |
| 35 | $^1$H NMR (300 MHz, CDCl$_3$) δ 8.32 (d, J = 9.1, 1H), 8.07 (d, J = 4.8, 1H), 7.93 (d, J = 9.1, 1H), 7.59 (t, J = 7.9, 1H), 7.52 (d, J = 8.0, 1H), 7.36 (d, J = 7.2, 1H), 7.14 (1, J = 7.8. 1H), 6.77 (dd, J = 5.0, 7.3, 1H), 2.29 (s, 3H) <br> MS (ESI) [M + H]$^+$ = 270 |
| 36 | $^1$H NMR (300 MHz, CDCl$_3$, δ 8.70 (d, J = 1.2, 1H), 8.01 (s, 1H), 7.82 (d, 7 = 8.9, 1H), 7.62 (d, 7 = 7.6, 1H), 7.53 (dd, J = 1.8, 8.6, 1H), 7.46 (d, J = 7.9, 1H), 7.12 (t, J = 7.8, 1H), 7.05 (d, J = 8.8, 1H), 2.21 (s, 3H) <br> MS (ESI) [M + H]$^+$ = 270_ |
| 37 | $^1$H NMR (300 MHz, CDCl$_3$) δ 9.08 (d, J = 8.5, 1H), 8.55 (s, 1H), 8.36 (s, 1H), 8.02 (d, J = 8.1, 2H), 7.77 (d, J = 7.2, 1H), 7.62 (d, J = 7.6, 1H), 7.35-7.24 (m, 1H), 7.12 (d, J = 8.8, 1H) <br> MS (ESI) [M + H]$^+$ = 324 |
| 38 | $^1$H NMR (300 MHz, CDCl$_3$) δ 8.69 (d, J = 9.1, 1H), 7.97 (d, 7 = 9.1, 1H), 7.80-7.74 (m, 1H), 7.70 (d, J = 8.4, 1H), 7.59 (d, J = 8.0, 1H), 7.54-7.45 (m, 1H), 7.22 (t, J = 7.5, 1H), 6.87 (d, J = 7.9, 1H), 6.68 (dd, 7 = 5.0, 7.9, 1H), 3.73 (s, 3H) <br> MS (ESI) [M + H]$^+$ = 252 |

TABLE II-continued

| Ex | Characterizations |
|---|---|
| 39 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 1.3, 1H), 2.73 (dd, J = 7.6, 15.2, 2H), 1.28 (t, J = 7.7, 3H) |
| 40 | $^1$H NMR (300 MHz, DMSO) δ 9.75 (s, 1H), 9.12 (d, J = 2.3, 1H), 8.50 (d, J = 2.2, 1H), 8.48 (s, 1H), 8.13 (s, 1H), 7.83 (s, 1H), 7.80 (s, 1H), 7.64 (t, J = 7.7, 1H), 7.45 (t, J = 7.8, 1H) |
| 41 | $^1$H NMR (300 MHz, CDCl$_3$) δ 8.52 (dd, J = 2.8, 8.6, 1H), 8.35 (s, 1H), 8.15 (d, J = 2.3, 1H), 7.94 (d, J = 8.8, 1H), 7.84 (d, J = 8.2, 1H), 7.65 (d, J = 7.8, 1H), 7.59 (d, J = 7.2, 1H), 7.50-7.40 (m, 1H), 7.33 (t, J = 7.4, 1H), 7.11 (d, J = 8.9, 1H)<br>MS (ESI) [M + H]$^+$ = 240 |
| 42 | $^1$H NMR (300 MHz, CDCl$_3$) δ 8.55 (d, J = 6.8, 1H), 8.01 (d, 7 = 8.9, 2H), 7.82 (dd, J = 9.1, 17.3, 2H), 7.69 (d, 7 = 8.0, 1H), 7.63 (d, J = 7.6, 1H), 7.37 (t, J = 7.5, 1H), 7.32-7.18 (m, 2H) MS (ESI) [M + H]$^+$ = 290 |
| 43 | $^1$H NMR (300 MHz, DMSO) δ 10.41 (s, 1H), 9.08 (dd, J = 4.1, 9.3, 1H), 8.31 (d, J = 2.9, 1H), 8.20 (d, J = 8.9, 1H), 7.88-7.70 (m, 3H), 7.44 (d, J = 8.9, 1H), 7.32 (t, J = 7.8, 1H)<br>$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.<br>MS (ESI) [M+H]$^+$ = 274 |
| 44 | $^1$HNMR (300 MHz, CDCl$_3$) δ 11.09 (s, 1H), 8.78 (d, J = 9.0, 1H), 8.42 (dd, J = 1.9, 4.7, 1H), 8.28 (dd, 7 = 1.9, 7.8, 1H), 8.11 (d, J = 9.1, 1H), 7.73 (d, J = 7.5, 1H), 7.65 (d, J = 8.1, 1H), 7.27 (dd, J = 6.4, 9.2, 1H), 6.88 (d, J = 4.8, 7.8, 1H)<br>MS (ESI) [M + H]$^+$ = 300 |
| 46 | $^1$H NMR (300 MHz, CDCl$_3$) δ 8.59 (d, J = 8.3, 1H), 7.73 (d, J = 8.3, 1H), 7.57 (s, 1H), 7.51 (t, J = 7.9, 1H), 7.43 (t, J = 9.2, 2H), 7.17 (t, J = 7.4, 1H), 6.67 (d, J = 7.4, 1H), 2.36 (s, 3H), 2.28 (s, 3H) |
| 47 | $^1$H NMR (300 MHz, MeOD) δ 8.99 (s, 1H), 8.76 (d, J = 9.2, 1H), 8.32 (d, J = 8.7, 1H), 8.22 (d, J = 8.6, 1H), 8.11 (d, J = 7.8, 1H), 8.01 (t, J = 7.1, 1H), 7.76 (t, J = 7.4, 1H), 7.55-7.43 (m. 2H)<br>MS (ESI) [M + H]$^+$ = 247 |
| 48 | $^1$H NMR (300 MHz, MeOD) δ 8.48 (d, J = 9.1, 1H), 8.40 (d, J = 6.7, 1H), 7.94 (d, J = 8.4, 1H), 7.90 (d, J = 7.8, 1H), 7.54 (t, J = 8.0, 1H), 7.38 (d, J = 8.6, 1H), 7.30 (s, 2H), 2.58 (s, 3H)<br>MS (ESI) [M + H]$^+$ = 270 |
| 49 | $^1$H NMR (300 MHz, CDCl$_3$) δ 9.34 (s, 1H), 8.95 (s, 1H), 8.21 (d, J = 5.1, 1H), 7.87 (d, J = 8.9, 1H), 7.71 (d, J = 7.5, 1H), 7.52 (d, J = 7.9, 1H), 7.19 (t, J = 7.8, 1H), 7.05 (d, J = 8.9, 1H), 6.84 (d, J = 5.1, 1H), 2.76 (q, J = 7.6, 2H), 1.37 (1. J = 7.6, 3H) |
| 50 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 51 | $^1$H NMR (300 MHz, CDCl$_3$) δ 8.64 (s, 1H), 8.06 (s, 1H), 7.89 (d, J = 8.7, 1H), 7.71 (d, 7 = 7.4, 1H). 7.54 (d, J = 7.8, 1H), 7.20 (t, J = 7.7, 1H), 7.02 (d, J = 8.8, 1H), 6.67 (s, 1H), 2.43 (s, 3H), 2.39 (s, 3H)<br>$^{13}$C NMR (75 MHz, CDCl$_3$) δ 156.15, 153.17, 152.82, 150.16, 143.70, 137.92, 131.34, 129.89, 126.49, 125.47, 123.43, 118.62, 114.47, 111.02, 24.13, 21.70.<br>MS (ESI) [M + H]$^+$ = 284 |
| 52 | $^1$H NMR (300 MHz, CDCl$_3$) δ 8.89 (d, j = 8.8, 1H), 8.05 (d, J = 8.8, 1H), 8.01 (s, 1H), 7.93 (d, J = 8.8, 1H), 7.79 (d, J = 7.5, 1H), 7.64 (d, J = 8.0, 1H), 7.32 (t, J = 7.8, 1H), 7.13 (d, J = 8.8, 1H), 2.67 (s, 3H) |
| 53 | $^1$H NMR (300 MHz, CDCl$_3$) δ 9.27 (s, 1H), 833 (d, J = 3.7, 1H), 8.13 (d, J = 5.2, 1H), 8.00 (d, J = 8.8, 1H), 7.76 (d, J = 7.4, 1H), 7.60 (d, J = 8.0, 1H), 7.29 (d, J = 7.9, 1H), 7.07 (d, J = 8.9, 1H), 6.97 (d, 7 = 4.8, 1H) |
| 54 | MS (ESI) [M + H]$^+$ = 250 |
| 55 | $^1$H NMR (300 MHz, CDCl$_3$) δ 8.19 (s, 1H). 7.90 (d, J = 9.0, 1H), 7.63 (d, J = 7.5, 1H), 7.52 (d, H = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.26 (t, J = 7.7, 3H) |
| 56 | $^1$H NMR (300 MHz, CDCl$_3$) δ 8.20 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.25 (dd, J = 7.5, 15.5, 3H) |
| 57 | MS (ESI) [M + H]$^+$ = 253 |
| 58 | MS (ESI) [M + H]$^+$ = 314-316 |
| 59 | $^1$H NMR (300 MHz, CDCl$_3$) δ 8.91 (d, J = 1.7, 1H), 8.46 (d, J = 8.8, 1H), 8.28 (dd, J = 2.0, 8.8, 1H), 8.23 (s, 1H), 8.03 (d, J = 8.8, 1H), 7.88 (d, J = 8.3, 1H), 7.70 (d, 7 = 8.0, 1H), 7.67-7.58 (m, 1H), 7.38 (t, J = 7.4, 1H), 7.32 (d, J = 8.8, 2H), 3.91 (s, 3H) |
| 60 | $^1$H NMR (300 MHz, CDCl$_3$) δ 8.94 (d, J = 8.9, 1H), 8.91 (d, J = 1.8, 1H), 8.37 (dd, J = 2.2, 8.8, 1H), 8.04 (d, 7 = 8.9, 2H), 7.77 (d, J = 7.5, 1H), 7.62 (d, J = 7.2, 1H), 7.30 (t, J = 7.8, 2H), 7.19 (d, J = 8.8, 2H), 3.92 (s, 3H) |
| 61 | $^1$H NMR (300 MHz, CDCl$_3$) δ 8.96 (d, J = 8.8, 1H), 8.85 (d, J = 1.3, 1H), 8.28 (d, J = 9.9, 1H), 7.84 (d, 7=8.0, 1H), 7.77 (s, 1H), 7.65 (s, 1H), 7.59 (d, J = 8.4, 2H), 7.53 (d, J = 8.4, 1H), 7.31 (t, J = 7.4, 1H), 3.88 (s, 4H), 2.42 (s, 4H)<br>MS (ESI) [M + H]$^+$ = 294 |
| 62 | $^1$H NMR (300 MHz, CDCl$_3$) δ 11.02 (s, 1H), 8.75 (d, J = 9.2, 1H), 8.44 (d, J = 3.7, 1H), 8.31 (d, J = 7.9, 1H), 8.10 (d, H = 9.0, 1H), 7.72 (d, 7 = 7.5, 1H), 7.64 (d, J = 8.2, 1H), 7.27 (d, 7 = 8.1, 1H), 6.88 (dd, 7 = 4.7, 7.8, 1H), 3.97 (s, 3H)<br>MS (ESI) [M + H]$^+$ = 314 |
| 63 | MS (ESI) [M + H]$^+$ = 266 |
| 64 | $^1$H NMR (300 MHz, DMSO) δ 10.38 (s, 1H), 8.56 (s, 1H), 8.28 (d, J = 9.1, 1H), 8.20-8.03 (m, 3H), 7.50 (d, J = 8.7, 1H), 7.45 (d, J = 8.0, 1H), 6.88 (d, 7 = 4.4, 1H), 2.37 (s, 3H) |
| 65 | MS (ESI) [M + H]$^+$ = 314-316 |

TABLE II-continued

| Ex | Characterizations |
|---|---|
| 66 | MS (ESI) [M + H]$^+$ = 250 |
| 67 | $^1$H NMR (300 MHz, DMSO) δ 10.51 (s, 1H), 8.83 (d, J = 2.3, 1H), 8.62 (d, J = 9.3, 1H), 8.24 (dd, J = 2.7, 9.1, 1H), 7.96 (d, 7 = 8.9. 1H), 7.81 (d, 7 = 7.8, 1H), 7.67 (t, J = 7.6. 1H). 7.45 (d. J = 11.2. 2H). 3.86 (s, 3H). 2.62 (s, 3H)<br>MS (ESI) [M] + [H]$^+$ = 294 |
| 68 | $^1$H NMR (300 MHz, CDCl$_3$) δ 9.57 (s, 1H), 8.44 (d, J = 4.8, 1H), 8.05 (d, J = 8.8, 1H), 7.86 (s, 1H), 7.80 (d, J = 7.5, 1H), 7.64 (d, J = 8.0, 1H), 7.31 (t, J = 7.8, 1H), 7.19 (d, J = 4.3, 1H), 7.04 (d, H = 8.8, 1H) |
| 69 | 1H NMR (300 MHz. CDC1,) 6 9.12 (s. 1H). 7.94 (d. J = 8.6. IH). 7.71 (d. J = 7.5. 1H), 7.57 (d, J = 7.8, 1H). 7.40 (s, 1H). 7.25 (d, J = 10.2, 2H),7.17(s, 1H). 7.05 (s, 1H) |
| 70 | $^1$H NMR (300 MHz, CDCl$_3$) δ 9.07 (d, J = 8.5, 1H), 7.97 (d, J = 8.8, 1H), 7.90 (t, J = 8.0, 1H), 7.84 (s, 1H), 7.75 (dd, J = 1.1, 7.5, 1H), 7.62-7.55 (m, 1H), 7.31 (d, J = 7.6. 1H), 7.27 (t, J = 7.8, 1H), 7.08 (d, J = 8.8, 1H)<br>MS (ESI) [M + H]$^+$ = 274 |
| 71 | MS (ESI) [M + H]$^+$ = 274 |
| 72 | $^1$H NMR (300 MHz, CDCl$_3$) δ 8.67 (d, J = 7.9. 1H), 7.83 (d, J = 8.3, 1H), 7.71 (s, 1H), 7.69-7.61 (m, 1H), 7.57 (d, J = 7.9, 2H), 7.52 (d, J = 7.1, 1H), 7.28 (t, J = 7.4, 1H), 2.74 (q, J = 7.6, 2H), 2.42 (s, 3H), 1.31 (t, J = 7.6, 3H)<br>MS (ESI) [M + H]$^+$ = 264 |
| 73 | $^1$H NMR (300MHz, CDCl$_3$) δ 8.91 (dd, J = 3.8, 9.0, 1H), 8.11 (d, 7 = 2.9, 1H), 7.81 (d, J = 8.3, 1H), 7.71 (s, 1H), 7.56 (dd, J = 7.4, 14.1, 2H), 7.51-7.42 (m, 1H), 7.29 (d, J = 7.2, 1H), 2.38 (s, 3H)<br>MS (ESI) [M + H]$^+$ = 254 |
| 74 | $^1$H NMR (300 MHz, CDCl$_3$) δ 8.96 (d. J = 8.3, 1H), 8.49 (s, 1H), 7.89 (dd, J = 1.9, 9.0, 1H), 7.82 (d, J = 8.2, 1H), 7.72 (s, 1H), 7.57 (t, J = 8.7, 3H), 7.33 (t, J = 7.4, 1H), 2.37 (s, 3H)<br>MS (ESI) [M + H]$^+$ = 304 |
| 75 | $^1$H NMR (300 MHz, CDCl$_3$) δ 7.83 (d, J = 9.0, 1H), 7.69 (dd, J = 1.3, 7.6, 1H), 7.53 (dd, J = 1.2, 8.0, 1H), 7.42 (d, J = 8.9, 2H), 7.15 (t, 7 = 7.8, 1H), 6.89 (d, J = 8.9, 2H), 6.79 (d, J = 8.9, 2H), 2.97 (s, 6H) |
| 77 | $^1$H NMR (300 MHz, CDCl$_3$) δ 7.83 (d, J = 8.8, 1H), 7.70 (d, J = 7.6, 1H). 7.59 (d. J = 8.6, 2H), 7.52 (d, J = 7.3, 1H), 7.16 (t, J = 7.7, 1H), 6.94 (d, J = 8.4, 3H), 6.86 (d, J = 8.8, 1H), 3.82 (s, 3H)<br>$^{13}$C NMR (75 MHz, CDCl$_3$) δ 156.40, 155.54, 144.29, 138.09, 132.96, 130.44, 129.99, 126.61, 125.22, 123.29, 122.66. 114.73, 112.16, 55.74.<br>MS (ESI) [M + H]$^+$ = 285 |
| 78 | $^1$H NMR (300 MHz, CDCl$_3$) δ 7.80 (t, J = 7.6, 2H), 7.64 (d, J = 8.9, 2H), 7.61-7.55 (m, 1H), 7.33 (t, J = 7.6, 1H), 7.19 (d, J = 8.7, 2H), 2.59 (s, 3H) |
| 79 | $^1$H NMR (300 MHz, CDCl$_3$) δ 7.78 (d, J = 8.4, 1H), 7.76-7.71 (m, 2H), 7.69 (s, 1H), 7.57 (dd, J = 1.1, 8.0, 1H), 7.51 (ddd, 7 = 1.5, 7.0, 8.4, 1H), 7.29-7.21 (m, 1H), 6.96-6.90 (m, 2H), 3.82 (s, 3H), 2.35 (s, 3H) |
| 80 | $^1$H NMR (300 MHz, CDCl$_3$) δ 7.92 (d, J = 8.9 Hz, 2H), 7.84 (d, J = 8.3 Hz, 1H), 7.78 (s, 1H), 7.62 (d, J = 8.0 Hz, 1H), 7.57 (t, J = 7.7 Hz, 1H), 7.32 (t, J = 7.4 Hz, 1H), 7.24 (d, J = 8.7 Hz, 2H). 6.53 (s, 1H), 2.42 (s, 3H)<br>$^{13}$C NMR (75 MHz, CDCl$_3$) δ 152.46, 146.25, 143.86, 139.33, 136.83, 128.93, 126.96, 126.71, 124.75, 123.56, 121.88, 120.44, 119.95, 17.77.<br>MS (ESI) [ M+ H]$^+$ = 319 |
| 81 | $^1$H NMR (300 MHz, CDCl$_3$) δ 7.75 (d, J = 8.3, 1H), 7.66 (d, J = 8.5, 3H), 7.55 (d, J = 7.8, 1H), 7.48 (d, J = 7.6, 1H), 7.20 (d, J = 7.2, 1H), 6.80 (d, J = 8.8, 2H), 6.32 (s, 1H), 2.93 (s, 7H), 2.35 (s, 3H) |
| 82 | $^1$H NMR (300 MHz, CDCl$_3$) δ 7.92 (d, J = 8.9, 1H), 7.82-7.70 (m, 2H), 7.66 (d, 7 = 7.8, 1H), 7.59 (t, J = 7.6, 1H), 7.30 (dd, 7 = 6.0. 13.5, 1H), 7.14 (s, 1H), 7.11 (s, 1H), 6.84 (d, 7 = 8.9, 1H), 2.32 (s, 3H)<br>MS (ESI) [M + H]$^+$ = 319 |
| 83 | $^1$H NMR (300 MHz, CDCl$_3$) δ 7.93-7.86 (m, 1H), 7.85 (s, 1H), 7.82 (d, J = 8.4, 1H), 7.59 (dd, J = 8.2, 15.5, 2H), 7.44-7.38 (m, 1H), 7.29 (dd, J = 8.3, 16.8, 2H), 6.91 (d, J = 9.0, 1H), 6.87 (d, J = 8.3, 1H)<br>MS (ESI) [M + H]$^+$ = 305 |
| 84 | $^1$H NMR (300 MHz, CDCl$_3$) δ 8.67 (d, J = 8.1, 1H), 7.92 (d, J = 8.9, 1H), 7.85 (d, J = 8.4, 1H), 7.63 (d, J = 7.6, 1H), 7.58 (d, J = 7.3, 1H), 7.30 (dd, J = 6.8, 14.8, 3H), 7.02 (t, J = 7.8, 1H), 6.89 (d, J = 8.9, 1H)<br>MS (ESI) [M + H]$^+$ = 305 |
| 86 | $^1$H NMR (300 MHz, CDCl$_3$) δ 7.93 (d, J = 8.9, 1H), 7.83 (d, J = 8.3, 1H), 7.70 (d, J = 12.0. 1H), 7.61 (dd, J = 7.9, 18.1, 2H), 7.32 (d, J = 7.9, 1H), 7.31-7.25 (m, 1H), 7.21 (t, J = 6.5, 1H), 6.92 (d, J = 8.9, 1H), 6.79-6.68 (m, 1H)<br>MS (ESI) [M + H]$^+$ = 2.19 |
| 87 | $^1$H NMR (300 MHz, CDCl$_3$) δ 8.27 (s, 1H), 7.76 (d, 7 = 8.9, 1H), 7.67 (d, 7 = 7.5, 1H), 7.51 (d, 7 = 8.2, 1H), 7.45 (d, 7 = 7.9, 1H), 7.28 (d, J = 8.2, 1H), 7.14 (t, J = 7.8, 1H), 6.86 (d, J = 10.1, 1H), 6.76 (d, J = 8.9, 1H)<br>MS (ESI) [M +H]$^+$ = 339 |
| 88 | $^1$H NMR (300 MHz, CDCl$_3$) δ 8.11 (dt, J = 2.1, 12.1, 1H), 7.76 (d, J = 8.9, 1H), 7.66 (dd, J = 1.2, 7.6. 1H), 7.45 (dd, J = 1.1, 8.0, 1H), 7.22 (dd, J = 1.4, 7.2, 2H), 7.18(d, J = 7.6, 1H), 7.12 (d, 7 = 7.8, 1H), 6.75 (d, J = 8.9, 1H), 6.69 (d, J = 7.9, 1H)<br>MS (ESI) [M + H]$^+$ = 273 |
| 89 | $^1$H NMR (300 MHz, DMSO) δ 11.38 (s, 1H), 8.41 (d, J = 9.1, 1H), 7.93 (d, 7 = 7.8, 1H), 7.80 (dt, J = 8.1, 20.9, 4H), 7.50 (d, J = 7.8, 3H), 7.36 (d, 7 = 9.3, 1H) |
| 90 | $^1$H NMR (300 MHz, CDCl$_3$) δ 7.84 (d, J = 9.1, 2H), 7.79 (d, J = 8.9, 1H), 7.67 (dd, J = 1.2, 7.6, 1H), 7.48 (dd, J = 1.1, 8.0, 1H), 7.18 (s, 3H), 6.89 (s, 1H), 6.75 (d, J = 8.9, 1H) |

TABLE II-continued

| Ex | Characterizations |
|---|---|

¹³C NMR (75 MHz, CDCl₃) δ 153.88, 144.30, 143.91, 139.00, 138.25, 131.13, 130.13, 126.55, 125.42, 123.45, 122.50, 122.17, 120.49, 119.10, 113.24,
MS (ESI) [M + H]⁺ = 339

91 ¹H NMR (300 MHz, CDCl₃) δ 8.74 (s, 1H), 8.54 (s, 1H), 8.46 (d, J = 8.8, 1H), 7.91 (dd, J = 5.5, 14.5, 2H), 7.79 (d, J = 8.9. 1H), 7.67 (d, J = 2.1, 1H), 7.56 (dd, J = 2.3, 8.9, 1H), 7.35 (d, J = 8.9, 1H)

92 ¹H NMR (300 MHz, CDCl₃) δ 8.67 (d, J = 7.9, 1H), 7.83 (d, J = 8.3, 1H), 7.71 (s, 1H), 7.69-7.61 (m, 1H), 7.55 (dd, J = 7.5, 14.4. 2H), 7.29 (d, J = 7.8, 1H), 6.80 (d, J = 7.4, 1H)

93 ¹H NMR (300 MHz, CDCl₃) δ 9.21 (dd, J = 1.5, 8.4, 1H), 7.85 (d, J = 8.4, 1H), 7.73 (s, 1H), 7.58 (d, J = 7.8, 1H), 7.53 (dd, J = 1.3, 8.3, 1H), 7.40-7.35 (m, 1H), 7.32 (dd, J = 1.1, 4.6, 1H), 7.31-7.24 (m, 2H), 7.04 (s, 1H), 7.02-6.94 (m, 1H), 2.38 (s, 3H)

94 ¹H NMR (300 MHz, CDCl₃) δ 8.16 (d, 7 = 8.7, 1H), 7.83 (d, J = 8.9, 1H), 7.63 (d, J = 7.6, 1H), 7.48 (d, J = 8.0, 1H), 7.13 (t, J = 7.8, 1H), 7.08 (s, 1H), 7.04 (s, 2H), 6.81 (d, J = 8.9, 2H), 2.27 (s, 3H)
MS (ESI) [M + H]⁺ = 353

95 ¹H NMR (300 MHz, MeOD) δ 8.42 (s, 1H), 7.94 (d, J = 7.9, 1H), 7.83 (d, J = 8.1, 1H), 7.78 (d, J = 7.1, 1H), 7.72 (d, J = 8.7, 2H), 7.58 (d, J = 8.2, 3H), 2.60 (s, 3H)
MS (ESI) [M + H]⁺ = 319

96 ¹H NMR (300 MHz, CDCl₃) δ 7.79 (d, 7 = 8.9, 1H), 7.70 (d, J = 8.9, 1H), 7.64 (d, 7 = 8.9, 2H), 7.59 (d, J = 2.1, 1H), 7.50 (dd, J = 2.3, 8.9, 1H), 7.19 (d, J = 8.6, 2H), 6.85 (d, 7 = 8.9, 1H)
MS (ESI) [M + H]⁺ = 281

97 ¹H NMR (300 MHz, MeOD) δ 8.11 (d, J = 8.4, 1H), 7.81 (s, 2H), 7.62 (d, J = 8.7, 3H), 7.51 (d, J = 8.3, 2H), 7.12 (s, 1H), 2.77 (s, 3H)
MS (ESI) [M + H]⁺ = 319

98 MS (ESI) [M + H]⁺ = 383-385
99 MS (ESI) [M + H]⁺ = 320
100 MS (ESI) |M + H]⁺ = 316
101 ¹H NMR (300 MHz, CDCl₃) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H)
MS (ESI) [M + H]⁺ = 327

102 ¹H NMR (300 MHz, CDCl₃) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H)
MS (ESI) [M + H]⁺ = 313

103 MS (ESI) [M + H]⁺ = 334
104 ¹H NMR (300 MHz, CDCl₃) δ 8.49 (d, J = 2.5, 1H), 7.89 (d, J = 8.8, 1H), 7.72 (d, J = 7.6, 1H), 7.63 (dd, J = 2.5, 8.9, 1H), 7.53 (d, J = 8.0, 1H), 7.23 (dd, J = 6.2, 14.0, 2H), 7.04 (s, 1H), 6.81 (d, J = 8.8, 1H)
MS (ESI) [M + H]⁺ = 373

105 ¹H NMR (300 MHz, CDCl₃) δ 8.85 (d, J = 2.6, 1H), 8.45 (d, J = 2.3, 1H), 8.01 (d, J = 8.1, 1H), 7.71 (d, J = 7.8, 1H), 7.58 (s, 1H), 7.53 (d, J = 7.6, 1H), 7.51-7.45 (m, 2H), 7.45-7.36 (m, 1H), 6.72-6.62 (m, 2H), 2.48 (s, 3H)
¹³C NMR (75 MHz, CDCl₃) δ 157.18, 154.80, 145.42, 143.80, 138.17, 135.04, 128.88, 128.76, 127.17, 127.04, 120.69, 115.22, 106.73, 24.38

106 ¹H NMR (300 MHz, DMSO) δ 10.24 (s, 1H), 9.06 (d, J = 2.3, 1H), 8.65 (d, J = 1.8, 1H), 8.60 (d, J = 8.3, 1H), 8.56 (d, J = 4.5, 1H), 7.97 (dd, J = 8.2, 14.4, 2H), 7.69 (t, J = 6.9, 1H), 7.59 (t, J = 7.4, 1H), 7.08 (dd, J = 4.6, 8.3, 1H)
MS (ESI) [M + H]⁺ = 267

107 ¹H NMR (300 MHz, CDCl₃) δ 8.77 (dd, J = 1.5, 4.3, 1H), 8.06 (dd, J = 10.8, 18.4, 3H), 7.93 (d, J = 2.4, 1H), 7.57 (dd, J = 2.4, 9.0, 1H), 7.39 (ddd, J = 3.1, 8.3, 12.5, 3H), 6.93 (d, J = 8.4, 1H), 6.89 (s, 1H), 2.29 (s, 3H)

108 ¹H NMR (300 MHz, CDCl₃) δ 8.72 (dd, J = 1.6.4.2, 1H), 8.61 (d, 7 = 2.4, 1H), 8.11 (d, J = 8.3, 1H), 8.00 (d, J = 9.0, 1H), 7.91 (dd, J = 1.2, 5.0, 1H), 7.69 (dd, J = 2.4, 9.1, 1H), 7.35-7.26 (m, 2H), 7.01 (dd, J = 1.2, 7.9, 1H), 6.77 (dd, J= 5.1, 7.8, 1H), 3.93 (s, 3H)

109 ¹H NMR (300 MHz, CDCl₃) δ 9.68 (s, 1H), 8.21 (s, 2H), 7.94 (d, J = 8.9, 1H), 7.79 (d, J = 9.2, 1H), 7.67 (d, J = 2.3, 1H), 7.56 (dd, J = 2.3, 8.9. 1H), 7.34 (d, J = 8.9, 1H)
MS (ESI) [M + H]⁺ = 257

110 ¹H NMR (300 MHz, CDCl₃) δ 10.32 (s, 1H), 8.33-8.21 (m, 2H), 8.05 (d, J = 8.9, 1H), 8.00 (dd, J = 1.2, 7.6, 1H), 7.69 (dd, J = 1.1, 7.8, 1H), 7.61 (s, 1H), 7.30-7.22 (m, 3H), 7.16 (d, J = 8.8, 1H).
MS (ESI) [M + H]⁺ = 301-303

111 ¹H NMR (300 MHz, CDCl₃) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H)

112 ¹H NMR (300 MHz, CDCl₃) δ 7.89 (d, J = 8.9, 1H), 7.76 (d, J = 8.5, 1H), 7.63 (d, J = 8.1, 1H), 7.59 (s, 1H), 7.54 (d, J = 8.8. 2H), 7.38-7.24 (m, 3H), 7.09 (d, J = 7.4, 1H), 7.02 (dd, J = 2.4, 8.8, 4H), 6.90 (d, J = 8.9, 1H)
¹³C NMR (75 MHz, DMSO) δ 152.94, 150.19, 142.48, 142.18, 138.20, 137.55, 135.74, 129.71, 126.99, 125.35, 123.84, 114.75.
MS (ESI) [M + H]⁺ = 255

113 ¹H NMR (300 MHz, CDCl₃) δ 9.74 (s, 1H), 8.20 (s, 2H), 8.03 (d, J = 8.6, 1H), 7.87 (d, J = 7.6, 1H), 7.80 (s, 1H), 7.70 (d, J = 8.0, 1H), 7.63 (t, J = 7.7, 1H), 7.37 (t, J = 7.4, 1H), 7.30 (d, J = 8.7, 1H)

TABLE II-continued

| Ex | Characterizations |
|---|---|
| 114 | $^1$H NMR (300 MHz, CDCl$_3$) δ 9.67 (s, 1H), 8.34-8.12 (m, 2H), 7.84 (d, J = 8.0, 2H), 7.70-7.54 (m, 1H), 7.38 (t, J = 7.6, 1H), 7.17 (s, 1H), 2.61 (s, 3H) MS (ESI) [M + H]$^+$ = 237 |
| 115 | $^1$H NMR (300 MHz, CDCl$_3$) δ 10.15 (s, 1H), 8.24-8.12 (m, 2H), 7.79 (s, 1H), 7.71 (s, 1H), 7.55 (t, J = 8.3, 2H), 7.30 (t, J = 7.9, 1H), 2.38 (s, 3H) MS (ESI) [M + H]$^+$ = 237 |
| 116 | MS (ESI) [M + H]$^+$ = 240 |
| 117 | MS (ESI) [M + H]$^+$ = 253 |
| 118 | MS (ESI) [M + H]$^+$ = 222 |
| 119 | MS (ESI) [M + H]$^+$ = 256 |
| 121 | MS (ESI) [M + H]$^+$ = 222 |
| 124 | $^1$H NMR (300 MHz, CDCl$_3$) δ 8.42 (s, 1H), 7.95 (dd, J = 1.3, 8.2. 1H), 7.87-7.78 (m, 3H), 7.70-7.61 (m, 1H), 7.55-7.47 (m, 1H), 7.26 (dd, J = 2.4, 6.5, 3H). 6.90 (s, 1H) MS (ESI) [M + H]$^+$ = 306 |
| 125 | $^1$H NMR (300 MHz, CDCl$_3$) δ 8.42 (s, 1H), 8.03 (d, J = 9.5, 1H), 7.92 (d, J = 8.2, 1H), 7.73 (d, J = 8.2, 1H), 7.61 (t, J = 7.3, 1H), 7.46 (t, J = 7.2, 1H), 7.13 (s, 2H), 6.84 (s, 1H), 2.35 (s, 3H) |
| 126 | $^1$H NMR (300 MHz, CDCl$_3$) δ 8.40 (s, 1H), 8.03 (s, 1H), 7.94 (d, J = 8.2, 1H), 7.84 (d, H = 8.2, 1H), 7.65 (t, J = 7.4, 1H), 7.53 (d, J = 7.1, 1H), 7.48 (d, J = 7.2, 1H), 7.35 (t, J = 8.2, 1H), 7.22 (s, 1H), 6.94 (d, J = 8.1, 1H) |
| 127 | $^1$H NMR (300 MHz, CDCl$_3$) δ 8.85 (dd, J = 1.0, 8.3, 1H), 8.47 (s, 1H), 7.96 (d, J = 8.2, 1H), 7.85 (d, J = 8.3, 1H), 7.72-7.61 (m, 1H), 7.57-7.47 (m, 1H), 7.42-7.36 (m, 1H), 7.33 (d, J = 10.0, 1H), 7.14 (s, 1H), 7.13-7.04 (m, 1H) |
| 128 | $^1$H NMR (300 MHz, CDCl$_3$) δ 9.17 (s, 1H), 8.68 (d, J = 9.1, 1H), 8.64 (d, J = 4.8, 2H), 8.15 (d, J = 9.1, 1H), 7.87 (d, J = 8.4, 1H), 7.76 (d, J = 8.1, 1H), 7.64 (t, J = 7.7, 1H), 7.39 (t, J = 7.5, 1H), 6.87 (t, J = 4.8, 1H) $^{13}$C NMR (75 MHz, CDCl$_3$) δ 158.34, 138.07, 129.85, 127.63, 127.31, 124.34, 114.20, 113.90. |
| 129 | $^1$H NMR (300 MHz, CDCl$_3$) δ 9.14 (s, 1H), 8.73 (d, J = 21.2, 3H), 8.17 (s, 1H), 7.73 (d, J = 20.3, 2H), 7.28 (d, J = 9.6, 2H), 6.91 (s, 1H) |
| 130 | $^1$H NMR (300 MHz, CDCl$_3$) δ 9.05 (s, 1H), 8.64 (d, J = 4.8, 2H), 8.52 (s, 1H), 7.89 (dd, J = 8.5, 14.6, 2H), 7.63 (t, J = 7.5, 1H), 7.41 (t, J = 7.4, 1H), 6.86 (t, J = 4.8, 1H), 2.74 (s, 3H) MS (ESI) [M + H]$^+$ = 237 |
| 132 | $^1$H NMR (300 MHz, CDCl$_3$) δ 8.86 (d, J = 2.6, 1H), 8.70 (d, J = 2.5, 1H), 8.32 (d, J = 1.1, 1H), 8.25-8.21 (m, 1H), 8.10 (d, J = 2.7, 1H), 8.06 (d, J = 8.3, 1H), 7.82 (dd, J = 1.2, 7.9, 1H), 7.66-7.51 (m, 3H), 6.89 (s, 1H) |
| 135 | $^1$H NMR (300 MHz, CDCl$_3$) δ 9.09 (s, 1H), 8.71 (s, 1H), 8.54 (d, J = 8.4, 1H), 8.37 (dd, = 1.0, 4.9, 1H), 7.96 (d, J = 8.2, 1H), 7.85 (d, J = 8.3, 1H), 7.82-7.74 (m, 1H), 7.66 (t, J = 7.6, 1H), 7.52 (dd, J = 7.0, 8.1, 1H), 7.02 (dd, J = 5.0, 7.2, 1H) MS (ESI) [M + H]$^+$ = 223 |
| 136 | $^1$H NMR (300 MHz, CDCl$_3$) δ 9.02 (s, 1H), 8.70 (s, 1H), 8.30 (s, 1H), 8.20 (d, J = 5.1, 1H), 7.94 (d, J = 8.1, 1H), 7.84 (d, J = 8.2, 1H), 7.64 (t, J = 7.6, 1H), 7.49 (t, J = 8.1, 1H), 6.83 (d, J = 5.0. 1H), 2.43 (s, 3H) $^{13}$C NMR (75 MHz, CDCl$_3$) δ 153.28, 150.20, 148.55, 147.40, 140.93, 139.83, 138.35, 130.44, 129.16, 127.18, 126.28, 119.70, 113.75, 21.87. MS (ESI) [M + H]$^+$ = 237 |
| 137 | $^1$H NMR (300 MHz, DMSO) δ 11.10 (s, 1H), 9.03 (s, 1H), 8.82-8.75 (m, 1H), 8.56 (d, J = 8.9, 1H), 8.24 (dd, J = 2.3, 8.9, 1H), 7.96 (dd, J = 1.2, 8.2, 1H), 7.87 (dd, J = 1.0, 8.3, 1H), 7.79-7.71 (m, 1H), 7.61 (ddd, J = 1.4, 7.0, 8.3, 1H) MS (ESI) [M + H]$^+$ = 248 |
| 138 | $^1$H NMR (300 MHz, CDCl$_3$) δ 8.72 (s, 1H), 8.53 (s, 1H), 8.20 (d, J = 8.3, 1H), 7.93 (d, J = 8.2, 1H), 7.81 (d, J = 8.3, 1H), 7.62 (td, J = 3.4, 8.1, 2H), 7.53-7.43 (m, 1H), 6.83 (d, J = 7.4, 1H), 2.48 (s, 3H) $^{13}$C NMR (75 MHz, CDCl$^3$) δ 156.86, 152.27, 148.40, 140.92, 139.70, 139.00, 138.35, 130.42, 129.13, 127.14, 126.27, 117.76, 110.01, 24.15. MS (ESI) [M + H]$^+$ = 237 |
| 139 | $^1$H NMR (300 MHz, CDCl$_3$) δ 8.53 (s, 1H), 8.20 (d, J = 4.8, 1H), 8.04 (d, J = 8.3, 1H), 7.92 (d, J = 8.4, 1H), 7.87 (s, 1H), 7.79 (t, J = 7.6. 1H), 7.60 (t, J = 7.6, 1H), 6.88 (d, J = 4.7, 1H), 2.46 (s, 3H) |
| 140 | $^1$H NMR (300 MHz, CDCl$_3$) δ 9.93 (s, 1H), 8.19 (s, 1H), 8.05 (d, J = 8.1, 1H), 7.99 (s, 1H), 7.82 (d, J = 8.2, 1H), 7.69 (t, J = 7.6, 1H), 7.59 (t, J = 8.2, 1H), 2.53 (s, 4H) |
| 141 | $^1$H NMR (300 MHz, CDCl$_3$) δ 9.72 (s, 1H), 9.35(s, 1H), 8.30 (d, J = 5.0, 1H), 8.05 (d, J = 7.7, 1H), 7.87 (d, J = 7.0, 1H), 7.66 (dd, J = 7.4, 16.9, 3H), 6.92 (d, J = 4.9, 1H), 2.58 (s, 3H) |
| 143 | $^1$H NMR (300 MHz, DMSO) δ 8.85 (s, 1H), 8.42 (d, J = 5.3, 1H), 7.96 (d, J = 9.1, 1H), 7.44 (s, 1H), 7.30 (s, 4H), 7.28-7.21 (m, 2H), 6.66 (d, J= 5.3, 1H), 2.99 (s, 6H) $^{13}$C NMR (75 MHz, DMSO) δ 156.82, 150.25, 149.69, 143.79, 141.71, 125.95, 122.33, 118.88, 117.37, 115.95, 109.39, 104.92, 43.57 MS (ESI) [M + H]$^+$ = 348 |
| 144 | MS (ESI) [M + H]$^+$ = 390 |
| 145 | MS (ESI) [M + H]$^+$ = 252 |
| 146 | $^1$H NMR (300 MHz, DMSO) δ 9.34 (s, 1H), 8.59 (d, J = 5.2, 1H), 8.53 (s, 1H), 8.13 (d, J = 5.1, 1H), 7.98 (d, J = 9.0, 1H), 7.66 (d, J = 9.1, 1H), 6.80 (d, J = 5.2, 1H), 6.76 (s, 1H), 6.69 (d, J = 4.9, 1H), 4.00 (s, 3H), 2.26 (s, 3H) $^{13}$C NMR (75 MHz, DMSO) δ 161.31, 155.67, 151.63, 150.25, 147.77, 147.01, 142.97, 121.56, 119.16, 116.61, 114.75, 112.60, 111.41, 98.91, 55.78, 20.66. MS (ESI) [M + H]$^+$ = 266 |

TABLE II-continued

| Ex | Characterizations |
|---|---|
| 147 | MS (ESI) [M + H]⁺ = 279 |
| 149 | MS (ESI) [M + H]⁺ = 318 |
| 150 | MS (ESI) [M + H]⁺ = 280 |
| 151 | $^1$H NMR (300 MHz, CDCl$_3$) δ 8.35 (s, 1H), 8.04 (d, J = 8.3, 1H), 7.82 (d, J = 8.9, 1H), 7.74 (d, J = 8.9, 1H), 7.60 (t, J = 7.8, 2H), 7.50 (dd, J = 2.3, 8.9, 1H), 7.36 (d, J = 8.9, 1H), 6.79 (d, J = 7.4, 1H), 2.75 (q, J = 7.6, 2H). 1.30 (t, J = 7.6, 3H). MS (ESI) [M + H]⁺ = 284 |
| 152 | $^1$H NMR (300 MHz, CDCl$_3$) δ 8.30 (d, J = 8.5, 1H), 8.08 (s, 1H), 7.90 (d, J = 9.0, 1H), 7.77 (d, J = 8.9, 1H), 7.65 (d, J = 2.2, 1H), 7.55 (td, J = 2.0, 8.8, 2H), 7.39 (d, J = 9.0, 1H), 2.31 (s, 3H). MS (ESI) [M + H]⁺ = 270 |
| 153 | $^1$H NMR (300 MHz, CDCl$_3$) δ 8.75 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9. 1H), 7.35 (d. J = 8.9. 1H). MS (ESI) [M + H]⁺ = 324 |
| 154 | $^1$H NMR (300 MHz, DMSO) δ 9.08 (s, 1H), 8.12 (d, J = 8.4, 1H), 7.73 (d, J = 8.2. 2H), 7.66 (d, J = 10.0, 1H), 7.53(s, 1H), 7.25 (s, 1H), 6.82 (s, 1H), 5.10 (s, 2H), 2.16 (s, 4H). MS (ESI) [M + H]⁺ = 285 |
| 155 | $^1$H NMR (300 MHz, CDCl$_3$) δ 7.68 (d, J = 8.3, 1H), 7.61 (s, 1H), 7.56 (d, J = 11.5, 2H), 7.44 (d, J = 8.3, 1H), 7.38 (d, J = 7.8, 1H), 7.13 (t, J = 7.4, 1H), 6.80 (d, J = 8.7, 2H), 3.85 (t, J = 6.5, 2H), 2.18 (s, 3H), 1.73-1.58 (m, 2H), 1.48-1.31 (m, 2H). 0.88 (t, J = 7.3, 3H) MS (ESI) [M + H]⁺ = 307 |
| 156 | $^1$HNMR (300 MHz, CDCl$_3$) δ 7.75 (d, J = 9.1, 1H), 7.62 (d, J = 8.9, 1H), 7.58 (d, J = 2.2, 1H), 7.48 (dd, J = 2.4, 8.9, 1H), 7.30 (d, J = 8.9, 2H), 6.86 (d, J = 9.0, 1H), 6.77 (d, J = 8.9, 2H), 6.71 (s, 1H), 2.97 (s, 6H) MS (ESI) [M + H]⁺ = 298 |
| 157 | $^1$H NMR (300 MHz, CDCl$_3$) δ 7.98 (d, J = 2.6, 1H), 7.89 (d, J = 8.9, 1H), 7.72 (d, J = 7.5, 1H), 7.62 (dd, J = 2.6, 8.8, 1H), 7.55 (d, J = 7.8, 1H), 7.20 (t, J = 7.8, 1H), 6.95 (d, 7 = 8.9, 1H), 6.84 (d, J = 8.9, 1H), 6.79 (s, 1H), 3.91 (s, 3H) MS (ESI) [M + H]⁺ = 319 |
| 158 | $^1$H NMR (300 MHz, CDCl$_3$) δ 7.89 (d, J = 9.0, 1H), 7.70 (dd, J = 1.2, 7.5, 1H), 7.56 (dd, J = 1.1, 8.0, 1H), 7.30 (d, J = 8.6, 1H), 7.20 (t, J = 7.8, 1H), 6.71 (t, J =5.9, 2H), 6.64 (d, J = 9.5, 1H). MS (ESI) [M + H]⁺ = 354 |
| 159 | $^1$H NMR (300 MHz, CDCl$_3$) δ 8.80 (d, J = 2.6, 1H), 8.37 (d, J = 2.6, 1H), 8.01 (d, J = 8.1, 1H), 7.91 (dd, J = 1.6, 4.9, 1H), 7.78-7.70 (m, 1H), 7.58-7.43 (m, 2H), 7.09 (dd, J= 1.6, 7.6, 1H), 6.84 (dd, J = 4.9, 7.6, 1H), 6.69 (s, 1H), 3.82-3.07 (m, 2H). |
| 160 | $^1$H NMR (300 MHz, CDCl$_3$) δ 9.68-8.90 (m, 1H), 8.77 (s, 1H), 8.35 (s, 1H). 8.14 (d, J = 5.0, 1H), 7.96 (s, 1H), 7.79 (d, J = 8.8, 1H), 7.61 (d, J = 8.5, 1H), 6.88 (d, J = 4.8, 1H), 2.46 (s, 3H) |
| 161 | $^1$H NMR (300 MHz, CDCl$_3$) δ 9.98 (s, 1 H), 8.70 (s, 1H), 8.45 (s, 1H), 8.27 (d, J = 5.2, 1H), 7.94 (d, J = 8.1, 1H), 7.84 (d, J = 8.2, 1H), 7.63 (t, J = 7.5, 1H), 7.48 (t, J = 7.5, 1H), 6.87 (d, J = 5.0, 1H), 2.74 (q, J = 7.6. 2H), 1.34 (t, J = 7.6. 3H). MS (ESI) [M + H]⁺ = 251 |
| 162 | $^1$H NMR (300 MHz, CDCl$_3$) δ 8.73 (s, 1H), 8.70-8.60 (m, 1H), 8.48 (s, 1 H), 8.31 (s, 1H), 7.98 (d, J = 8.1, 1H), 7.86 (d, J = 7.9, 1H), 7.68 (t, J = 8.2, 1H), 7.54 (t, J = 8.1, 1H), 2.49 (s, 3H) MS (ESI) [M + H]⁺ = 315 |
| 163 | $^1$H NMR (300 MHz, CDCl$_3$) δ 8.75 (s, 1H), 8.68 (s, 1H), 8.01 (s, 1H), 7.95 (d, J = 8.2, 1H), 7.84 (d, J = 8.3, 1H), 7.64 (t, J = 8.2, 1H), 7.49 (t, J = 7.0. 1H), 6.69 (s, 1H), 2.45 (s, 3H), 2.38 (s, 3H) MS (ESI) [M + H]⁺ = 251 |
| 164 | 1H NMR (300 MHz, DMSO) δ 10.46 (s, 1H), 9.00 (s, 1H), 8.41 (s, 1H), 8.24 (d, J = 3.0, 1H), 7.90 (d, J = 8.2, 1H), 7.79 (d, J = 8.3, 1H), 7.69 (t, J = 7.0, 1H), 7.52 (t, J = 7.4, 1H), 6.98 (d, J = 4.8, 1H), 5.45 (q, J = 5.6, 1H), 4.58 (d, J = 5.7. 2H). MS (ESI) [M + H]⁺ = 253 |
| 165 | $^1$H NMR (300 MHz, CDCl$_3$) δ 9.07 (s, 1H), 8.79 (s, 1H), 8.51 (s, 1H), 8.18 (s, 1H), 8.09-8.01 (m, 1H), 7.94 (d, J = 8.4, 1H), 7.81-7.71 (m, 1H), 7.69-7.59 (m, 1H), 2.80 (s, 3H) MS (ESI) [M + H]⁺ = 282 |
| 166 | $^1$H NMR (300 MHz, CDCl$_3$) δ 8.49 (d, J = 5.0, 1H), 7.77 (d, J = 9.0, 1H), 7.32 (d, J = 2.0, 1H), 7.12 (d, J = 9.0, 2H), 6.99 (dd, J = 2.0, J = 9.0, 1H), 6.82 (d, J = 9.0, 2H), 6.57 (d, J = 5.0, 1H), 5.78 (s, 1H), 3.74 (s, 3H), 3.17 (s, 4H), 2.62 (s, 4H), 2.34 (s, 3H) |
| 167 | MS (ESI) [M + H]⁺ = 335 |
| 168 | MS (ESI) [M + H]⁺ = 321 |

The following examples illustrate in detail the preparation of compounds (51), (64), (110), (143) and (148) as described above. The structures of the products obtained have been confirmed at least by NMR spectra.

Embodiment I: Examples

According to route (A), the compound of formula (III) is placed in a protic solvent such as tert-butanol. The compound of formula (IV) is then added in a 1.1 molar ratio with respect to the compound of formula (III) in presence of an inorganic base, such as $Cs_2CO_3$ or $K_2CO_3$, in a 2.8 molar ratio, in the presence of a diphosphine, such as Xantphos (4,5-Bis(diphenylphosphino)-9,9-dimethylxanthene), or X-Phos 2-Dicyclohexylphosphino-2',4',6'-triisopropylbiphenyl in a 2 mol % amount relative to the total amount of compound of formula (III), and in the presence of a catalyst, such as $Pd(OAc)_2$ or $Pd_2dba_3$ in a 2 mol % amount relative to the total amount of compound of formula (III). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compounds (51), (64), (110), and (143).

According to route (B), the compound of formula (V) is placed in a protic solvent such as tert-butanol. The compound of formula (VI) is then added in a 1.1 molar ratio with respect to the compound of formula (V) in presence of $Cs_2CO_3$ in a 2.8 molar ratio, in the presence of Xantphos (4,5-Bis(diphenylphosphino)-9,9-dimethylxanthene) in a 2 mol % amount relative to the total amount of compound of formula (V), and in the presence of a $Pd(OAc)_2$, in a 2 mol % amount relative to the total amount of compound of formula (V). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compound (148).

Example 1: Compound (51) of Table I

According to route (A), a mixture of 2,8-dichloroquinoline (98.5 mg) and 2-amino-4,6-dimethylpyridine (67.1 mg), $Pd(OAc)_2$ (2.2 mg), XantPhos (5.8 mg) and $Cs_2CO_3$ (456 mg) in 2 mL of t-BuOH gave compound (51) (99.7 mg).

Example 2: Compound (64) of Table I

According to route (A), a mixture of 2-chloro-5-nitroquinoline (100.0 mg) and 2-amino-4-methylpyridine (57.6 mg), $Pd_2dba_3$ (20 mg), XantPhos (30 mg) and $K_2CO_3$ (270 mg) in 3 mL of t-BuOH gave compound (64) (14.0 mg).

The preparation of 2-chloro-5-nitroquinoline is described in Patent application WO2009/23844.

Example 3: Compound (110) of Table I

According to route (A), a mixture of 8-bromo-2-chloroquinoline (500 mg) and aminopyrazine (216 mg), $Pd_2dba_3$ (95 mg), XantPhos (120 mg) and $K_2CO_3$ (1.15 g) in 12 mL of t-BuOH gave compound (110) (245 mg).

The preparation of 8-bromo-2-chloroquinoline is described in Cottet, F. et al. Eur. J. Org. Chem. 2003, 8, 1559.

Example 4: Compound (143) of Table I

According to route (A), a mixture of 7-chloro-4-(N,N-dimethylamino)quinoline (500 mg), 4-trifluoromethoxyaniline (0.257 mL), $Pd_2dba_3$ (110 mg), XPhos (115 mg) and $K_2CO_3$ (1 g) in 10 mL of t-BuOH gave compound (143) (410 mg).

The preparation of 7-chloro-4-(N,N-dimethylamino)quinoline is described in Sanchez-Martin, R. et al. J. Med. Chem. 2005, 48, 3354.

Example 5: Compound (148) of Table I

According to route (B), a mixture of 5,8-dimethylisoquinolin-6-amine (59 mg) and 2-bromo-5-methylpyridine (86 mg), $Pd(OAc)_2$ (2.2 mg), XantPhos (5.8 mg) and $Cs_2CO_3$ (456 mg) in 2 mL of t-BuOH gave compound (148) (48 mg).

The preparation of 5,8-dimethylisoquinolin-6-amine is described in Australian Journal of Chemistry 1969, 22, 2489.

1H NMR (300 MHz, CDCl3) δ 9.32 (s, 1H), 8.52 (d, J=6.0, 1H), 8.07 (s, 1H), 7.72 (d, J=6.0, 1H), 7.51 (s, 1H), 7.36 (dd, J=2.1, 8.4, 1H), 6.69 (d, J=8.3, 2H), 2.72 (s, 3H), 2.48 (s, 3H), 2.26 (s, 3H)

MS (ESI) [M+H]+=264

Example 6: Pharmacological Data

Standard Operating Procedure:
Effect of drug compounds on invasion of MDA-MB231-D3H2LN cells into collagen
Background:
A key step in the generation of tumor metastasis is tumor cell invasion of the extracellular matrix, a major component of which is collagen. Therefore, the invasion of tumor cells into collagen in vitro may be indicative of tumor metastasis in vivo. E. g., MDA-MB231-luc-D3H2LN mouse breast cancer cells display both higher invasion into collagen in vitro and a higher metastatic potential in vivo as compared to MDA-MB231 cells (from which they were derived). Using these MDA-MB231-luc-D3H2LN cells as a model, the aim of the experiment described here is to identify drug compounds that inhibit the invasion of tumor cells into collagen in vitro, therefore potentially inhibiting also the generation of tumor metastasis in vivo.

Assay Principle:
Step 1:
Preparation of cells at the bottom of a collagen gel: Cells were suspended in a liquid collagen solution (4° C.), distributed into BSA-coated wells, and then collected at the bottom of the wells by centrifugation. The collagen was then solidified by incubation at 37° C. The BSA coating improves the adhesion of the collagen gel.

Step 2:
Pre-treatment with the compounds to be tested: Concentrated drug solutions were then added on top of the collagen, and cells are pre-incubated for 24 h with the drugs at low serum conditions (0.025% FBS).

Step 3:
Stimulation of invasion: Medium with 5% FBS was then added in order to stimulate invasion of the cells into the collagen gel.

Step 4:

Fixation and staining: Following another 24 h incubation, cells were fixed and nuclei were stained.

Step 5:

Analysis: Finally, plates were analyzed using an automated microscope. Fluorescent beads that have been included into the BSA coating serve to detect the bottom of the wells. Pictures of the stained nuclei were taken at the same level (0 µm) as well as 25 µm and 50 µm above.

Note:

In order to detect possible toxic effects, all compounds were tested in parallel in a viability assay. The viability assay was performed in parallel on serum-starved cells (as in the invasion assay) vs. cells under normal culture conditions (10% FBS).

Materials:

General Equipment:

Freezer (−20° C.), refrigerator (4° C.), ice machine, water bath (37° C.), incubator (37° C./5% CO$_2$), cell culture hood, vortex, vacuum pump, microscope, Malassez cell, Pipet aid, micropipettes (for pipetting 1-1000 µl), multichannel pipettes (for pipetting 20-200µl), standard cell culture centrifuge, refrigerated centrifuge for 96 well plates.

General Consumables:

Sterile 96 well cell culture plates (for the viability assay), sterile tubes (1.5/15/50 ml), sterile pipettes (5/10/25 ml), sterile micropipette tips (for pipetting 1-1000 µl), sterile Pasteur pipettes, sterile reagent reservoirs.

General Products:

Sterile PBS, sterile Milli-Q water, DMSO, decomplemented FBS (frozen aliquots), 0.1 N NaOH, 1 M Hepes, MEM without serum (not older than 1 month), 2.5×MEM without serum (not older than 1 month), MEM with 10% FBS (not older than one month), 0.25% trypsin/1 mM EDTA solution, 37% formaldehyde solution.

Specific Equipment:

plate reader: Tecan Infinite F200 automated microscope: Cellomics ArrayScan VTI HCS Reader

Specific Consumables:

sterile black 96 well plates (for the invasion assay): Perkin Elmer ViewPlate-96 F TC, ref. 6005225 sterile 96 deep well polypropylene plates (for drug preparation): Starlab, ref. S1896-5110

Specific Products:

rat tail collagen, type 1: BD Biosciences, ref. 354236 (note: each new lot has to be validated)

red fluorescent beads (1 m diameter): Invitrogen, ref. F13083

Y-27632 (5 mM aqueous solution): Calbiochem, ref. 688001 (in solution) or 688000 (dry powder)

BSA without fatty acids (sterile-filtered 4% aqueous solution): Sigma, ref. A8806 (dry powder)

Hoechst 33342 nuclear stain (10 mg/ml): Invitrogen, ref. H3570

MTS reagent: Promega CellTiter CellTiter 96® AQueous One Solution Reagent, ref. G3581 drug compounds to be tested: generally 25 or 50 mM in 100% DMSO (aliquots stored at −20° C., then at 4° C. for max. 3 months)

MDA-MB231-luc-D3H2LN cells:

Limits for the cell cultures to be used in the assays:

total passage number: max. 30 last passage: between 2 and 4 days before, between 1:3 and 1:20 cell density: between 50 and 90% (optimally 70%) (between 1 and 2×106 cells per 100 mm dish)

Experimental Procedures

General Considerations: Controls and Plate Maps:

Invasion assay: Negative control: No drug (just DMSO at equivalent concentration). Positive control: 10 µM Y-27632. To avoid edge effects, only the 60 central wells B2-G11 were used; lines A and H as well as columns 1 and 12 remain free. Each drug was tested at least in triplicate. The positive and negative controls were tested in double triplicates at different positions on each plate. Typical plate map (−=negative control, +=positive control, 1-16=16 different drug compounds):

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | − | 1 | 2 | 3 | 4 | 5 | 6 | 7 | 8  | +  |    |
| C |   | − | 1 | 2 | 3 | 4 | 5 | 6 | 7 | 8  | +  |    |
| D |   | − | 1 | 2 | 3 | 4 | 5 | 6 | 7 | 8  | +  |    |
| E |   | + | 9 | 10| 11| 12| 13| 14| 15| 16 | −  |    |
| F |   | + | 9 | 10| 11| 12| 13| 14| 15| 16 | −  |    |
| G |   | + | 9 | 10| 11| 12| 13| 14| 15| 16 | −  |    |
| H |   |   |   |   |   |   |   |   |   |    |    |    |

Viability Assays:

No additional controls. The MTS viability assay was based on colorimetric detection of a product generated by the mitochondrial activity of the cells. Each drug was tested at least in duplicate. To detect potential direct interactions with the assay substrate, each drug was also tested in absence of cells (background signals). Typical plate map (controls and drug compounds as in the invasion assay, lines A-B and E-F: with cells, lines C-D and G-H: without cells; each 1 plate with 10% vs. 0.025% FBS):

|   | 1 | 2 | 3 | 4 | 5 | 6 | 7 | 8 | 9 | 10 | 11 | 12 |
|---|---|---|---|---|---|---|---|---|---|----|----|----|
| A |   | − | 1 | 2 | 3 | 4 | 5 | 6 | 7 | 8  | +  |    |
| B |   | − | 1 | 2 | 3 | 4 | 5 | 6 | 7 | 8  | +  |    |
| C |   | − | 1 | 2 | 3 | 4 | 5 | 6 | 7 | 8  | +  |    |
| D |   | − | 1 | 2 | 3 | 4 | 3 | 6 | 7 | 8  | +  |    |
| E |   | + | 9 | 10| 11| 12| 13| 14| 15| 16 | −  |    |
| F |   | + | 9 | 10| 11| 12| 13| 14| 15| 16 | −  |    |
| G |   | + | 9 | 10| 11| 12| 13| 14| 15| 16 | −  |    |
| H |   | + | 9 | 10| 11| 12| 13| 14| 15| 16 | −  |    |

The volumes or other quantities indicated in the following are required for testing 16 drug compounds per 96 wells-plate at 5 µM each (+controls) in an invasion assay and each one viability assay on serum-starved cells vs. cells under normal culture conditions according to the plate maps above. According to the number of tested compounds, the volumes and other quantities should be adapted for testing more or less compounds or different concentrations.

Day 1: Preparation and Treatment of the Cells (all Steps are Performed Under a Cell Culture Hood):

Preparation of 100× concentrated drug solutions in 10% DMSO:

prepare 10% DMSO in sterile PBS: 1.8 ml sterile PBS+ 0.2 ml DMSO prepare 100 µl/well 10% DMSO in PBS in 16 wells of a sterile 96 well polypropylene plate add each 1 or 2 µl of the 50 or 25 mM compound stock solutions, respectively mix by pipetting up and down Preparation of 4× concentrated drug and control solutions in 0.4% DMSO in MEM+0.1% FBS:

Prepare MEM+0.1% FBS: 12 ml MEM without serum+12 µl FBS (freshly thawed aliquot)

prepare 480 µl/well MEM+0.1% FBS in 20 wells of a sterile 96 deep well polypropylene plate negative controls (no drug): add each 20 µl 10% DMSO in sterile PBS positive controls (Y-27632): add each 14 µl sterile PBS+2 µl DMSO+4 µl 5 mM Y-27632 (freshly thawed aliquot)

drug compounds: add each 20 µl of the 100× concentrated drug solutions in 10% DMSO mix by pipetting up and down store at RT until use Coating of the Plates for the Invasion Assay:

mix 9.5 ml MEM without serum+0.5 ml 4% BSA without fatty acids+1 µl vortexed fluorescent beads (i. e. dilute 1:10000), vortex, distribute 100 µl/well into the plate for the invasion assay centrifuge 30' with 1800×g at 4° C. (e. g. 3000 rpm in a Jouan GR412 centrifuge)

remove supernatants by aspiration

Preparation of a 10×106 Cells/Ml Cell Suspension (During the Centrifugation of the Plates):

remove medium, wash cells with ~10 ml/dish PBS, add 1 ml/dish 0.25% trypsin/1 mM EDTA incubate 30-60 s at 37° C.

add 5-10 ml/dish pre-warmed MEM+10% FBS homogenize by pipetting up and down using a 10 ml pipette, pool all count cells using a Malassez cell centrifuge 2×106 (or more) cells for 5' with 150×g at RT (850 rpm in a std. cell culture centrifuge)

remove supernatant, resuspend cell pellet in 0.2 ml (or more, respectively) MEM without serum, yielding 10×106 cells/ml Preparation of the Invasion Assay (on Ice; Start During the Centrifugation of the Cells):

mix on ice in a pre-chilled tube: example for a 3.4 mg/ml collagen stock solution; volumes of collagen and water to be adapted according to the stock concentration of each collagen lot:

2.8 ml 2.5×MEM

441 µl water

140 µl 1 M Hepes

49 µl 1 N NaOH 3.5 ml 3.4 mg/ml collagen stock solution (yielding 1.7 mg/ml collagen in 7 ml)

homogenize by pipetting gently up and down (keep on ice)

add 70 µl of the 10×106 cells/ml cell suspension, homogenize by pipetting gently up and down (yields 0.1×106 cells/ml in 1.7 mg/ml collagen in 7 ml 1×MEM+20µM Hepes) (keep on ice)

distribute 100 µl/well (i. e. 10000 cells/well) into the coated wells of the plate for the invasion assay (all on ice)

centrifuge 5' with 200×g at 4° C. (e. g. 1000 rpm in a Jouan GR412 centrifuge)

add 200 µl/well PBS to all free wells incubate 30' at 37° C./5% $CO_2$ (solidification of the collagen)

Preparation of the Viability Assay on Serum-Starved Cells:

add 50 µl of the 10×106 cells/ml cell suspension to 5 ml MEM without serum (yields 0.1×106 cells/ml)

distribute 100 µl/well of this suspension (i. e. 10000 cells/well) or MEM without serum without cells, respectively, into a standard 96 well tissue culture plate, according to the plate map above add 200 µl/well PBS to all free wells incubate 30' at 37° C./5% $CO_2$ Preparation of the Viability Assay on Cells Under Normal Culture Conditions:

add 30 µl of the 10×106 cells/ml cell suspension to 5 ml MEM+10% FBS (yields 0.06×106 cells/ml)

distribute 100 µl/well of this suspension (i. e. 6000 cells/well) or MEM+10% FBS without cells, respectively, into a standard 96 well tissue culture plate, according to the plate map above add 200 µl/well PBS to all free wells incubate 30' at 37° C./5% $CO_2$ Treatment with the Drugs:

add each 33 µl/well of the 4× concentrated drug solutions in MEM+0.1% FBS to the corresponding wells in all three plates, according to the plate maps above incubate 24 h at 37° C./5% $CO_2$ Day 2: Addition of FBS to Stimulate the Invasion:

Microscopic Observation after 24 h of Treatment:

examine the cells of the viability assays

Addition of FBS (Under a Cell Culture Hood):

prepare MEM+5% FBS: 7.2 ml MEM without serum+0.8 ml FBS (freshly thawed aliquot or rest of the aliquot thawed the day before if kept at 4° C.)

add 33 µl/well to all wells of invasion and viability assays incubate 24 h at 37° C./5% $CO_2$ Day 3: Stop:

Microscopic Observation After 48 h of Treatment:

examine the cells of the viability assays

Viability Assays: MTS Assay:

add each 33 µl/well of the MTS reagent, incubate 2.5 h at 37° C./5% $CO_2$ shake and read absorbance at 490 nm (proportional to the viability)

calculate the background-corrected signals by subtracting the means of the background signals in absence of cells from the corresponding signals in presence of cells normalize the background-corrected signals with respect to the mean signal of the negative controls (no drug) (viabilities are thus expressed in "% of control")

Invasion Assays:

fixation and staining (formaldehyde must be manipulated under a fume cupboard):

freshly prepare 1 µg/ml Hoechst 33342 in 18.5% formaldehyde: 5 ml PBS (not necessarily sterile)+5 ml 37% formaldehyde+1 µl 10 mg/ml Hoechst 33342 (note: for one plate, a smaller volume would be sufficient, but the minimal pipetted volume should not be below 1 µl)

add 50 µl/well to all wells of the invasion assay (yields 4.3% formaldehyde final)

seal with black film (provided with the plates)

incubate at least 7 h at RT

Day 3: 17 (Min. 7 h/Max. 2 Weeks after Fixation and Staining): Analysis of the Invasion Assay:

Lecture using the Cellomics ArrayScan VTI HCS Reader:

BioApplication: SpotDetector.V3

Plate type: Perkin Elmer 96 well

Parameters of the Assay Protocol:

objective: 10×(NA 0.45)

apotome: yes (resulting optical slice: 11.7 µM)

fields per well: 8 autofocus in each field autofocus channel: 1 channel 1 (autofocus on, and photo of the fluorescent beads at the bottom of the wells): filter: XF93—TRITC; exposure time: usually between 0.002 and 0.01 s channel 2 (photo of the stained cells at the same level as the fluorescent beads): filter: XF100—Hoechst; exposure time: usually between 0.02 and 0.1 s; z offset: 0 µM channel 3 (photo of the stained cells 25 M above the fluorescent beads): filter: XF100—Hoechst; exposure time: usually between 0.02 and 0.1 s; z offset: −25 µM channel 4 (photo of the fluorescent cells 50 µM above the fluorescent beads): filter: XF100—Hoechst; exposure time: usually between 0.02 and 0.1 s; z offset: −50 µM object identification: method: fixed threshold: 100-32767

| object selection parameters: | min. | max. |
|---|---|---|
| SpotArea: | 20 | 1000000000000 |
| SpotShapeBFR: | 0.2 | 1000 |
| SpotShapeBAR: | 0 | 1000 |
| SpotAvgInten: | 200 | 32767 |
| SpotTotalInten: | ≤4000 (thus not limiting) | 1000000000000 |
| TargetAvgInten: | 0 | 32767 |
| TargetTotalInten: | 0 | 1000000000000 |

Analysis of the Results of the Scan Using vHCS Viewer:
export the results: for each well:
number of valid fields
number of objects in each valid field in each of the channels 2, 3 and 4 ("field details")
mean numbers of objects per valid field for each well, in each of the channels 2, 3 and 4
exclude wells with less than 6 valid fields per well from further analysis
visually check all photos for any apparent problems, such as bad focusing or obviously inhomogeneous collagen structure ("bubbles", . . . ), . . . ; in case of apparent problems: document, then exclude the corresponding wells from further analysis Further Analysis of the Results of the Invasion Assay (Using e. g. Excel):
For each well, the mean invasion distance was calculated as follows: (25 µm×number of cells at 25 µm+50 µm×number cells at 50 µm)/sum of cells at 0, 25 and 50 µm For all four parameters (number of cells at 0 µm, number of cells at 25 µm, number of cells at 50 µm, mean invasion distance of the counted cells), calculate means, SD and CV of the replicates (n=6 for the controls; n=3 for the samples).

Replicates having a CV≥50% (compound to be re-tested, or assay to be repeated if CV≥50% for the untreated negative control or the compound Y-27632-treated positive control) were invalidated. Y27632 is a selective inhibitor of the Rho-associated protein kinase p160ROCK of the following formula:

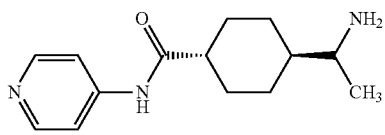 [SMILES: CC(N)[C@H]1CC[C@H](C(=O)Nc2ccncc2)CC1]

The assay was validated only if the mean invasion distance of the cells treated with 10 µM Y-27632 (positive control) was decreased by ≥40% as compared to the untreated negative control.

Graphs were plotted of all four parameters (number of cells at 0 m, number of cells at 25 µm, number of cells at 50µm, mean invasion distance of the counted cells).

Results
Anti-invasive effect at 5 µM on MDA-MB231 breast cancer cells (fold effect compared to 10 M Y-27632 ref. compound)

| Compound (family) | Invasion of MDA MB231 cells at 5 mM (fold effect of positive control) |
|---|---|
| 148 (Iee) | 0.54 |
| 109 (Ie) | 0.41 |
| 110 (Ie) | 0.64 |
| 112 (Ie) | 0.26 |
| 143 (Iq) | 0.8 |
| 144 (Iq) | 0.73 |
| 63 (Ia) | 0.69 |
| 64 (Ia) | 1.16 |
| 6 (Ia) | 0.63 |
| 18 (Ia) | 0.52 |
| 45 (Ia) | 0.50 |
| 30 (Ia) | 0.33 |
| 35 (Ia) | 0.26 |
| 36 (Ia) | 0.43 |
| 37 (Ia) | 0.34 |
| 48 (Ia) | 0.63 |
| 53 (Ia) | 0.27 |
| 51 (Ia) | 1.06 |
| 52 (Ia) | 0.27 |
| 58 (Ia) | 0.33 |
| 61 (Ia) | 0.34 |
| 58 (Ia) | 0.33 |
| 55 (Ia) | 0.27 |
| 56 (Ia) | 0.26 |

The compounds according to the present invention demonstrated an anti-invasive effect predictive for their activity against cancer.

Therefore, the results of the tests carried out with the compounds described herein demonstrated properties that may be useful to inhibit, prevent and/or treat cancer. For example, the following types of cancers may more be treated by the compounds according to the present invention: colorectal cancer, pancreatic cancer, lung cancer including non-small cell lung cancer, breast cancer, bladder cancer, gall bladder cancer, thyroid cancer, melanoma, liver cancer, uterine/cervical cancer, oesophageal cancer, kidney cancer, ovarian cancer, prostate cancer, head and neck cancer, and stomach cancer, etc.

For this purpose an effective amount of a said compound may be administered to a patient suffering from cancer.

The present disclosure is also related to the use of at least a compound chosen among a compound of anyone of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for the manufacture of a pharmaceutical composition intended for the treatment of cancer.

The present disclosure also encompasses pharmaceutical compositions comprising at least a compound chosen among new compounds of formula (Iq) or (Iee) as defined above and compounds (143), (144), (149), (166) and (167) as defined above or any pharmaceutically acceptable salt thereof.

Thus, these pharmaceutical compositions contain an effective amount of said compound, and one or more pharmaceutical excipients.

The aforementioned excipients are selected according to the dosage form and the desired mode of administration.

In this context, the compounds described herein can be present in any pharmaceutical form suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

The present disclosure is also related to the use of a compound of anyone of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for the manufacture of a pharmaceutical composition intended for inhibiting, preventing and/or treating cancer.

The present disclosure further relates to a method of treatment of patients suffering from cancer, which comprises at least a step of administration to a patient suffering thereof of an effective amount of a compound of anyone of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above and (1) to (168) or one of its pharmaceutically acceptable salts.

Embodiment II (AIDS)

In order to minimize the risk that these indole derivatives intercalate between DNA bases, the inventors developed novel compounds that are particularly effective in treating diseases related to the splicing process, but which, in a surprising manner, have a cellular toxicity that is clearly less than the indole derivatives of the prior art. In addition, these compounds are able to selectively inhibit certain splicing events.

According to a first aspect, a subject-matter of the present invention relates to a compound of formula (I)

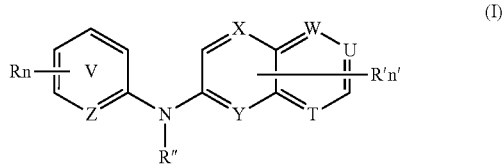

(I)

wherein:

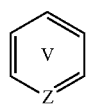

means an aromatic ring wherein V is C or N and when V is N, V is in ortho, meta or para of Z, i.e. forms respectively a pyridazine, a pyrimidine or a pyrazine group, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group and a (C$_1$-C$_3$)alkyl group, said alkyl being optionally mono-substituted by a hydroxyl group, R$_1$ and R$_2$ are independently a hydrogen atom or a (C$_1$-C$_3$)alkyl group, n is 1, 2 or 3, n' is 1 or 2, R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$) alkoxy group and a —CN group, R" is a hydrogen atom or a (C$_1$-C$_4$)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salt, for use as an agent for preventing, inhibiting or treating AIDS.

According to one aspect, the present invention relates to a compound of formula (I) as defined above, wherein Z is N, V is C, Y is N, X is C, T is C, U is C and W is C, for use as an agent for preventing, inhibiting or treating AIDS.

According to another aspect, the present invention relates to a compound of formula (I) as defined above, wherein Z is C, V is C, Y is N, X is C, T is C, U is C and W is C, for use as an agent for preventing, inhibiting or treating AIDS.

According to another aspect, the present invention relates to a compound of formula (I) as defined above, wherein Z is N, V is C, Y is C, X is N, T is C, U is C and W is C, for use as an agent for preventing, inhibiting or treating AIDS.

According to another aspect, the present invention relates to a compound of formula (I) as defined above, wherein Z is N, V is C, Y is C, X is C, T is C, U is C and W is N, for use as an agent for preventing, inhibiting or treating AIDS.

According to another aspect, the present invention relates to a compound of formula (I) as defined above, wherein Z is N, V is N and is in para of Z, Y is N, X is C, T is C, U is C and W is C, for use as an agent for preventing, inhibiting or treating AIDS.

According to another aspect, the present invention relates to a compound of formula (I) as defined above, wherein Z is C, V is N and is in para of Z, Y is C, X is N, T is C, U is C and W is C, for use as an agent for preventing, inhibiting or treating AIDS.

According to another aspect, the present invention relates to a compound of formula (I) as defined above, wherein Z is C, V is N and is in meta of Z and is in para of the bond linked to NR", Y is N, X is C, T is C, U is C and W is C, for use as an agent for preventing, inhibiting or treating AIDS.

According to another aspect, the present invention relates to a compound of formula (I) as defined above, wherein Z is C, V is N and is in meta of Z and is in para of the bond linked to NR", Y is C, X is N, T is C, U is C and W is C, for use as an agent for preventing, inhibiting or treating AIDS.

According to another aspect, the present invention relates to a compound of formula (I) as defined above, wherein Z is C, V is C, Y is C, X is N, T is C, U is C and W is C, for use as an agent for preventing, inhibiting or treating AIDS.

According to another aspect, the present invention relates to a compound of formula (I) as defined above, wherein Z is C, V is C, Y is N, X is N, T is C, U is C and W is C, for use as an agent for preventing, inhibiting or treating AIDS.

According to another aspect, the present invention relates to a compound of formula (I) as defined above, wherein Z is N, V is N and is in meta of Z and in ortho of the bond linked to NR", Y is N, X is C, T is C, U is C and W is C, for use as an agent for preventing, inhibiting or treating AIDS.

According to another aspect, the present invention relates to a compound of formula (I) as defined above, wherein Z is N, V is N and is in para of Z, Y is C, X is C, T is C, U is C and W is N, for use as an agent for preventing, inhibiting or treating AIDS.

According to another aspect, the present invention relates to a compound of formula (I) as defined above, wherein Z is N, V is N and is in para of Z, Y is C, X is N, T is C, U is C and W is C, for use as an agent for preventing, inhibiting or treating AIDS.

According to another aspect, the present invention relates to a compound of formula (I) as defined above, wherein Z is N, V is C, Y is N, X is N, T is C, U is C and W is C, for use as an agent for preventing, inhibiting or treating AIDS.

According to another aspect, the present invention relates to a compound of formula (I) as defined above, wherein Z is N, V is N and is in meta of Z and is in ortho of the bond linked to NR", Y is N, X is N, T is C, U is C and W is C, for use as an agent for preventing, inhibiting or treating AIDS.

According to another aspect, the present invention relates to a compound of formula (I) as defined above, wherein Z is C, V is C, Y is C, X is C, T is N, U is C and W is C, for use as an agent for preventing, inhibiting or treating AIDS.

According to another aspect, the present invention relates to a compound of formula (I) as defined above, wherein Z is N, V is C, Y is C, X is C, T is N, U is C and W is C, for use as an agent for preventing, inhibiting or treating AIDS.

According to another aspect, the present invention relates to a compound of formula (I) as defined above, wherein Z is N, V is C, Y is C, X is C, T is C, U is N and W is C, for use as an agent for preventing, inhibiting or treating AIDS.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates (e.g. hydrates) and the invention includes all such solvates.

In the context of EMBODIMENT II of the present disclosure, the term:
- "halogen" is understood to mean chlorine, fluorine, bromine, or iodine, and in particular denotes chlorine, fluorine or bromine,
- "$(C_1-C_3)$alkyl" as used herein respectively refers to $C_1-C_3$ normal, secondary or tertiary saturated hydrocarbon. Examples are, but are not limited to, methyl, ethyl, 1-propyl, 2-propyl,
- "$(C_1-C_3)$alkoxy" as used herein respectively refers to O—$(C_1-C_3)$alkyl moiety, wherein alkyl is as defined above. Examples are, but are not limited to, methoxy, ethoxy, 1-propoxy, 2-propoxy,
- "fluoroalkyl group" and "fluoroalkoxy group" refers respectively to alkyl group and alkoxy group as above-defined, said groups being substituted by at least one fluorine atom.

Examples are perfluoroalkyl groups, such as trifluoromethyl or perfluoropropyl, and "patient" may extend to humans or mammals, such as cats or dogs.

According to one preferred aspect, the present invention relates to a compound of formula (I) as defined above, wherein Z is N, V is C, Y is N, X is C, T is C, U is C and W is C, for use as an agent for preventing, inhibiting or treating AIDS.

According to another preferred aspect, the present invention relates to a compound of formula (I) as defined above, wherein Z is C, V is C, Y is N, X is C, T is C, U is C and W is C, for use as an agent for preventing, inhibiting or treating AIDS.

According to another preferred aspect, the present invention relates to a compound of formula (I) as defined above, wherein Z is N, V is C, Y is C, X is N, T is C, U is C and W is C, for use as an agent for preventing, inhibiting or treating AIDS.

According to another preferred aspect, the present invention relates to a compound of formula (I) as defined above, wherein Z is N, V is N and is in para of Z, Y is N, X is C, T is C, U is C and W is C, for use as an agent for preventing, inhibiting or treating AIDS.

According to another preferred aspect, the present invention relates to a compound of formula (I) as defined above, wherein Z is N, V is C, Y is N, X is N, T is C, U is C and W is C, for use as an agent for preventing, inhibiting or treating AIDS.

Another object of the present invention relates to a compound of the following formula (I'):

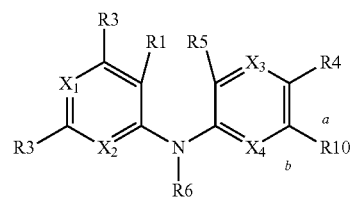

wherein:

X1, X2 and X3 independently represent a nitrogen atom, or a CR8 group, at least one of X1 and X2 being a nitrogen atom;

R8 represents a hydrogen atom or a halogen atom, a hydroxyl, alkyl, trifluoroalkyl, ester, ether, such as a methoxy or trifluoromethoxy group, or benzyl, optionally substituted, a nitro or a cyano group, preferably R8 represents a hydrogen atom, when a ring A, defined below, is in position a, X4 represents a nitrogen atom or a CR8 group, and when a ring A is in position b, X4 represents a carbon atom part of the ring A, R1, R2, R3 and R5 independently represent a hydrogen or a halogen atom, an alkyl, a trifluoroalkylgroup, ether, such as a methoxy or trifluoromethoxy group, or benzyl, optionally substituted, a nitro or a cyano group.

when the ring A is at position b, R4 represents a hydrogen atom, a halogen atom or an alkyl, a trifluoroalkyl, ester, ether group, such as a methoxy or trifluoromethoxy group, or benzyl, optionally substituted, and when the ring A is at position a, R4 is a carbon atom part of the ring A, R10 represents a carbon atom part of ring A, R6 represents a hydrogen atom or an alkyl group, A represents a ring at position a or b of formula I, said ring A corresponding to:

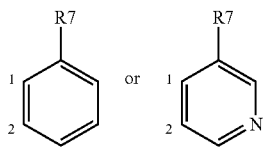

wherein:

R7 represents a hydrogen, or halogen atom or an alkyl, hydroxyl or amine group which can be linear or branched and/or unsaturated and optionally substituted, pharmaceutically acceptable salts of said compounds, isomers thereof and/or mixtures of the same, with the exception of the following compound:

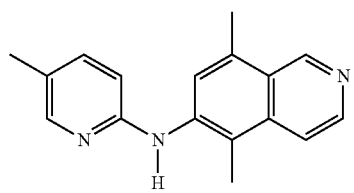

(1)

"Halogen atom" means the group comprising F, Cl, Br and I, preferably said halogen atom is a chlorine atom.

"Unsaturated" means that the group comprises at least one double bond.

All the compounds disclosed in the examples are in the scope of the present invention.

Preferably, X1 represents a CR8 group when X2 represents a nitrogen group, and

X2 represents a CR8 group when X1 represents a nitrogen group.

Preferably, at least one of X3 and X4 is a nitrogen atom when the cycle A is in position a.

Preferably X3 and X4 are different, and even more preferably X3 represents a CR8 group when X2 represents a nitrogen group or a and X4 represents a CR8 group when X1 represents a nitrogen group.

Preferably, R1 represents a hydrogen atom or a methoxy group.

Preferably, R2, R3, R4 and R5 independently represent a hydrogen atom or a halogen atom or an alkyl, or benzyl, optionally substituted.

Preferably, R4 represents a hydrogen atom.

Preferably, R2 represents a hydrogen atom or a C1 to C4 alkyl group, preferably a methyl.

Preferably, R3, R5 and R6 independently represent a hydrogen atom.

Preferably, R7 represents a hydrogen, or halogen atom, more preferably a hydrogen or a chlorine atom.

Preferably, the ring A is attached at position a or b of the compound of formula I via the carbons numbered 1 and 2 in ring A.

Preferably, when the ring A is at position a, R4 is the carbon atom numbered 2 of the ring A, more preferably R4 is the carbon atom numbered 2 of the ring A and R10 is the carbon numbered 1.

Preferably, when a ring A is in position b, X4 is the carbon atom numbered 1 of the ring A, more preferably, X4 is the carbon atom numbered 1 of the ring A and R10 is the carbon numbered 2.

Preferably, the compound as described above does not include the following compounds:

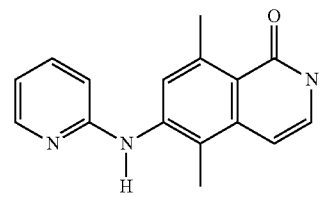

5,8-Dimethyl-6-(pyridin-2-ylamino)-2H-isoquinolin-1-one

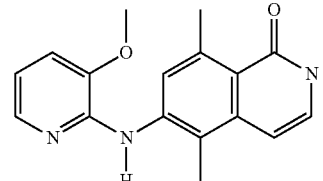

5,8-diméthyl-6-(3 methoxy-pyridin-2-ylamino)-isoquinolin-1-one

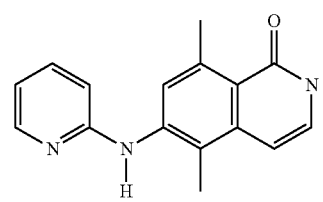

5,8-Dimethyl-6-(pyridin-2-ylamino)-2H-isoquinolin-1-one

Advantageously, the compound of formula I is chosen among the group comprising:

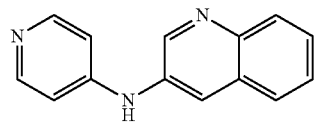

Pyridin-4-yl-quinolin-3-yl-amine; compound (121) of table I

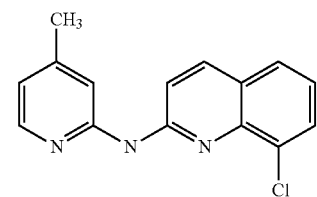

(8-Chloro-quinolin-2-yl)-(4-methyl-pyridin-2-yl)-amine; compound (6) of table I

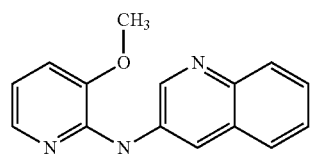

(3-Methoxy-pyridin-2-yl)-quinolin-3-yl-amine; compound (10) of table I; and

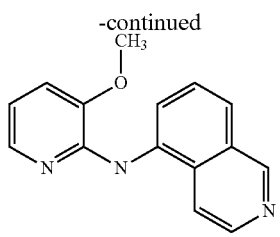

Isoquinolin-5-yl-(3-methoxy-pyridin-2-yl)-amine.

According to a particular embodiment, an additional subject-matter of the present invention is a compound of formula (Ia)

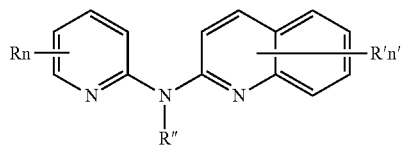

(Ia)

wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group, R″ is as defined above and is advantageously a hydrogen atom, n is as defined above and is advantageously 1, n′ is as defined above and is advantageously 1, R′ is a hydrogen atom, a halogen atom or a group chosen among a $(C_1-C_3)$alkyl group, a —NO$_2$ group, a $(C_1-C_3)$alkoxy group and a —NR$_1$R$_2$ group, R$_1$ and R$_2$ are a hydrogen atom or a $(C_1-C_3)$alkyl group, or one of its pharmaceutically acceptable salts, for use as an agent for preventing, inhibiting or treating AIDS.

According to another particular embodiment, an additional subject-matter of the present invention is a compound of formula (Ib)

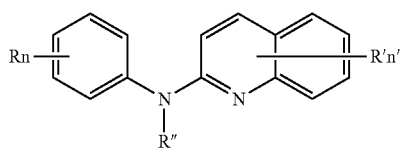

(Ib)

wherein:
R independently represent a hydrogen atom, a halogen atom or a group chosen among a $(C_1-C_3)$alkyl group, a —NR$_1$R$_2$ group, a $(C_1-C_3)$fluoroalkoxy group, a —NO$_2$ group, a phenoxy group and a $(C_1-C_4)$alkoxy group, R$_1$ and R$_2$ are independently a hydrogen atom or a $(C_1-C_3)$alkyl group, R″ is as defined above and is advantageously a hydrogen atom, n is as defined above and is preferably 1 or 2, n′ is as defined above and is preferably 1, R′ is a hydrogen atom, a halogen atom or a group chosen among a $(C_1-C_3)$alkyl group and a $(C_1-C_4)$alkoxy group, or one of its pharmaceutically acceptable salts, for use as an agent for preventing, inhibiting or treating AIDS.

According to another particular embodiment, an additional subject-matter of the present invention is a compound of formula (Ic)

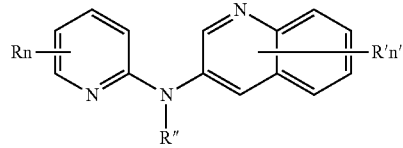

(Ic)

wherein:
R independently represent a hydrogen atom or a group chosen among a $(C_1-C_3)$alkyl group, a $(C_1-C_3)$fluoroalkyl group, a —NR$_1$R$_2$ group, a —COOR$_1$ group, a —NO$_2$ group and a $(C_1-C_3)$alkoxy group, R″ is as defined above and is advantageously a hydrogen atom, n is as defined above and is advantageously 1, n′ is as defined above and is advantageously 1, R′ is a hydrogen atom, R$_1$ and R$_2$ are independently a hydrogen atom or a $(C_1-C_3)$alkyl group, or one of its pharmaceutically acceptable salts, for use as an agent for preventing, inhibiting or treating AIDS.

According to another particular embodiment, an additional subject-matter of the present invention is a compound of formula (Id)

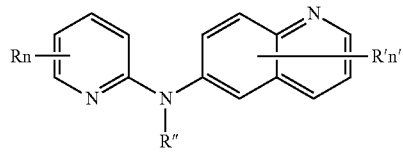

(Id)

wherein:
R independently represent a hydrogen atom or a group chosen among a $(C_1-C_3)$alkyl group, a $(C_1-C_3)$fluoroalkyl group and a $(C_1-C_3)$alkoxy group, R″ is as defined above and is advantageously a hydrogen atom, n is as defined above and is advantageously 1, n′ is as defined above and is advantageously 1, R′ is a hydrogen atom, or one of its pharmaceutically acceptable salts, for use as an agent for preventing, inhibiting or treating AIDS.

According to another particular embodiment, an additional subject-matter of the present invention is a compound of formula (Ie)

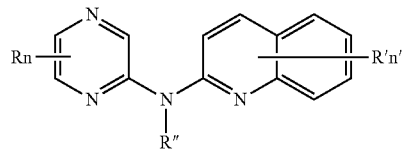

(Ie)

wherein:

R represents a hydrogen atom,

R" is as defined above and is advantageously a hydrogen atom, n is as defined above and is advantageously 1, n' is as defined above and is advantageously 1, R' is a hydrogen atom, a halogen atom or a group chosen among a $(C_1-C_3)$alkyl group and a $(C_1-C_3)$alkoxy group, or one of its pharmaceutically acceptable salt, for use as an agent for preventing, inhibiting or treating AIDS.

According to another particular embodiment, an additional subject-matter of the present invention is a compound of formula (If)

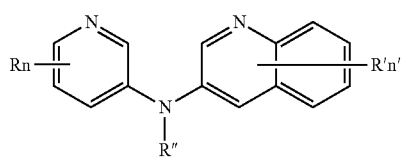

(If)

wherein:

R represents a hydrogen atom,

R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating AIDS.

According to another particular embodiment, an additional subject-matter of the present invention is a compound of formula (Ig)

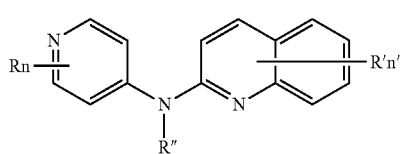

(Ig)

wherein:

R represents a hydrogen atom,

R" is as defined above and is advantageously a hydrogen atom, n is as defined above and is advantageously 1, n' is as defined above and is advantageously 1, R' is a hydrogen atom or a halogen atom, or one of its pharmaceutically acceptable salt, for use as an agent for preventing, inhibiting or treating AIDS.

According to another particular embodiment, an additional subject-matter of the present invention is a compound of formula (Ih)

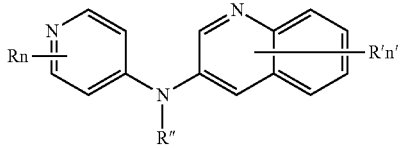

(Ih)

wherein:

R represents a hydrogen atom,

R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating AIDS.

According to another particular embodiment, an additional subject-matter of the present invention is a compound of formula (Ii)

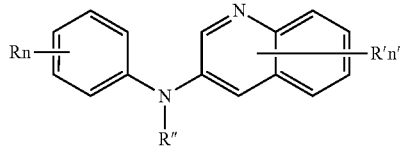

(Ii)

wherein:

R independently represent a hydrogen atom or a group chosen among a $(C_1-C_3)$fluoroalkoxy group and a $(C_1-C_3)$alkoxy group, R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating AIDS.

According to another particular embodiment, an additional subject-matter of the present invention is a compound of formula (Ij)

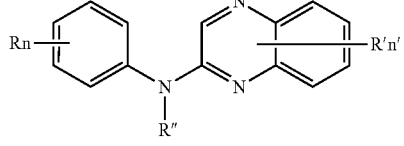

(Ij)

wherein:

R independently represent a hydrogen atom or a group chosen among a $(C_1-C_3)$fluoroalkoxy group and a $(C_1-C_3)$alkyl group, R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating AIDS.

According to another particular embodiment, an additional subject-matter of the present invention is a compound of formula (Ik)

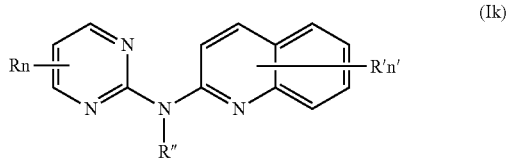

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a $(C_1-C_3)$alkyl group,
or one of its pharmaceutically acceptable salt,
for use as an agent for preventing, inhibiting or treating AIDS.

According to another particular embodiment, an additional subject-matter of the present invention is a compound of formula (Il)

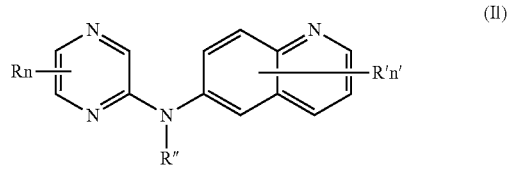

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Im)

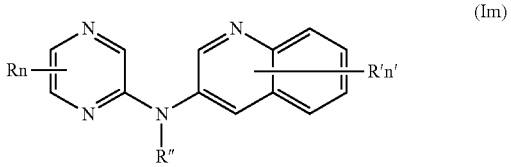

wherein:
R represents a hydrogen atom,
R" is as defined above and is advantageously a hydrogen atom,
n is as defined above and is advantageously 1, n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Io)

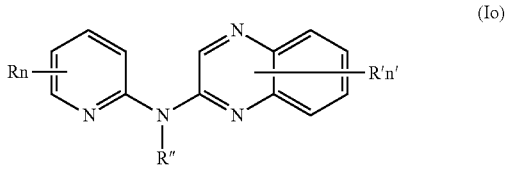

wherein:
R independently represent a hydrogen atom or a halogen atom or a group chosen among, a —$NO_2$ group, a —CN group and a $(C_1-C_3)$alkyl group, said alkyl being optionally mono-substituted by a hydroxyl group,
R" is as defined above and is advantageously a hydrogen atom,
n is as defined above and is advantageously 1,
n' is as defined above and is advantageously 1,
R' is a hydrogen atom, a halogen atom or a $(C_1-C_3)$ fluoroalkyl group,
or one of its pharmaceutically acceptable salt,
for use as an agent for preventing, inhibiting or treating AIDS.

According to another particular embodiment, an additional subject-matter of the present invention is a compound of formula (Ip)

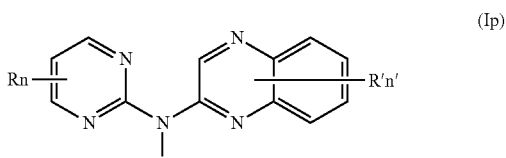

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Iq)

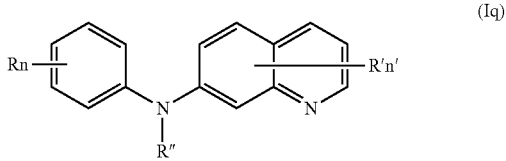

wherein:

R independently represent a hydrogen atom, a ($C_1$-$C_3$) alkoxy group or a ($C_1$-$C_3$)fluoroalkoxy group, R" is as defined above and is advantageously a hydrogen atom, n is as defined above and is advantageously 1, n' is as defined above and is advantageously 1, R' is a hydrogen atom or a group chosen among a —$NR_1R_2$ group, a N-methylpiperazinyl group, a ($C_1$-$C_3$) alkoxy group and a morpholino group, $R_1$ and $R_2$ are independently a hydrogen atom or a ($C_1$-$C_3$)alkyl group, or one of its pharmaceutically acceptable salt, for use as an agent for preventing, inhibiting or treating AIDS.

According to another particular embodiment, an additional subject-matter of the present invention is a compound of formula (Ir)

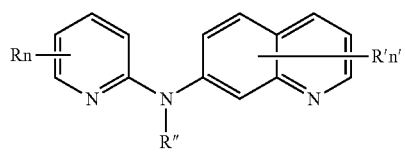

wherein:

R independently represent a hydrogen atom or a ($C_1$-$C_3$) alkyl group,

R" is as defined above and is advantageously a hydrogen atom, n is as defined above and is advantageously 1, n' is as defined above and is advantageously 1, R' is a hydrogen atom or a group chosen among a —$NR_1R_2$ group, a morpholino group and a ($C_1$-$C_3$)alkoxy group, $R_1$ and $R_2$ are independently a hydrogen atom or a ($C_1$-$C_3$)alkyl group, or one of its pharmaceutically acceptable salt, for use as an agent for preventing, inhibiting or treating AIDS.

According to another particular embodiment, an additional subject-matter of the present invention is a compound of formula (Iee)

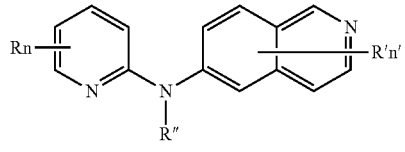

wherein:

R independently represent a hydrogen atom, a ($C_1$-$C_3$) alkyl group or a ($C_1$-$C_3$)fluoroalkyl group, R" is as defined above and is advantageously a hydrogen atom, n is as defined above and is advantageously 1, n' is as defined above and is advantageously 2, R' is a hydrogen atom or a ($C_1$-$C_3$)alkyl group, or one of its pharmaceutically acceptable salt, for use as an agent for preventing, inhibiting or treating AIDS.

Among the previous defined families of compounds of formulae (Ia) to (Iee), some are more particularly preferred for their use as an agent for preventing, inhibiting or treating AIDS. These preferred compounds particularly belong to formulae (Ia), (Ib), (Ic), (Ie) and (Io), as defined above or one of its pharmaceutically acceptable salts.

Accordingly the present invention further relates to a compound of formula (Ia), (Ib), (Ic), (Ie) and (Io), as defined above, for use as an agent for preventing, inhibiting or treating AIDS.

Thus, according to a more particular embodiment, the present invention particularly focuses on a compound of formula (Ia)

wherein:

R independently represent a hydrogen atom, a halogen atom or a group chosen among a ($C_1$-$C_3$)alkyl group, a ($C_1$-$C_3$)fluoroalkyl group, a hydroxyl group, a —CN group, a —COOH group and a ($C_1$-$C_3$)alkoxy group, R" is as defined above and more preferably is a hydrogen atom, n is as defined above and more preferably is 1, n' is as defined above, R' is a hydrogen atom, a halogen atom, a —$NO_2$ group or a ($C_1$-$C_3$)alkyl group, or one of its pharmaceutically acceptable salt, for use as an agent for preventing, inhibiting or treating AIDS.

Still according to this more particular embodiment, the present invention more preferably focuses on compounds of formula (Ia'),

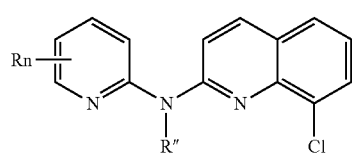

wherein,

R independently represent a hydrogen atom, a —CN group, a ($C_1$-$C_3$)alkyl group, a ($C_1$-$C_3$)fluoroalkyl group, a halogen atom or a hydroxyl group, R' is as defined in formula (Ia) and is preferably a halogen, a ($C_1$-$C_3$)alkyl group or a $NO_2$ group, R" is a hydrogen atom, n is 1 or 2 or one of its pharmaceutically acceptable salt, for use as an agent for preventing, inhibiting or treating AIDS.

According to another more particular embodiment, the present invention particularly focuses on a compound of formula (Ib)

wherein:

R independently represent a hydrogen atom, a halogen atom, a group chosen among a ($C_1$-$C_4$)alkyl group, a —$NR_1R_2$ group, a ($C_1$-$C_3$)alkoxy group and a ($C_1$-$C_3$) fluoroalkoxy group, $R_1$ and $R_2$ are independently a hydrogen atom or a ($C_1$-$C_3$)alkyl group, R" is as defined above and more preferably is a hydrogen atom, n is as defined above, n' is as defined above, R' is a hydrogen atom, halogen atom or a ($C_1$-$C_3$)alkyl group, or one of its pharmaceutically acceptable salt, for use as an agent for preventing, inhibiting or treating AIDS.

Still according to this more particular embodiment, the present invention more preferably focuses on compounds of formula (Ib'),

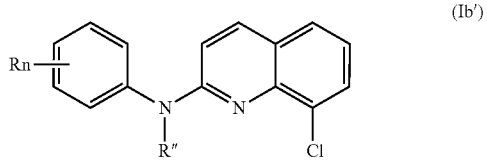

(Ib')

wherein:
R independently represent a hydrogen atom, a halogen atom, a group chosen among a ($C_1$-$C_3$)alkoxy group, a ($C_1$-$C_3$)fluoroalkoxy group,
R" is as defined above and more preferably is a hydrogen atom,
n is as defined above and more preferably is 1,
or one of its pharmaceutically acceptable salt,
for use as an agent for preventing, inhibiting or treating AIDS.

According to another more particular embodiment, the present invention particularly focuses on a compound of formula (Ic)
wherein:
R independently represent a hydrogen atom or a group chosen among a ($C_1$-$C_3$)fluoroalkyl group, a —$NO_2$ group, a —$NR_1R_2$ group and a ($C_1$-$C_3$)alkoxy group,
$R_1$ and $R_2$ are independently a hydrogen atom or a ($C_1$-$C_3$)alkyl group,
R" is as defined above and more preferably is a hydrogen atom,
n is as defined above and more preferably is 1,
n' is as defined above,
R' is a hydrogen atom,
or one of its pharmaceutically acceptable salt,
for use as an agent for preventing, inhibiting or treating AIDS.

According to another more particular embodiment, the present invention particularly focuses on a compound of formula (Ie)
wherein:
R represents a hydrogen atom,
R" is as defined above and more preferably is a hydrogen atom,
n is as defined above and more preferably is 1,
n' is as defined above,
R' is a hydrogen atom or a halogen atom,
or one of its pharmaceutically acceptable salt,
for use as an agent for preventing, inhibiting or treating.

According to another more particular embodiment, the present invention particularly focuses on a compound of formula (Io)
wherein:
R independently represent a hydrogen atom, a halogen atom or a group chosen among a ($C_1$-$C_3$)alkyl group and a —$NO_2$ group,
R" is as defined above and more preferably is a hydrogen atom,
n is 1, 2 or 3,
n' is as defined above,
R' is a hydrogen atom or a ($C_1$-$C_3$)fluoroalkyl group,
or one of its pharmaceutically acceptable salt, for use as an agent for preventing, inhibiting or treating AIDS.

In a particular embodiment, the present invention relates to a compound of formula (Ia), (Ic) or (Io) as defined above or one of its pharmaceutically acceptable salts, for use as an agent for preventing, inhibiting or treating AIDS.

According to a preferred embodiment of the present invention, the compound for use as an agent for preventing, inhibiting or treating AIDS, is chosen from:
(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine

(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N,1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N, 1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine
(112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine (151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N,1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine
and their pharmaceutically acceptable salts.

Among said compounds, compounds (1), (6), (33), (34), (35), (36), (37), (38), (42), (43), (44), (45), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140) and (141) are of particular interest.

The present invention therefore extends to compounds (1), (6), (33), (34), (35), (36), (37), (38), (42), (43), (44), (45), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140) and (141) or one of its pharmaceutically acceptable salts for use as an agent for preventing, inhibiting or treating AIDS.

Some of said preceding compounds are new and form part of the present invention: (1), (6), (33), (34), (35), (36), (37), (38), (42), (43), (44), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140), (141) and their pharmaceutically acceptable salts, such as hydrobromide, tartrate, citrate, trifluoroacetate, ascorbate, hydrochloride, tartrate, triflate, maleate, mesylate, formate, acetate and fumarate.

The compounds of formulae (I), (Ia), (Ib), (Ic), (Id), (Ie), (If), (Ig), (Ih), (Ii), (Ij), (Ik), (Il), (Im), (Io), (Ip), (Iq), (Ir) and (Iee) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

Among the compounds of formula (I), some of them are new and form part of the invention, as well as their pharmaceutically acceptable salts, such as hydrobromide, tartrate, citrate, trifluoroacetate, ascorbate, hydrochloride, tartrate, triflate, maleate, mesylate, formate, acetate and fumarate.

According to a particular embodiment, the present invention encompasses compounds of formula (Ig) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, R$_1$ and R$_2$ are independently a hydrogen atom or a $(C_1-C_3)$alkyl group, with the proviso that R and R' are not simultaneously a hydrogen atom, and when n and n' are 1 and R is a hydrogen atom then R' is not a —COOH group, or anyone of its pharmaceutically acceptable salt.

According to another particular embodiment, the present invention encompasses compounds of formula (If) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, R$_1$ and R$_2$ are independently a hydrogen atom or a $(C_1-C_3)$alkyl group, or anyone of its pharmaceutically acceptable salt.

According to another particular embodiment, the present invention encompasses compounds of formula (Ih) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, R$_1$ and R$_2$ are independently a hydrogen atom or a $(C_1-C_3)$alkyl group, or anyone of its pharmaceutically acceptable salt.

According to another particular embodiment, the present invention encompasses compounds of formula (Il) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, with the proviso that R and R' are not simultaneously a hydrogen atom, or anyone of its pharmaceutically acceptable salt.

According to another particular embodiment, the present invention encompasses compounds of formula (Im) wherein:

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$)alkyl group, with the proviso that when n and n' are 1 and R is a hydrogen atom, R' is not a chlorine atom, or anyone of its pharmaceutically acceptable salt.

For a sake of simplification, the following compounds and their corresponding definitions are called "new compounds".

According to another particular embodiment, the present invention encompasses compounds of formula (Ia), as such, wherein:

R" and n are as defined in formula (Ia), n' is 1,

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a —$NO_2$ group, a ($C_1$-$C_3$)fluoroalkoxy group and a ($C_1$-$C_3$)alkoxy group, R' is a hydrogen atom or a halogen atom or a group chosen among a ($C_1$-$C_3$)alkyl group, a —$COOR_1$ group, and a —CN group, and wherein:

with the proviso that when R and R' are not simultaneously a hydrogen atom, when n is 1, R is not a methyl group in ortho or para position with respect to Z, Z being N, when R' is a hydrogen atom, R is not a bromine atom or a chlorine atom, when R is a hydrogen atom, R' is not a methyl or ethyl group, a —COOH group, a $COOC_2H_5$ group or a bromine atom, said bromine atom being in ortho position of the bond linked to NR", or one of its pharmaceutically acceptable salt.

Still according to this particular embodiment, the present invention more particularly focuses on compounds of formula (Ia), as such, wherein, R independently represent a hydrogen atom, a ($C_1$-$C_3$) fluoroalkyl group, a halogen atom, a —CN group or a ($C_1$-$C_3$) alkyl group, R" is as defined in formula (Ia), R' is a hydrogen atom, a halogen atom or a —$NO_2$ group, n' is 1, n is 1, with the proviso that when n is 1, R is not a methyl group in ortho or para position with respect to Z, Z being N, R is not a bromine atom or a chlorine atom when R' is a hydrogen atom, or one of its pharmaceutically acceptable salt.

Still according to this particular embodiment, the present invention more preferably focuses on compounds of formula (Ia'), as such,

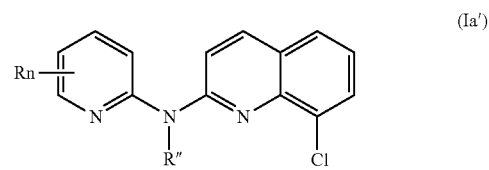

(Ia')

wherein,

R independently represent a hydrogen atom, a ($C_1$-$C_3$) alkyl group, a ($C_1$-$C_3$)fluoroalkyl group, a halogen atom or a hydroxyl group, R" is as defined in formula (Ia), n is 1 or 2, and preferably 1, or one of its pharmaceutically acceptable salt.

The present invention further relates to a compound of formula (Ib) as defined above, as such

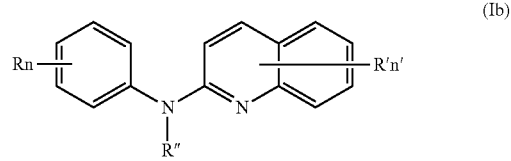

(Ib)

wherein:

R' and R" are as defined in formula (Ib), n is 1, and

R is a hydrogen atom or a ($C_1$-$C_3$)fluoroalkoxy group, or one of its pharmaceutically acceptable salt.

Still according to this particular embodiment, the present invention more particularly focuses on compounds of formula (Ib) wherein:

R is a hydrogen atom or a ($C_1$-$C_3$)fluoroalkoxy group,

R' is a hydrogen atom, a halogen atom or a ($C_1$-$C_4$)alkyl group,

R" is as defined in the formula (Ib), n' is 1 or 2 and is preferably 1, n is 1 or 2 and is preferably 1, or one of its pharmaceutically acceptable salt.

Still according to this particular embodiment, the present invention more particularly focuses on compounds of formula (Ib')

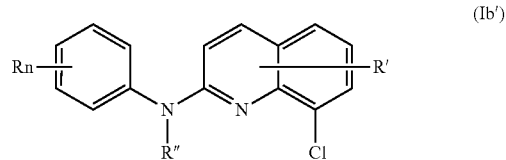

(Ib')

wherein:

R, R" and n are as defined in formula (Ib),

R' is as defined in formula (Ib), with the proviso that R' is different from a methyl group in position 4 on the quinoline, or one of its pharmaceutically acceptable salt.

Still according to this particular embodiment, the present invention more particularly focuses on compounds of formula (Ib")

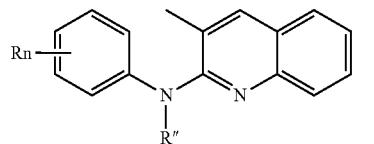

wherein:

R, R" and n are as defined in formula (Ib), with the proviso that when n is 1, R is not a hydrogen atom, a methyl group in para of the bond linked to NR", a ethoxy group in para of the bond linked to NR", nor a fluorine atom in para of the bond linked to NR", or one of its pharmaceutically acceptable salt.

According to another particular embodiment, the present invention encompasses compounds of formula (Ic), as such, wherein:

R independently represent a hydrogen atom, a halogen atom or a group chosen among a $(C_1$-$C_3)$alkyl group, a —CN group, a hydroxyl group, a —COOR$_1$ group, a $(C_1$-$C_3)$fluoroalkyl group, a —NO$_2$ group, a —NR$_1$R$_2$ group and a $(C_1$-$C_3)$alkoxy group, R$_1$ and R$_2$ are independently a hydrogen atom or a $(C_1$-$C_3)$alkyl group, n is 1 or 2, and advantageously 1, n' is 1 or 2, R" is as defined in formula (Ic), R' is a hydrogen atom or a group chosen among a $(C_1$-$C_3)$alkyl group, a —NO$_2$ group, a —NR$_1$R$_2$ group and a $(C_1$-$C_3)$alkoxy group, with the proviso that R and R' are not simultaneously a hydrogen atom, R is not a bromine atom when R' is a hydrogen atom, or one of its pharmaceutically acceptable salt.

Still according to this particular embodiment, the present invention more particularly focuses on compounds of formula (Ic), as such, wherein, R is a hydrogen atom or a —NO$_2$ group, n is 1, R', R" and n' are as defined in formula (Ic), and R' is preferably a $(C_1$-$C_3)$alkyl group or a hydrogen atom, or one of its pharmaceutically acceptable salt.

The present invention further relates to a compound of formula (Ie) as defined above, as such

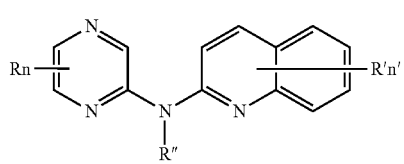

wherein:

R, R', R" n and n' are as defined in formula (I), with the proviso that when R is a hydrogen atom, R' is not a bromine atom, or one of its pharmaceutically acceptable salt.

According to another particular embodiment, the present invention encompasses compounds of formula (Io), as such, wherein:

R independently represent a hydrogen atom, a halogen atom or a group chosen among a $(C_1$-$C_3)$alkyl group, a —CN group, a hydroxyl group, a —COOR$_1$ group, a $(C_1$-$C_3)$fluoroalkyl group, a $(C_1$-$C_3)$fluoroalkoxy group, a —NO$_2$ group, a —NR$_1$R$_2$ group and a $(C_1$-$C_3)$alkoxy group, R$_1$ and R$_2$ are independently a hydrogen atom or a $(C_1$-$C_3)$alkyl group, n is 1, 2 or 3, n' is 1 or 2, R' is a hydrogen atom or a group chosen among a $(C_1$-$C_3)$alkyl group, a halogen atom, a hydroxyl group, a —COOR$_1$ group, a —NO$_2$ group, a —NR$_1$R$_2$ group, a $(C_1$-$C_3)$alkoxy group and a —CN group, R" is a hydrogen atom or a $(C_1$-$C_4)$alkyl group, with the proviso that when R is a hydrogen atom and n' is 1, R' is not a hydroxyl group, or one of its pharmaceutically acceptable salt.

Still according to this particular embodiment, the present invention more particularly focuses on compounds of formula (Io'), as such, wherein

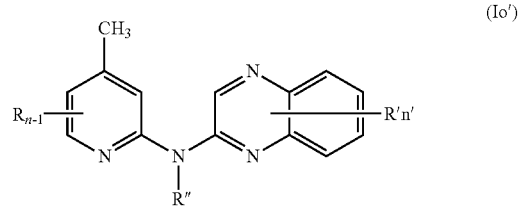

wherein:

n is 1, 2 or 3, n' is 1 or 2,

R independently represent a hydrogen atom, a halogen atom or a group chosen among a $(C_1$-$C_3)$alkyl group, a —CN group, a hydroxyl group, a —COOR$_1$ group, a $(C_1$-$C_3)$fluoroalkyl group, a $(C_1$-$C_3)$fluoroalkoxy group, a —NO$_2$ group, a —NR$_1$R$_2$ group and a $(C_1$-$C_3)$alkoxy group, and is preferably a —NO$_2$ group, a hydrogen atom or a halogen atom, R' is a hydrogen atom or a group chosen among a $(C_1$-$C_3)$alkyl group, a halogen atom, a hydroxyl group, a —COOR$_1$ group, a —NO$_2$ group, a —NR$_1$R$_2$ group, a $(C_1$-$C_3)$alkoxy group and a —CN group, a $(C_1$-$C_3)$fluroralkyl group, and preferably is a hydrogen atom or a $(C_1$-$C_3)$fluoroalkyl group, R$_1$ and R$_2$ are as defined in formula (Io), R" is a hydrogen atom or a $(C_1$-$C_4)$alkyl group, or one of its pharmaceutically acceptable salt.

Among said compounds as such, compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts are of particular interest.

The present invention therefore extends to compounds (1), (2), (5)-(8), (10)-(16), (18), (21)-(44), (46)-(75), (77)-

(84), (86)-(119), (121), (124)-(130), (132), (135)-(141), (143)-(147), (149)-(168) and their pharmaceutically acceptable salts, as such.

More preferably, compounds (8), (75), (77)-(84), (86)-(104), (109)-(117), (155)-(158) and their pharmaceutically acceptable salts are of particular interest.

The present invention therefore extends more preferably to compounds (8), (75), (77)-(84), (86)-(104), (109)-(117), (155)-(158) and their pharmaceutically acceptable salts, such as hydrobromide, tartrate, citrate, trifluoroacetate, ascorbate, hydrochloride, tartrate, triflate, maleate, mesylate, formate, acetate and fumarate.

Still more preferably, the present invention extends to compounds (75), (77), (78), (79), (80), (81), (82), (86), (87), (88), (90), (92), (96), (104), (109), (112), and their pharmaceutically acceptable salts, such as hydrobromide, tartrate, citrate, trifluoroacetate, ascorbate, hydrochloride, tartrate, triflate, maleate, mesylate, formate, acetate and fumarate.

The new compounds of the present invention, i.e. compounds of formulae (Ia), (Ic), (Io), (Ib), (Ib'), (Ib") and (Ie) and the specific compounds as listed above, are not only useful as agent for inhibiting, preventing or treating AIDS but can also be useful for inhibiting, preventing or treating premature aging and for inhibiting, preventing or treating cancer, and more particularly colorectal cancer, pancreatic cancer, lung cancer including non-small cell lung cancer, breast cancer, bladder cancer, gall bladder cancer, liver cancer, thyroid cancer, melanoma, uterine/cervical cancer, oesophageal cancer, kidney cancer, ovarian cancer, prostate cancer, head and neck cancer and stomach cancer, etc.

According to an aspect of the invention said compounds may be useful to inhibit, prevent and/or treat diseases with premature aging and that are likely related to an aberrant splicing of the nuclear lamin A gene. Among all, said disease may include Hutchinson Guilford Progeria Syndrome (HGPS), progeria, premature aging associated with HIV infection, muscular dystrophy, Charcot-Marie-Tooth disorder, Werner syndrome, but also atherosclerosis, insulin resistant type II diabetes, cataracts, osteoporosis and aging of the skin such as restrictive dermopathy.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 (above, See EMBODIMENT I). The chemical structures and spectroscopic data of some compounds of formula (I) of the invention are illustrated respectively in the following Table I (above) and Table II (above).

The following examples are provided as illustrations and in no way limit the scope of this invention.

The following examples illustrate in detail the preparation of some compounds according to the invention. The structures of the products obtained have been confirmed by NMR spectra.

Embodiment II: Examples

According to route (A), the compound of formula (III) is placed in a protic solvent such as tert-butanol. The compound of formula (IV) is then added in a 1.1 molar ratio with respect to the compound of formula (III) in presence of $Cs_2CO_3$, in a 2.8 molar ratio, in the presence of Xantphos (4,5-Bis(diphenylphosphino)-9,9-dimethylxanthene), in a 2 mol % amount relative to the total amount of compound of formula (III), and in the presence of $Pd(OAc)_2$, in a 2 mol % amount relative to the total amount of compound of formula (III). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, fitrered and concentrated under reduced pressure. The residue could then be purified by column chromatography on silica gel to yield pure compounds (6), (43), (77), (80), (90), (112) and (136).

According to route (B), the compound of formula (V) is placed in a protic solvent such as tert-butanol. The compound of formula (VI) is then added in a 1.1 molar ratio with respect to the compound of formula (V) in presence of $Cs_2CO_3$ in a 2.8 molar ratio, in the presence of Xantphos (4,5-Bis(diphenylphosphino)-9,9-dimethylxanthene) in a 2 mol % amount relative to the total amount of compound of formula (V), and in the presence of a $Pd(OAc)_2$, in a 2 mol % amount relative to the total amount of compound of formula (V). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compound (106).

Example 1: Compound (6) of the Table I

According to route (A), a mixture of 2,8-dichloroquinoline (1.5 g) and 2-amino-4methylpyridine (904 mg), $Pd(OAc)_2$ (34 mg), XantPhos (88 mg) and $Cs_2CO_3$ (7.0 g) in 30 mL of t-BuOH gave compound (6) (1.3 g).

$^1$H NMR (300 MHz, DMSO) δ 10.23 (s, 1H), 8.96 (s, 1H), 8.18 (d, J=8.8, 2H), 7.78 (dd, J=7.7, 13.7, 2H), 7.46 (d, J=8.9, 1H), 7.31 (t, J=7.8, 1H), 6.86 (d, J=4.3, 1H), 2.37 (s, 3H).

$^{13}$C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24.

MS (ESI) [M+H]$^+$=270

Example 2: Compound (43) of the Table I

According to route (A), a mixture of 2,8-dichloroquinoline (394 mg) and 2-amino-5fluoropyridine (246 mg), $Pd(OAc)_2$ (9 mg), XantPhos (23 mg) and $Cs_2CO_3$ (1.8 g) in 8 mL of t-BuOH gave compound (43) (320 mg).

$^1$H NMR (300 MHz, DMSO) δ 10.41 (s, 1H), 9.08 (dd, J=4.1, 9.3, 1H), 8.31 (d, J=2.9, 1H), 8.20 (d, J=8.9, 1H), 7.88-7.70 (m, 3H), 7.44 (d, J=8.9, 1H), 7.32 (t, J=7.8, 1H).

$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.

MS (ESI) [M+H]$^+$=274

Example 3: Compound (77) of the Table I

According to route (A), a mixture of 2,8-dichloroquinoline (985 mg) and p-anisidine (677 mg), $Pd(OAc)_2$ (22 mg), XantPhos (58 mg) and $Cs_2CO_3$ (4.6 g) in 20 mL of t-BuOH gave compound (77) (629 mg).

$^1$H NMR (300 MHz, CDCl$_3$) δ 7.83 (d, J=8.8, 1H), 7.70 (d, J=7.6, 1H), 7.59 (d, J=8.6, 2H), 7.52 (d, J=7.3, 1H), 7.16 (t, J=7.7, 1H), 6.94 (d, J=8.4, 3H), 6.86 (d, J=8.8, 1H), 3.82 (s, 3H).

$^{13}$C NMR (75 MHz, CDCl$_3$) δ 156.40, 155.54, 144.29, 138.09, 132.96, 130.44, 129.99, 126.61, 125.22, 123.29, 122.66, 114.73, 112.16, 55.74.
MS (ESI) [M+H]$^+$=285

Example 4: Compound (80) of the Table I

According to route (A), a mixture of 2-chloro-3methylquinoline (885 mg) and 4-(trifluoromethoxy)aniline (743 µL), Pd(OAc)$_2$ (22 mg), XantPhos (58 mg) and Cs$_2$CO$_3$ (4.6 g) in 20 mL of t-BuOH gave compound (80) (1.3 g).
$^1$H NMR (300 MHz, CDCl$_3$) δ 7.92 (d, J=8.9 Hz, 2H), 7.84 (d, J=8.3 Hz, 1H), 7.78 (s, 1H), 7.62 (d, J=8.0 Hz, 1H), 7.57 (t, J=7.7 Hz, 1H), 7.32 (t, J=7.4 Hz, 1H), 7.24 (d, J=8.7 Hz, 2H), 6.53 (s, 1H), 2.42 (s, 3H).
$^{13}$C NMR (75 MHz, CDCl$_3$) δ 152.46, 146.25, 143.86, 139.33, 136.83, 128.93, 126.96, 126.71, 124.75, 123.56, 121.88, 120.44, 119.95, 17.77.
MS (ESI) [M+H]$^+$=319

Example 5: Compound (90) of the Table I

According to route (A), a mixture of 2,8-dichloroquinoline (984 mg) and 4-(trifluoromethoxy)aniline (743 µL), Pd(OAc)$_2$ (22 mg), XantPhos (58 mg) and Cs$_2$CO$_3$ (4.6 g) in 20 mL of t-BuOH gave compound (90) (1.1 g).
$^1$H NMR (300 MHz, CDCl$_3$) δ 7.84 (d, J=9.1, 2H), 7.79 (d, J=8.9, 1H), 7.67 (dd, J=1.2, 7.6, 1H), 7.48 (dd, J=1.1, 8.0, 1H), 7.18 (s, 3H), 6.89 (s, 1H), 6.75 (d, J=8.9, 1H).
$^{13}$C NMR (75 MHz, CDCl$_3$) δ 153.88, 144.30, 143.91, 139.00, 138.25, 131.13, 130.13, 126.55, 125.42, 123.45, 122.50, 122.17, 120.49, 119.10, 113.24.
MS (ESI) [M+H]$^+$=339

Example 6: compound (106) of the table I

According to route (B), a mixture of 3-aminoquinoline (316 mg) and 2-chloro-3nitropyridine (315 mg), Pd(OAc)$_2$ (22 mg), XantPhos (58 mg) and Cs$_2$CO$_3$ (4.6 g) in 20 mL of t-BuOH gave compound (106) (374.1 mg).
$^1$H NMR (300 MHz, DMSO) δ 10.24 (s, 1H), 9.06 (d, J=2.3, 1H), 8.65 (d, J=1.8, 1H), 8.60 (d, J=8.3, 1H), 8.56 (d, J=4.5, 1H), 7.97 (dd, J=8.2, 14.4, 2H), 7.69 (t, J=6.9, 1H), 7.59 (t, J=7.4, 1H), 7.08 (dd, J=4.6, 8.3, 1H).
MS (ESI) [M+H]$^+$=267

Example 7: Compound (112) of the Table I

According to route (A), a mixture of 2,8-dichloroquinoline (958 mg) and aminopyrazine (522 mg), Pd(OAc)$_2$ (22 mg), XantPhos (58 mg) and Cs$_2$CO$_3$ (4.6 g) in 20 mL of t-BuOH gave compound (112) (728 mg).
$^1$H NMR (300 MHz, DMSO) δ 10.58 (s, 1H), 10.26 (s, 1H), 8.36 (s, 1H), 8.27 (s, 2H), 7.91-7.74 (m, 2H), 7.50 (d, J=8.8, 1H), 7.37 (t, J=7.6, 1H).
$^{13}$C NMR (75 MHz, DMSO) δ 152.94, 150.19, 142.48, 142.18, 138.20, 137.55, 135.74, 129.71, 126.99, 125.35, 123.84, 114.75.
MS (ESI) [M+H]$^+$=255

Example 7: Compound (136) of the Table I

According to route (A), a mixture of 2-chloroquinoxaline (82.0 mg) and 2-amino-4methylpyridine (59.4 mg), Pd(OAc)$_2$ (2.2 mg), XantPhos (5.8 mg) and Cs$_2$CO$_3$ (456 mg) in 2 mL of t-BuOH gave compound (136) (35.4 mg).

$^1$H NMR (300 MHz, CDCl$_3$) δ 9.02 (s, 1H), 8.70 (s, 1H), 8.30 (s, 1H), 8.20 (d, J=5.1, 1H), 7.94 (d, J=8.1, 1H), 7.84 (d, J=8.2, 1H), 7.64 (t, J=7.6, 1H), 7.49 (t, J=8.1, 1H), 6.83 (d, J=5.0, 1H), 2.43 (s, 3H).
$^{13}$C NMR (75 MHz, CDCl$_3$) δ 153.28, 150.20, 148.55, 147.40, 140.93, 139.83, 138.35, 130.44, 129.16, 127.18, 126.28, 119.70, 113.75, 21.87.
MS (ESI) [M+H]$^+$=237

Example 8: Method for Synthesizing the Compounds of the Present Invention

Typical Procedure for Pd-Catalysed Aminations

To a solution of halogeno compound (0.5 mmol, 1 equiv) in tert-butanol (2 mL) were added the amino moiety (0.55 mmol, 1.1 equiv), Cs$_2$CO$_3$ (456 mg, 1.4 mmol, 2.8 equiv), Xantphos (4,5-Bis(diphenylphosphino)-9,9-dimethylxanthene) (5.8 mg, 0.01 mmol, 2 mol %), Pd(OAc)$_2$ (2.2 mg, 0.01 mmol, 2 mol %). The reaction mixture was heated at 90° C. and stirred for 20 h under argon. The reaction mixture was concentrated under reduced pressure. The residue was purified by column chromatography on silica gel to yield pure compounds.

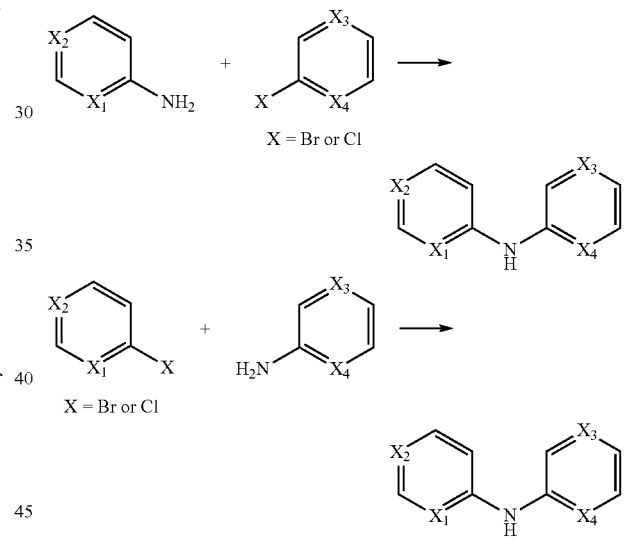

For example this procedure permitted to synthesize the following compounds:

Isoquinolin-5-yl-(3-methoxy-pyridin-2-yl)-amine $^1$H NMR (300 MHz, CDCl$_3$) δ 9.24 (s, 1H), 8.66 (dd, J=1.7, 6.8, 1H), 8.55 (d, J=6.0, 1H), 7.85 (d, J=5.0, 1H), 7.76 (d, J=6.0, 1H), 7.69-7.58 (m, 2H), 7.53 (s, 1H), 7.06 (d, J=7.7, 1H), 6.78 (dd, J=5.1, 7.8, 1H), 3.99 (s, 3H).
$^{13}$C NMR (75 MHz, CDCl$_3$) δ 153.23, 146.60, 142.97, 142.79, 138.53, 134.82, 129.53, 129.13, 127.95, 121.66, 119.82, 115.18, 115.05, 114.09, 100.15, 55.80.

(8-Chloro-quinolin-2-yl)-(4-methyl-pyridin-2-yl)-amine: (6) of the table I $^1$H NMR (300 MHz, CDCl$_3$) δ 8.82 (s, 1H), 8.17 (d, J=5.1, 1H), 8.09 (s, 1H), 7.98 (d, J=8.9, 1H), 7.76 (dd, J=1.2, 7.6, 1H), 7.61 (dd, J=1.0, 8.0, 1H), 7.26 (t, J=7.8, 2H), 7.15 (d, J=8.7, 1H), 6.83 (d, J=5.0, 1H), 2.46 (s, 3H).

$^{13}$C NMR (75 MHz, CDCl3) δ 153.52, 153.14, 149.90, 147.43, 143.68, 138.08, 131.37, 129.98, 126.56, 125.58, 123.58, 119.17, 114.52, 114.02, 21.84.

(3-Methoxy-pyridin-2-yl)-quinolin-3-yl-amine: (10) of the table I $^1$H NMR (300 MHz, DMSO) δ 9.17 (d, J=2.5, 1H), 8.97 (d, J=2.4, 1H), 8.79 (s, 1H), 7.94-7.79 (m, 3H), 7.58-7.46 (m, 2H), 7.31 (d, J=7.9, 1H), 6.88 (dd, J=5.0, 7.9, 1H), 3.94 (s, 3H).

Pharmalogical Data

The compounds of the invention have been the subject of pharmacological tests which have demonstrated their relevance as active substances in therapy and in particular for preventing, inhibiting or treating AIDS.

Example 9: Development of IDC16 Derivative Compounds

The inventors have shown that compound IDC16 (BAKKOUR et al., cited above, 2007) interacts functionally with the SF2/ASF complex and thus contributes to blocking alternative splicing during HIV replication, leading to the termination of the production of Tat protein.

Accordingly, the family of polycyclic indoles, to which compound IDC16 belongs, is known to exhibit the properties of DNA intercalating agents. Such compounds thus present a risk in terms of undesirable side effects.

The inventors thus sought to develop novel molecules exhibiting activity comparable to IDC16, in terms of activity inhibiting HIV splicing, but while not exhibiting the characteristics of DNA intercalating agents.

In their initial hypothesis, the inventors considered that the two polar heterocycles at the two ends of compound IDC16 were associated with its activity and that the two median rings were of less importance.

Based on this hypothesis, the inventors considered that:
the nitrogen of the indoline and of the D ring of IDC16 might act as acceptors of hydrogen bonds;
the N-methylated 4-pyridinone motif might be preserved in the analogues;
the flat tetracyclic geometry was not optimal and it might be wise to replace the B and C rings by other motifs to limit DNA intercalating properties.

Example 10: Inhibition of HIV-1 Production in Infected Peripheral Blood Mononuclear Cells (PBMCs)

Material and Methods

The first determination is that of the concentration of compound that exhibits the fewest side effects in terms of cell viability and progression of the cell cycle.

Within this framework, the peripheral blood mononuclear cells (PBMCs) of healthy donors are isolated by centrifugation on a FICOLL gradient. The cells are then cultivated to a density of 2.5×10$^6$ cells/ml with RPMI medium supplemented with 1% inactivated human AB serum, then incubated at 37° C., 5% CO$_2$ for an additional hour. The peripheral blood mononuclear cells are then recovered and cultivated for two days in RPMI medium supplemented with 10% fetal calf serum.

A standard experiment using 96 plates to test 30 molecules in triplicates including positive and negative controls, is performed as follows:

50 10$^6$ Ficoll purified PBMCs (10% DMSO 90% FCS) are washed with RPMI 10% FCS and resuspended in 25 ml of RPMI 10% FCS, glutamax containing 1000 U/ml of IL2 and 5 µg/ml PHA. The cells are then incubated for 3 days at 37° C. before to be washed with 50 ml PBS then with 50 ml RPMI 10% FCS. The cells are resuspended in 100 µl of RPMI 10% FCS containing 100 U/ml IL2 and seeded in 96 wells (1.5 10$^5$ cells/well). Viral infection is performed with 1 ng of AdaM/well. 100 µl of tested molecules at concentration of 10 µM are added to each well. Virus production is determined by p24 antigen immunosorbent assays after 3 and 6 days of infection (Kit Innogenetics). Typically PBMCs are prepared from several healthy donors (around 11 different donors). Dose response curves were then established with selected compounds to determine IC$_{50}$.

Protocol for Cytotoxicity:

To evaluate the cytotoxicity of different compounds we used the same protocol as above to seed the HOS-CD4$^+$-CCR5$^+$ cells or PBMCs in a final volume of 100 µl without adding the virus. After an incubation for 48 h at 37° C., the medium was removed and cells were incubated with 20 µl of CellTiter96 AqueousOne solution to determine the number of viable cells in proliferation and cytotoxicity assays (Promega). CellTiter96 AqueousOne is a colorimetric assay solution that has many advantages compared to MTT assays and gives us satisfactory results.

We have also evaluated the effect of selected molecules on CD4 and CD8 proliferation using the division tracking dye carboxyfluorescein diacetate succinimidyl ester (CFSE) (Invitrogen).

Results

| Compound number | IC$_{50}$ in nM | Inhibition of p24 production in HIV infected PBMCs from different donors |
|---|---|---|
| Formula (Ia) | | |
| 1 | nd | 4 out 6 donnors |
| 6 | 0.1 | 9 out 14 donnors |
| 33 | nd | 5 out 6 donnors |
| 34 | nd | 6 out 8 donnors |
| 35 | nd | 6 out 8 donnors |
| 36 | nd | 6 out 8 donnors |
| 37 | nd | 4 out 6 donnors |
| 38 | nd | 4 out 6 donnors |
| 42 | nd | 4 out 6 donnors |
| 43 | 0.1 | 8 out of 10 donnors |
| 44 | nd | 4 out 6 donnors |
| 45 | nd | 4 out of 4 donnors |
| 46 | nd | 4 out of 4 donnors |
| 48 | nd | 4 out 4 donnors |
| 50 | nd | 4 out of 4 donnors |
| 64 | nd | 5 out of 5 donnors |
| 68 | nd | 4 out of 4 donnors |
| 69 | nd | 4 out of 4 donnors |
| 70 | nd | 4 out of 4 donnors |
| 71 | nd | 4 out of 4 donnors |
| 72 | nd | 4 out of 4 donnors |
| 73 | nd | 4 out of 4 donnors |
| 74 | nd | 4 out of 4 donnors |
| Formula (Ib) | | |
| 75 | nd | 6 out of 7 donnors |
| 77 | 0.05 | 11 out of 13 donnors |
| 78 | nd | 7 out of 8 donnors |
| 79 | nd | 7 out of 8 donnors |
| 80 | 1 | 7 out of 8 donnors |
| 81 | nd | 4 out of 4 donnors |
| 82 | nd | 4 out of 4 donnors |
| 86 | nd | 3 out of 4 donnors |

-continued

| Compound number | IC$_{50}$ in nM | Inhibition of p24 production in HIV infected PBMCs from different donors |
|---|---|---|
| 87 | nd | 4 out of 4 donnors |
| 88 | nd | 4 out of 4 donnors |
| 90 | 0.1 | 8 out of 10 donnors |
| 92 | nd | 3 out of 5 donnors |
| 96 | nd | 5 out of 6 donnors |
| 104 | nd | 4 out of 4 donnors |
| Formula (Ic) | | |
| 106 | 0.5 | 6 out of 6 donnors |
| Formula (Ie) | | |
| 109 | nd | 8 out of 8 donnors |
| 112 | 0.1 | 12 out of 13 donnors |
| Formula (Io) | | |
| 136 | nd | 6 out of 8 donnors |
| 139 | nd | 4 out of 4 donnors |
| 140 | nd | 4 out of 4 donnors |
| 141 | nd | 4 out of 4 donnors |

Example 11: Inhibition of HIV-1 Production in Infected Macrophages

In order to generalize the HIV-1 replication effect of the molecules of the present invention to other cell types, we examined various steps of the viral cycle in cells treated with the various drug at a concentration of 5 µM and submitted to one-round infection.

For such experiences, macrophages can be infected by the Ada-M R5 HIV strain and treated for 18 hours with various concentrations of the compounds of the present invention. The culture medium is then eliminated and the cells washed with an abundance of PBS. The cells are then cultivated under normal conditions. The culture medium and the cells are then collected at days 4, 7 and 14. Finally, virus replication is measured indirectly by determining the level of p24 antigen in both the culture supernatant and the cellular lysate by the ELISA method. In parallel, cell viability of the macrophages in the presence of the compounds of of the present invention is measured as before.

For this purpose, we exposed HOS-CD4$^+$—CCR5$^+$ cells to defective virions obtained by cotransfecting 293T cells with a plasmid encoding the R5 envelope of the AD8 strain and another plasmid containing the entire HIV-1 genome mutated in the envelope gene and harbouring a luciferase marker gene fused to nef (Connor R I, Chen B K, Choe S, Landau N R. (1995) Vpr is required for efficient replication of human immunodeficiency virus type-1 in mononuclear phagocytes. Virology 206: 935-944). The amounts of luciferase activity in cells infected with these virions reflect both the number of integrated proviruses and expression of multiply spliced species encoding nef/luc. Two days post-infection, luciferase activity in HOS-CD4+-CCR5+ infected cells was measured.

The results are shown below:

| Compound | Results |
|---|---|
| (121) of the table I | + |
| (2) of the table I | − |
| (6) of the table I | + |
| (5) of the table I | − |
| (10) of the table I | + |
| (14) of the table I | − |

| Compound | Results |
|---|---|
| [structure: bis(5-CF3-pyridin-2-yl)amino-dimethylisoquinoline] | − |
| [structure: pyridin-2-ylamino dimethyl isoquinolinone] | − |
| [structure: 3-methoxy-pyridin-2-ylamino dimethyl isoquinolinone] | − |
| [structure: 3-methoxy-pyridin-2-ylamino isoquinolin-5-yl] | + |
| [structure: pyridin-3-ylamino chloroquinoline] | − |

The results established that the compounds of the present invention show a luciferase inhibitory effect, thus showing that these compounds inhibit viral RNA splicing.

A further object of the invention consists of a pharmaceutical composition comprising at least one compound of formula (Ib) or (Ie) or anyone of compounds (8), (75), (77)-(84), (86)-(104), (109)-(117), (155)-(158) and their pharmaceutically acceptable salts, such as hydrobromide, tartrate, citrate, trifluoroacetate, ascorbate, hydrochloride, tartrate, triflate, maleate, mesylate, formate, acetate and fumarate and, optionally, a pharmaceutically acceptable support.

As examples of pharmaceutically acceptable supports, the composition can include emulsions, microemulsions, oil in water emulsions, anhydrous lipids and water in oil emulsions or other types of emulsions.

The inventive composition can further include one or more additives such as diluents, excipients, stabilizers and preservatives. Such additives are well known to those skilled in the art and are described notably in "*Ullmann's Encyclopedia of Industrial Chemistry, 6$^{th}$ Ed.*" (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

Still a further object consists of the use of at least one compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention in preparing a drug to treat, in a subject, a disease resulting from at least one splicing anomaly.

Therefore, the present invention relates to a compound of formula (I), (Ia), (Ib), (Ic), (Id), (Ie), (If), (Ig), (Ih), (Ii), (Ij), (Ik), (Ti), (Im), (Io), (Ip), (Iq), (Ir) or (Iee) as defined above, and compounds (1) to (168) as defined above, or one of its pharmaceutically acceptable salts according to the present invention for preparing a drug to treat, in a subject, a disease resulting from at least one splicing anomaly.

As used in the present application, the term "subject" refers to a mammal such as a rodent, cat, dog, primate or human, preferably said subject is a human.

Preferably, the inventive compounds have the ability to inhibit pre-messenger RNA splicing processes that are either constitutive or, more specifically, dependent on regulating sequences known as an ESE (exonic splicing enhancer), ISE (intronic splicing enhancer), ESS (exonic splicing silencer) and ISS (intronic splicing silencer).

In a particularly preferred way, splicing processes are either constitutive and/or or dependent on ESE regulating sequences.

Preferably, the present invention relates to the use of the at least one compound of formula (I), (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, or one of its pharmaceutically acceptable salts according to the present invention, and more particularly of formula (Ia), (Ib), (Ic), (Ie) and (Io) as described above for preparing a drug to treat, in a subject, AIDS.

Therefore, the present invention relates to a one of said compounds, and more particularly to a compound (1) to (168) or one of its acceptable salts for treating AIDS.

Another object of the invention relates to a therapeutic method for treating a subject for a genetic disease resulting from splicing anomalies comprising the administration of a therapeutically effective quantity of a compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, more particularly of formula (Ia), (Ib), (Ic), (Ie) and (Io) as described above, and even more particularly of at least one compound (1) to (168) or one of its acceptable salts.

Preferably, said genetic disease resulting from splicing anomalies is AIDS.

A "therapeutically effective quantity" means a quantity that induces inhibition of the splicing of the pre-mRNAs of interest. Those skilled in the art will be able to determine said therapeutically effective quantity based on their general knowledge and on the methods described in the examples.

The compounds can be administered by any mode of administration such as, for example, by intramuscular, intravenous or oral route, etc.

In one embodiment according to the invention, said composition further includes an excipient making it possible to formulate the inventive compounds in such a way that said composition is provided in solid or liquid form to be prepared and administered by intravenous route.

The inventive compounds preferably will be administered by intravenous route at a concentration of 80-100 mg/m². The concentration will be chosen by those skilled in the art according to the organ or tissue to be treated, the state of advancement of the disease and the targeting mode used.

Embodiment III (Premature Aging)

The present invention of EMBODIMENT III is based on a novel approach based on the inhibition of aberrant splicing leading to progerin production.

The truncated Lamin A protein lacking the last 150 base pairs of exon 11 also called "progerin", acting as a dominant negative mutant, is predicted to be responsible for the characteristic manifestations seen in HGPS patients. Given that similar alteration of lamin A/C splicing was observed in aged individuals, it is proposed here that therapeutic molecules that interfere with the usage of the cryptic splice site will prevent side effects associated with accumulation of progerin during physiological aging. In other words, the compounds according to the present invention prevent usage of the cryptic 5' splice site in exon 11 of LMNA, allowing overcoming deleterious effect associated with progerin.

According to a first aspect, a subject-matter of the present invention relates to a compound of formula (I)

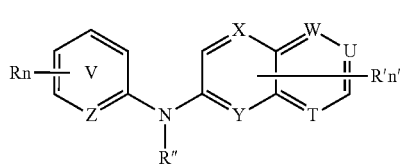

(I)

wherein:

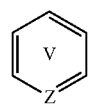

means an aromatic ring wherein V is C or N and when V is N, V is in ortho, meta or para of Z, i.e. forms respectively a pyridazine, a pyrimidine or a pyrazine group, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group and a (C$_1$-C$_3$)alkyl group, said alkyl being optionally mono-substituted by a hydroxyl group, R$_1$ and R$_2$ are independently a hydrogen atom or a (C$_1$-C$_3$)alkyl group, n is 1, 2 or 3, n' is 1 or 2, R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group and a —CN group, R" is a hydrogen atom or a (C$_1$-C$_4$)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salt, for use as an agent for preventing, inhibiting or treating pathological or nonpathological conditions linked with premature aging.

According to a particular embodiment, the present invention further relates to compounds of formula (I')

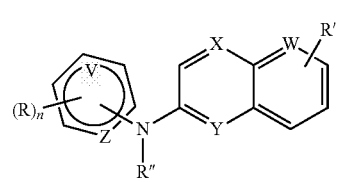

(I')

wherein:

means an aromatic ring wherein V is C or N and when V is N, V is in ortho, meta or para of Z, i.e. forms respectively a pyridazine, a pyrimidine or a pyrazine group, R independently represents a hydrogen atom, a halogen atom or a group chosen among a (C$_1$-C$_3$)alkyl group, a —CN group, a —COOH group, a (C$_1$-C$_3$)fluoroalkyl group, a (C$_1$-C$_3$)fluoroalkoxy group, a —NO$_2$ group, a —NR$_1$R$_2$ group and a (C$_1$-C$_3$)alkoxy group, R$_1$ and R$_2$ are independently a hydrogen atom or a (C$_1$-C$_3$)alkyl group, n is 1 or 2, R' is a hydrogen atom or a group chosen among a (C$_1$-C$_3$)alkyl group, a halogen atom, a hydroxy group, a —COOH group and a —CN group, R" is a hydrogen atom or a (C$_1$-C$_4$)alkyl group, Z is N or C, Y is N or C, X is N or C, W is N or C, and wherein at most two of the groups V, Z, Y, X and W are N, or anyone of its pharmaceutically acceptable salt, for use as an agent for preventing, inhibiting or treating pathological or nonpathological conditions linked with premature aging.

According to one aspect of this particular embodiment, the present invention relates to a compound of formula (I') as defined above, wherein V is N, for use as an agent for preventing, inhibiting or treating pathological or nonpathological conditions linked with premature aging.

According to one aspect of this particular embodiment, the present invention relates to a compound of formula (I') as defined above, wherein Z is N, V is C, Y is N, X is C and W is C, for use as an agent for preventing, inhibiting or treating pathological or nonpathological conditions linked with premature aging.

According to another aspect of this particular embodiment, the present invention relates to a compound of formula (I') as defined above, wherein Z is C, V is C, Y is N, X is C and W is C, for use as an agent for preventing, inhibiting or treating pathological or nonpathological conditions linked with premature aging.

According to another aspect of this particular embodiment, the present invention relates to a compound of formula (I') as defined above, wherein Z is N, V is C, Y is C, X is N and W is C, for use as an agent for preventing, inhibiting or treating pathological or nonpathological conditions linked with premature aging.

According to another aspect of this particular embodiment, the present invention relates to a compound of formula (I') as defined above, wherein Z is N, V is C, Y is C, X is C and W is N, for use as an agent for preventing, inhibiting or treating pathological or nonpathological conditions linked with premature aging.

According to one aspect, the present invention relates to a compound of formula (I) as defined above, wherein Z is N, V is C, Y is N, X is C and W is C, for use as an agent for preventing, inhibiting or treating pathological or nonpathological conditions linked with premature aging.

According to another aspect, the present invention relates to a compound of formula (I) as defined above, wherein Z is C, V is C, Y is N, X is C and W is C, for use as an agent for preventing, inhibiting or treating pathological or nonpathological conditions linked with premature aging.

According to another aspect, the present invention relates to a compound of formula (I) as defined above, wherein Z is N, V is C, Y is C, X is N and W is C, for use as an agent for preventing, inhibiting or treating pathological or nonpathological conditions linked with premature aging.

According to another aspect, the present invention relates to a compound of formula (I) as defined above, wherein Z is N, V is C, Y is C, X is C and W is N, for use as an agent for preventing, inhibiting or treating pathological or nonpathological conditions linked with premature aging.

In one particular variant, the present invention is directed to a compound of formula (I) wherein:
Z is N or C, Y is N or C, X is N or C and W is C,
n is equal to 1,
R is a hydrogen atom, a —COOH group, a ($C_1$-$C_3$)alkyl group or a ($C_1$-$C_3$)fluoroalkoxy group,
R' is a hydrogen atom,
R" is a hydrogen atom, and
wherein at most two of the groups Z, Y and X are N,
or anyone of its pharmaceutically acceptable salt,
for use as an agent for preventing, inhibiting or treating pathological or nonpathological conditions linked with premature aging.

Still in another particular variant, the compound of formula (I) may be defined as a compound of formula (IIa) as follows:

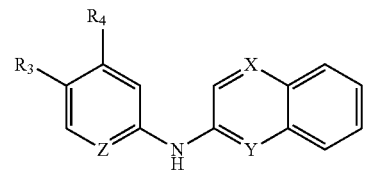

wherein:
Z is N or C, Y is N or C, X is N or C,
at least one of $R_3$ and $R_4$ is a hydrogen atom and the other is a —COOH group, a ($C_1$-$C_3$)alkyl group or a ($C_1$-$C_3$) fluoroalkoxy group, or anyone of its pharmaceutically acceptable salt.

Therefore, the present invention extends to a compound of formula (IIa) as defined above for use as an agent for preventing, inhibiting or treating pathological or nonpathological conditions linked with premature aging.

The present invention further relates to a compound of formula (IIb)

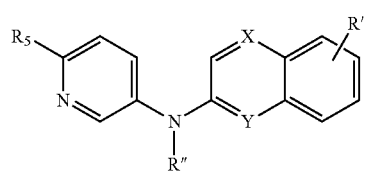

wherein:
Y is N or C,
X is N or C,
$R_5$ is a hydrogen atom, a halogen atom or a group chosen among a ($C_1$-$C_3$)alkyl group, a —CN group, a ($C_1$-$C_3$) alkoxy group, a —$NO_2$ group and a ($C_1$-$C_3$)fluoroalkyl group, and
R' and R" are as defined above,
or anyone of its pharmaceutically acceptable salt,
for use as an agent for preventing, inhibiting or treating pathological or nonpathological conditions linked with premature aging.

The present invention further relates to a compound of formula (IIc)

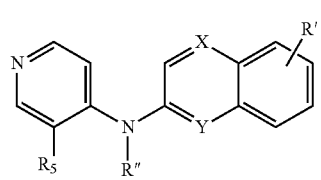

wherein:
Y is N or C,
X is N or C,
$R_5$ is a hydrogen atom, a halogen atom or a group chosen among a ($C_1$-$C_3$)alkyl group, a —CN group, a ($C_1$-$C_3$) alkoxy group, a —$NO_2$ group and a ($C_1$-$C_3$)fluoroalkyl group, and
R' and R" are as defined above,
or anyone of its pharmaceutically acceptable salt,
for use as an agent for preventing, inhibiting or treating pathological or nonpathological conditions linked with premature aging.

According to a first particular embodiment, an additional subject-matter of the present invention is a compound of formula (Ia-1)

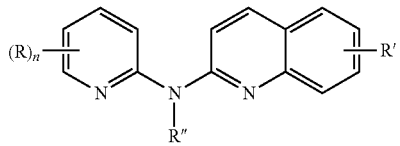

(Ia-1)

wherein:

R independently represent a hydrogen atom, a halogen atom, or a group chosen among a ($C_1$-$C_3$)alkyl group, a —CN group, a —COOH group, a ($C_1$-$C_3$)fluoroalkyl group, a ($C_1$-$C_3$)fluoroalkoxy group, a —NO$_2$ group and a ($C_1$-$C_3$) alkoxy group, R" is as defined above and is advantageously a hydrogen atom, n is 1 or 2, and advantageously 1, and R' is a hydrogen atom or a group chosen among a ($C_1$-$C_3$)alkyl group, a halogen atom, a hydroxy group, a —COOH group and a —CN group, or one of its pharmaceutically acceptable salt, for use as an agent for preventing, inhibiting or treating pathological or nonpathological conditions linked with premature aging.

The present invention further relates to a compound of formula (Ia-1) as defined above, as such, wherein:

R, R" and n are as defined above,

R' is a hydrogen atom or a group chosen among a ($C_1$-$C_3$)alkyl group, a halogen atom, a —COOH group and a —CN group, and wherein R and R' are not simultaneously a hydrogen atom or a methyl group and R is not a bromine atom, or one of its pharmaceutically acceptable salt.

Still according to this particular embodiment, the present invention more particularly focuses on compounds of formula (Ia'-1)

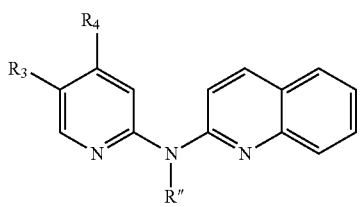

(Ia'-1)

wherein:

at least one of $R_3$ and $R_4$ is a hydrogen atom and the other is a hydrogen atom, a —COOH group or a ($C_1$-$C_3$)alkyl group, and R" is as defined above and is advantageously a hydrogen atom, or one of its pharmaceutically acceptable salt, for use as an agent for preventing, inhibiting or treating pathological or nonpathological conditions linked with premature aging.

According to a second particular embodiment, an additional subject-matter of the present invention is a compound of formula (Ib-1)

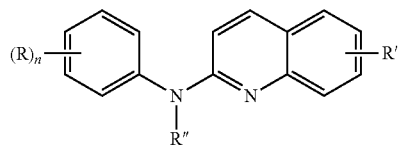

(Ib-1)

wherein:

R independently represent a hydrogen atom, a halogen atom, or a group chosen among a ($C_1$-$C_3$)alkyl group, a —CN group, a —COOH group, a ($C_1$-$C_3$)fluoroalkyl group, a ($C_1$-$C_3$)fluoroalkoxy group, a —NO$_2$ group, a —NR$_1$R$_2$ group and a ($C_1$-$C_3$)alkoxy group, $R_1$ and $R_2$ are independently a hydrogen atom or a ($C_1$-$C_3$)alkyl group, n is 1 or 2, and advantageously 1, R' is a hydrogen atom or a group chosen among a ($C_1$-$C_3$)alkyl group, a halogen atom, a hydroxy group, a —COOH group and a —CN group, and R" is as defined above and is advantageously a hydrogen atom, or one of its pharmaceutically acceptable salt, for use as an agent for preventing, inhibiting or treating pathological or nonpathological conditions linked with premature aging.

The present invention further relates to a compound of formula (Ib-1) as defined above, as such wherein:

R' and R" are as defined above, n is 1, and

R is a ($C_1$-$C_3$)fluoroalkoxy group, or one of its pharmaceutically acceptable salt.

Still according to this particular embodiment, the present invention more particularly focuses on compounds of formula (Ib'-1)

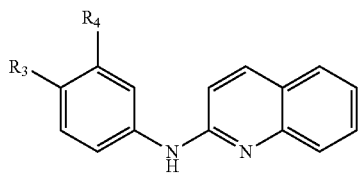

(Ib'-1)

wherein:

at least one of $R_3$ and $R_4$ is a hydrogen atom and the other is a ($C_1$-$C_3$)fluoroalkoxy group or a ($C_1$-$C_4$)alkoxy group, or one of its pharmaceutically acceptable salt, for use as an agent for preventing, inhibiting or treating pathological or nonpathological conditions linked with premature aging.

According to a third particular embodiment, an additional subject-matter of the present invention is a compound of formula (Ic-1)

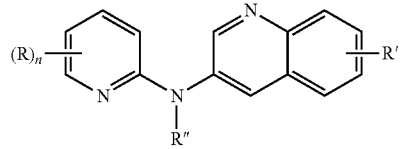

(Ic-1)

wherein:

R independently represent a hydrogen atom, a halogen atom, or a group chosen among a $(C_1\text{-}C_3)$alkyl group a —CN group, a —COOH group, a $(C_1\text{-}C_3)$fluoroalkyl group, a —NO$_2$ group and a $(C_1\text{-}C_3)$alkoxy group, n is 1 or 2, and advantageously 1, R' is a hydrogen atom or a $(C_1\text{-}C_3)$alkyl group, and in particular is a hydrogen atom, and R" is as defined above and is advantageously a hydrogen atom, or one of its pharmaceutically acceptable salt, for use as an agent for preventing, inhibiting or treating pathological or nonpathological conditions linked with premature aging.

The present invention further relates to a compound of formula (Ic-1) as defined above, as such wherein:

R, R' R" and n are as defined above, and wherein R and R' are not simultaneously a hydrogen atom, or one of its pharmaceutically acceptable salt.

Still according to this particular embodiment, the present invention more particularly focuses on compounds of formula (Ic'-1):

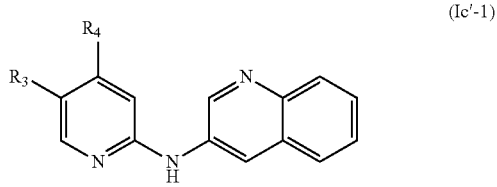

(Ic'-1)

wherein:

at least one of R$_3$ and R$_4$ is a hydrogen atom and the other is a $(C_1\text{-}C_3)$alkyl group, or one of its pharmaceutically acceptable salt, for use as an agent for preventing, inhibiting or treating pathological or nonpathological conditions linked with premature aging.

According to a fourth particular embodiment, an additional subject-matter of the present invention is a compound of formula (Id-1):

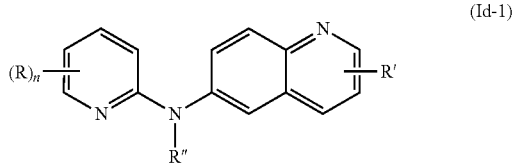

(Id-1)

wherein:

R independently represent a hydrogen atom, a halogen atom, or a group chosen among a $(C_1\text{-}C_3)$alkyl group, a —CN group, a —COOH group, a $(C_1\text{-}C_3)$fluoroalkyl group, a $(C_1\text{-}C_3)$fluoroalkoxy group and a —NO$_2$ group, n is 1 or 2, and advantageously 1, R' is a hydrogen atom or a $(C_1\text{-}C_3)$alkyl group, and in particular is a hydrogen atom, and R" is as defined above and is advantageously a hydrogen atom, or one of its pharmaceutically acceptable salt, for use as an agent for preventing, inhibiting or treating pathological or nonpathological conditions linked with premature aging.

The compound of formula (Id-1) as such and as defined above also form part of the present invention, with the proviso that when R' is a hydrogen atom, R is different from a —NO$_2$ group, or one of its pharmaceutically acceptable salt.

The compounds of formulae (I'), (IIa), (IIb), (IIc), (Ia-1), (Ib-1), (Ic-1) and (Id-1) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

According to one aspect, the present invention relates to a compound of formula (I) as defined above, wherein Z is N, V is C, Y is N, X is C, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is C, Y is N, X is C, T is C, U is C and W is C, for use as an agent for preventing, inhibiting or treating pathological or nonpathological conditions linked with premature aging.

According to another aspect, the present invention relates to a compound of formula (I) as defined above, wherein Z is N, V is C, Y is C, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is N, V is C, Y is C, X is C, T is C, U is C and W is N, for use as an agent for preventing, inhibiting or treating pathological or nonpathological conditions linked with premature aging.

According to another aspect, the present invention relates to a compound of formula (I) as defined above, wherein Z is N, V is N and is in para of Z, Y is N, X is C, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is N and is in para of Z, Y is C, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is N and is in meta of Z and is in para of the bond linked to NR", Y is N, X is C, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is N and is in meta of Z and is in para of the bond linked to NR", Y is C, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is C, Y is C, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is C, Y is N, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is N, V is N and is in meta of Z and in ortho of the bond linked to NR", Y is N, X is C, T is C, U is C and W is C, for use as an agent for preventing, inhibiting or treating pathological or nonpathological conditions linked with premature aging.

According to another aspect, the present invention relates to a compound of formula (I) as defined above, wherein Z is N, V is N and is in para of Z, Y is C, X is C, T is C, U is C and W is N, for use as an agent for preventing, inhibiting or treating pathological or nonpathological conditions linked with premature aging.

According to another aspect, the present invention relates to a compound of formula (I) as defined above, wherein Z is N, V is N and is in para of Z, Y is C, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is N, V is C, Y is N, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is N, V is N and is in meta of Z and is in ortho of the bond linked to NR", Y is N, X is N, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is C, Y is C, X is C, T is N, U is C and W is C, for use as an agent for preventing, inhibiting or treating pathological or nonpathological conditions linked with premature aging.

According to another aspect, the present invention relates to a compound of formula (I) as defined above, wherein Z is N, V is C, Y is C, X is C, T is N, U is C and W is C, for use as an agent for preventing, inhibiting or treating pathological or nonpathological conditions linked with premature aging.

According to another aspect, the present invention relates to a compound of formula (I) as defined above, wherein Z is N, V is C, Y is C, X is C, T is C, U is N and W is C, for use as an agent for preventing, inhibiting or treating pathological or nonpathological conditions linked with premature aging.

The compounds of the invention may exist in the form of free bases or of addition salts with pharmaceutically acceptable acids.

Suitable physiologically acceptable acid addition salts of compounds of formula (I) include hydrochloride, hydrobromide, tartrate, fumarate, citrate, trifluoroacetate, ascorbate, triflate, mesylate, tosylate, formate, acetate and malate.

The compounds of formula (I) and or salts thereof may form solvates (e.g. hydrates) and the invention includes all such solvates.

In the context of EMBODIMENT IIII of the present disclosure, the term:
"halogen" is understood to mean chlorine, fluorine, bromine, or iodine, and in particular denotes chlorine, fluorine or bromine,
"($C_1$-$C_3$)alkyl" as used herein respectively refers to $C_1$-$C_3$ normal, secondary or tertiary saturated hydrocarbon. Examples are, but are not limited to, methyl, ethyl, 1-propyl, 2-propyl,
"($C_1$-$C_3$)alkoxy" as used herein respectively refers to O—($C_1$-$C_3$)alkyl moiety, wherein alkyl is as defined above. Examples are, but are not limited to, methoxy, ethoxy, 1-propoxy, 2-propoxy,
"fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl, and
"patient" may extend to humans or mammals, such as cats or dogs.

According to one embodiment, the present invention relates to a compound of formula (I) as defined above for use as an agent for preventing, inhibiting or treating pathological or nonpathological conditions linked with premature aging, wherein T is C, and Z, V, Y, X, U and W are as defined above.

According to another embodiment, the present invention relates to a compound of formula (I) as defined above for use as an agent for preventing, inhibiting or treating pathological or nonpathological conditions linked with premature aging, wherein W is C, and Z, V, Y, X, U and T are as defined above.

According to another embodiment, the present invention relates to a compound of formula (I) as defined above for use as an agent for preventing, inhibiting or treating pathological or nonpathological conditions linked with premature aging, wherein Z is N, V is C, U is C, T is C and W, Y and X are as defined above.

According to one preferred aspect, the present invention relates to a compound of formula (I) as defined above, wherein Z is N, V is C, Y is N, X is C, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is C, V is C, Y is N, X is C, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is N, V is C, Y is C, X is N, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is N, V is C, Y is C, X is C, T is C, U is C and W is N, for use as an agent for preventing, inhibiting or treating pathological or nonpathological conditions linked with premature aging.

According to another preferred aspect, the present invention relates to a compound of formula (I) as defined above, wherein Z is N, V is N and is in para of Z, Y is N, X is C, T is C, U is C and W is C, for use as an agent for preventing, inhibiting or treating pathological or nonpathological conditions linked with premature aging.

According to another aspect, the present invention relates to a compound of formula (I) as defined above, wherein Z is C, V is C, Y is C, X is N, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is C, V is C, Y is N, X is N, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is N, V is N and is in meta of Z and is in ortho of the bond linked to NR", Y is N, X is C, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is N, V is C, Y is N, X is N, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is N, V is N and is in meta of Z and is in ortho of the bond linked to NR", Y is N, X is N, T is C, U is C and W is C, for use as an agent for preventing, inhibiting or treating pathological or nonpathological conditions linked with premature aging.

According to another preferred aspect, the present invention relates to a compound of formula (I) as defined above, wherein Z is N, V is C, Y is C, X is C, T is N, U is C and W is C, for use as an agent for preventing, inhibiting or treating pathological or nonpathological conditions linked with premature aging.

According to a particular embodiment, an additional subject-matter of the present invention is a compound of formula (Ia)

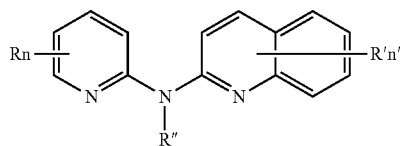

(Ia)

wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group, R" is as defined above and is advantageously a hydrogen atom, n is as defined above and is advantageously 1, n' is as defined above and is advantageously 1, R' is a hydrogen atom, a halogen atom or a group chosen among a $(C_1-C_3)$alkyl group, a —NO$_2$ group, a $(C_1-C_3)$alkoxy group and a —NR$_1$R$_2$ group, R$_1$ and R$_2$ are a hydrogen atom or a $(C_1-C_3)$alkyl group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ib)

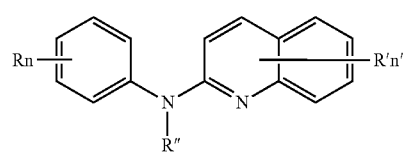

(Ib)

wherein:

R independently represent a hydrogen atom, a halogen atom or a group chosen among a $(C_1-C_3)$alkyl group, a —NR$_1$R$_2$ group, a $(C_1-C_3)$fluoroalkoxy group, a —NO$_2$ group, a phenoxy group and a $(C_1-C_4)$alkoxy group, R$_1$ and R$_2$ are independently a hydrogen atom or a $(C_1-C_3)$alkyl group, R" is as defined above and is advantageously a hydrogen atom, n is as defined above and is preferably 1 or 2, n' is as defined above and is preferably 1, R' is a hydrogen atom, a halogen atom or a group chosen among a $(C_1-C_3)$alkyl group and a $(C_1-C_4)$alkoxy group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ic)

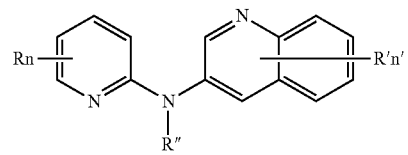

(Ic)

wherein:

R independently represent a hydrogen atom or a group chosen among a $(C_1-C_3)$alkyl group, a $(C_1-C_3)$fluoroalkyl group, a —NR$_1$R$_2$ group, a —COOR$_1$ group, a —NO$_2$ group and a $(C_1-C_3)$alkoxy group, R" is as defined above and is advantageously a hydrogen atom, n is as defined above and is advantageously 1, n' is as defined above and is advantageously 1, R' is a hydrogen atom, R$_1$ and R$_2$ are independently a hydrogen atom or a $(C_1-C_3)$alkyl group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Id)

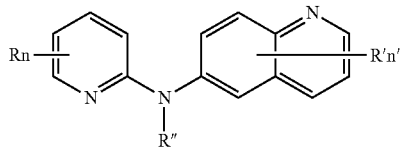

(Id)

wherein:

R independently represent a hydrogen atom or a group chosen among a (C₁-C₃)alkyl group, a (C₁-C₃)fluoroalkyl group and a (C₁-C₃)alkoxy group, R″ is as defined above and is advantageously a hydrogen atom, n is as defined above and is advantageously 1, n′ is as defined above and is advantageously 1, R′ is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ie)

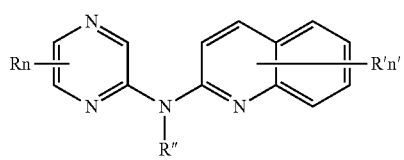

(Ie)

wherein:

R represents a hydrogen atom,

R″ is as defined above and is advantageously a hydrogen atom, n is as defined above and is advantageously 1, n′ is as defined above and is advantageously 1, R′ is a hydrogen atom, a halogen atom or a group chosen among a (C₁-C₃)alkyl group and a (C₁-C₃)alkoxy group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (If)

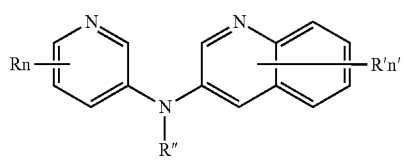

(If)

wherein:

R represents a hydrogen atom,

R″ is as defined above and is advantageously a hydrogen atom, n is as defined above and is advantageously 1, n′ is as defined above and is advantageously 1, R′ is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ig)

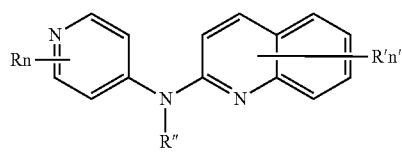

(Ig)

wherein:

R represents a hydrogen atom,

R″ is as defined above and is advantageously a hydrogen atom, n is as defined above and is advantageously 1, n′ is as defined above and is advantageously 1, R′ is a hydrogen atom or a halogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ih)

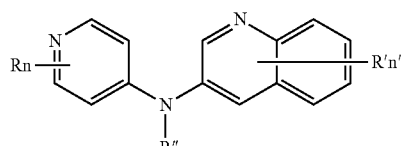

(Ih)

wherein:

R represents a hydrogen atom,

R″ is as defined above and is advantageously a hydrogen atom, n is as defined above and is advantageously 1, n′ is as defined above and is advantageously 1, R′ is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ii)

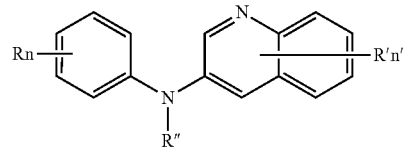

(Ii)

wherein:

R independently represent a hydrogen atom or a group chosen among a (C₁-C₃)fluoroalkoxy group and a (C₁-C₃) alkoxy group, R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ij)

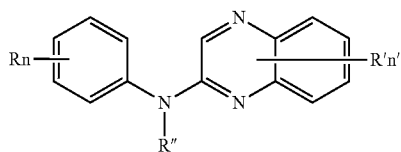

wherein:

R independently represent a hydrogen atom or a group chosen among a $(C_1-C_3)$fluoroalkoxy group and a $(C_1-C_3)$ alkyl group, R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ik)

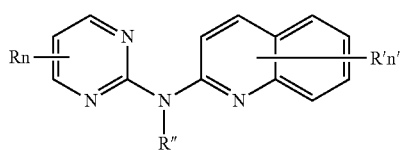

wherein:

R represents a hydrogen atom,

R" is as defined above and is advantageously a hydrogen atom, n is as defined above and is advantageously 1, n' is as defined above and is advantageously 1, R' is a hydrogen atom, a halogen atom or a $(C_1-C_3)$alkyl group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Il)

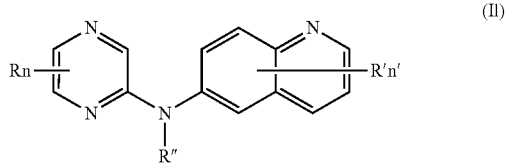

wherein:

R represents a hydrogen atom,

R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Im)

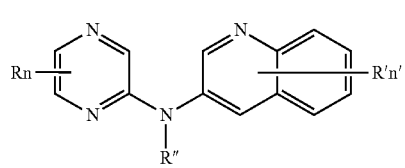

wherein:

R represents a hydrogen atom,

R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Io)

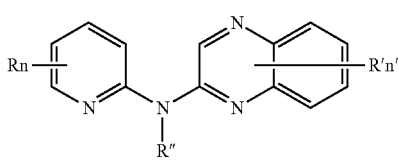

wherein:

R independently represent a hydrogen atom or a halogen atom or a group chosen among, a —NO$_2$ group, a —CN group and a $(C_1-C_3)$alkyl group, said alkyl being optionally mono-substituted by a hydroxyl group, R" is as defined above and is advantageously a hydrogen atom, n is as defined above and is advantageously 1, n' is as defined above and is advantageously 1, R' is a hydrogen atom, a halogen atom or a $(C_1-C_3)$ fluoroalkyl group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ip)

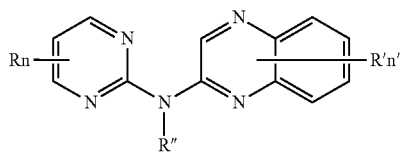

wherein:

R represents a hydrogen atom,

R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Iq)

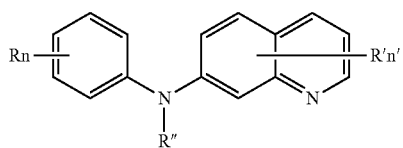

wherein:

R independently represent a hydrogen atom, a $(C_1-C_3)$ alkoxy group or a $(C_1-C_3)$fluoroalkoxy group, R" is as defined above and is advantageously a hydrogen atom, n is as defined above and is advantageously 1, n' is as defined above and is advantageously 1, R' is a hydrogen atom or a group chosen among a —$NR_1R_2$ group, a N-methylpiperazinyl group, a $(C_1-C_3)$ alkoxy group and a morpholino group, $R_1$ and $R_2$ are independently a hydrogen atom or a $(C_1-C_3)$alkyl group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Ir)

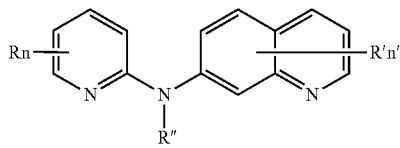

wherein:

R independently represent a hydrogen atom or a $(C_1-C_3)$ alkyl group,

R" is as defined above and is advantageously a hydrogen atom, n is as defined above and is advantageously 1, n' is as defined above and is advantageously 1, R' is a hydrogen atom or a group chosen among a —$NR_1R_2$ group, a morpholino group and a $(C_1-C_3)$alkoxy group, $R_1$ and $R_2$ are independently a hydrogen atom or a $(C_1-C_3)$alkyl group, or one of its pharmaceutically acceptable salt, for use as an agent for preventing, inhibiting or treating pathological or nonpathological conditions linked with premature aging.

According to another particular embodiment, an additional subject-matter of the present invention is a compound of formula (Iee)

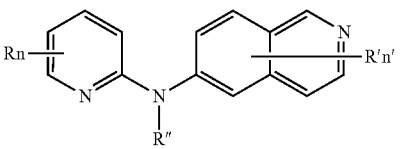

wherein:

R independently represent a hydrogen atom, a $(C_1-C_3)$ alkyl group or a $(C_1-C_3)$fluoroalkyl group, R" is as defined above and is advantageously a hydrogen atom, n is as defined above and is advantageously 1, n' is as defined above and is advantageously 2, R' is a hydrogen atom or a $(C_1-C_3)$alkyl group, or one of its pharmaceutically acceptable salt, for use as an agent for preventing, inhibiting or treating pathological or nonpathological conditions linked with premature aging.

Among the previous defined families of compounds of formulae (Ia) to (Iee), some are more particularly preferred for their use as an agent for preventing, inhibiting or treating pathological or nonpathological conditions linked with premature aging. These preferred compounds particularly belong to formulae (Ia), (Ib), (Ic), (Id), (Ie), (Ii), (Ij), (Ik), (Io), (Ip) and (Ir), as defined above or one of its pharmaceutically acceptable salts.

Accordingly the present invention further relates to a compound chosen among compounds of formulae (Ia), (Ib), (Ic), (Id), (Ie), (Ii), (Ij), (Ik), (Io), (Ip), (Ir) and their pharmaceutically acceptable salts for use as an agent for preventing, inhibiting or treating pathological or nonpathological conditions linked with premature aging.

Furthermore, among such compounds particularly preferred for their use as described above, some of them, i.e.

compounds of formulae (Ia), (Ib), (Ic), (Ie), (Ii), (Ij), (Ik), and (Io) are more particularly preferred for their use, as described below:

Thus, according to a more particular embodiment, the present invention particularly focuses on a compound of formula (Ia)

wherein:

R independently represent a hydrogen atom, a halogen atom or a group chosen among a $(C_1-C_3)$alkyl group, a —CN group, a —COOR$_1$ group, a $(C_1-C_3)$fluoroalkyl group, a —NO$_2$ group and a $(C_1-C_3)$alkoxy group, $R_1$ is a hydrogen atom or a $(C_1-C_3)$alkyl group, R" is as defined above and more preferably is a hydrogen atom, n is as defined above and more preferably is 1, n' is as defined above and more preferably is 1, R' is a hydrogen atom, a halogen atom or a $(C_1-C_3)$alkyl group, or one of its pharmaceutically acceptable salt, for use as an agent for preventing, inhibiting or treating pathological or nonpathological conditions linked with premature aging.

Still according to this more particular embodiment, the present invention more preferably focuses on compounds of formula (Ia'),

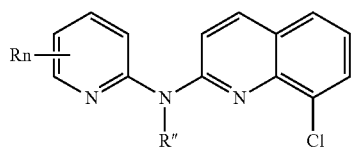

(Ia')

wherein,

R independently represent a hydrogen atom, a —COOR$_1$ group or a $(C_1-C_3)$ alkyl group, $R_1$ is as defined above, R" is a hydrogen atom, n is 1 or 2, or one of its pharmaceutically acceptable salt, for use as an agent for preventing, inhibiting or treating pathological or nonpathological conditions linked with premature aging.

According to another more particular embodiment, the present invention particularly focuses on a compound of formula (Ib)

wherein:

R independently represent a hydrogen atom, a halogen atom or a group chosen among a $(C_1-C_3)$alkyl group, a $(C_1-C_3)$fluoroalkoxy group and a phenoxy group, $R_1$ is a hydrogen atom or a $(C_1-C_3)$alkyl group, R" is as defined above and more preferably is a hydrogen atom, n is as defined above and more preferably is 1, n' is as defined above, R' is a hydrogen atom, or one of its pharmaceutically acceptable salt, for use as an agent for preventing, inhibiting or treating pathological or nonpathological conditions linked with premature aging.

According to another more particular embodiment, the present invention particularly focuses on a compound of formula (Ic)

wherein:

R independently represent a hydrogen atom or a group chosen among a $(C_1-C_3)$alkyl group, a —NO$_2$ group and a $(C_1-C_3)$alkoxy group, R" is as defined above and more preferably is a hydrogen atom, n is as defined above and more preferably is 1, n' is as defined above, R' is a hydrogen atom, or one of its pharmaceutically acceptable salt, for use as an agent for preventing, inhibiting or treating pathological or nonpathological conditions linked with premature aging.

According to another more particular embodiment, the present invention particularly focuses on a compound of formula (Ie)

wherein:

R represents a hydrogen atom,

R" is as defined above and more preferably is a hydrogen atom, n is as defined above and more preferably is 1, n' is as defined above, R' is a hydrogen atom or a halogen atom, or one of its pharmaceutically acceptable salt, for use as an agent for preventing, inhibiting or treating pathological or nonpathological conditions linked with premature aging.

According to another more particular embodiment, the present invention particularly focuses on a compound of formula (Ii)

wherein:

R independently represent a hydrogen atom or a $(C_1-C_3)$ alkoxy group,

R" is as defined above and is advantageously a hydrogen atom, n is as defined above and is advantageously 1, n' is as defined above, R' is a hydrogen atom, or one of its pharmaceutically acceptable salt, for use as an agent for preventing, inhibiting or treating pathological or nonpathological conditions linked with premature aging.

According to another more particular embodiment, the present invention particularly focuses on a compound of formula (Ij)

wherein:

R independently represent a hydrogen atom or a group chosen among a $(C_1-C_3)$fluoroalkoxy group and a $(C_1-C_3)$ alkyl group, R" is as defined above and more preferably is a hydrogen atom, n is as defined above and more preferably is 2, n' is as defined above, R' is a hydrogen atom, or one of its pharmaceutically acceptable salt, for use as an agent for preventing, inhibiting or treating pathological or nonpathological conditions linked with premature aging.

According to another more particular embodiment, the present invention particularly focuses on a compound of formula (Ik)

wherein:

R represents a hydrogen atom,

R" is as defined above and more preferably is a hydrogen atom, n is as defined above and more preferably is 1, n' is as defined above, R' is a hydrogen atom,
or one of its pharmaceutically acceptable salt,
for use as an agent for preventing, inhibiting or treating pathological or nonpathological conditions linked with premature aging.

According to another more particular embodiment, the present invention particularly focuses on a compound of formula (Io)
wherein:
R independently represent a hydrogen atom or a group chosen among a $(C_1-C_3)$alkyl group and a —CN group,
R" is as defined above and more preferably is a hydrogen atom,
n is as defined above and more preferably is 1,
n' is as defined above,
R' is a hydrogen atom,
or one of its pharmaceutically acceptable salt,
for use as an agent for preventing, inhibiting or treating pathological or nonpathological conditions linked with premature aging.

In a particular embodiment, the present invention relates to a compound of formula (Ib), (Ie) or (Ij) as defined above or one of its pharmaceutically acceptable salts, for use as an agent for preventing, inhibiting or treating pathological or nonpathological conditions linked with premature aging.

According to a preferred embodiment of the present invention, the compound for use as an agent for preventing, inhibiting or treating pathological or nonpathological conditions linked with premature aging, is chosen from:
(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine,
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N, 1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N, 1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine

(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine
(112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)quinolin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N, 1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine and their pharmaceutically acceptable salts.

Among said compounds, compounds (2), (3), (4), (5), (7), (8), (9), (10), (13), (15), (16), (17), (18), (25), (26), (28), (31), (32), (33), (34), (35), (36), (38), (39), (41), (42), (45), (59), (61), (82), (83), (86), (102), (105), (106), (107), (108), (109), (113), (120), (123), (125), (128), (135), (136), (137), (138), (142), (145), (146) and (147) are of particular interest.

The present invention therefore extends to compounds (2), (3), (4), (5), (7), (8), (9), (10), (13), (15), (16), (17), (18), (25), (26), (28), (31), (32), (33), (34), (35), (36), (38), (39), (41), (42), (45), (59), (61), (82), (83), (86), (102), (105), (106), (107), (108), (109), (113), (120), (123), (125), (128), (135), (136), (137), (138), (142), (145), (146) and (147) or one of its pharmaceutically acceptable salts for use as an agent for preventing, inhibiting or treating pathological or nonpathological conditions linked with premature aging.

Some of said preceding compounds are new and form part of the present invention: (2), (5), (7), (8), (10), (13), (15), (16), (18), (25), (26), (28), (31), (32), (33), (34), (35), (36), (38), (39), (41), (42), (59), (61), (82), (83), (86), (102), (105), (106), (107), (108), (109), (113), (125), (128), (135), (136), (137), (138), (142), (145), (146) and (147) or one of its pharmaceutically acceptable salts such as hydrochloride, hydrobromide, tartrate, fumarate, citrate, trifluoroacetate, ascorbate, triflate, mesylate, tosylate, formate, acetate and malate.

The compounds of formulae (I), (Ia), (Ib), (Ic), (Id), (Ie), (If), (Ig), (Ih), (Ii), (Ij), (Ik), (Il), (Im), (Io), (Ip), (Iq), (Ir) and (Iee) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

Among the compounds of formula (I), some of them are new and form part of the invention, as well as their pharmaceutically acceptable salts, such as hydrochloride, hydrobromide, tartrate, fumarate, citrate, trifluoroacetate, ascorbate, triflate, mesylate, tosylate, formate, acetate and malate.

According to a particular embodiment, the present invention encompasses compounds of formula (Ig)
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group,
n is 1 or 2,
n' is 1 or 2,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group,
R" is a hydrogen atom or a $(C_1-C_4)$alkyl group,
R$_1$ and R$_2$ are independently a hydrogen atom or a $(C_1-C_3)$alkyl group,
with the proviso that R and R' are not simultaneously a hydrogen atom,
and when n and n' are 1 and R is a hydrogen atom then R' is not a —COOH group,
or anyone of its pharmaceutically acceptable salt.

According to another particular embodiment, the present invention encompasses compounds of formula (If)
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group,
n is 1 or 2,
n' is 1 or 2,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group,
R" is a hydrogen atom or a $(C_1-C_4)$alkyl group,
R$_1$ and R$_2$ are independently a hydrogen atom or a $(C_1-C_3)$alkyl group, or anyone of its pharmaceutically acceptable salt.

According to another particular embodiment, the present invention encompasses compounds of formula (Ih)
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group,
n is 1 or 2,
n' is 1 or 2,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group,
R" is a hydrogen atom or a $(C_1-C_4)$alkyl group,
R$_1$ and R$_2$ are independently a hydrogen atom or a $(C_1-C_3)$alkyl group, or anyone of its pharmaceutically acceptable salt.

According to another particular embodiment, the present invention encompasses compounds of formula (Il)
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group,
n is 1 or 2,
n' is 1 or 2,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group,
R" is a hydrogen atom or a $(C_1-C_4)$alkyl group,
R$_1$ and R$_2$ are independently a hydrogen atom or a $(C_1-C_3)$alkyl group,
with the proviso that R and R' are not simultaneously a hydrogen atom,
or anyone of its pharmaceutically acceptable salt.

According to another particular embodiment, the present invention encompasses compounds of formula (Im)
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group,
n is 1 or 2,
n' is 1 or 2,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group,
R" is a hydrogen atom or a $(C_1-C_4)$alkyl group,
R$_1$ and R$_2$ are independently a hydrogen atom or a $(C_1-C_3)$alkyl group,
with the proviso that when n and n' are 1 and R is a hydrogen atom, R' is not a chlorine atom,
or anyone of its pharmaceutically acceptable salt.

For a sake of simplification, the following compounds and their corresponding definitions are called "new compounds".

According to another particular embodiment, the present invention encompasses compounds of formula (Ia), as such,

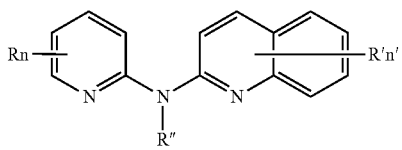

(Ia)

wherein:
R″ and n are as defined in formula (Ia),
n′ is 1,
R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a —NO$_2$ group, a ($C_1$-$C_3$)fluoroalkoxy group and a ($C_1$-$C_3$)alkoxy group,
R′ is a hydrogen atom or a halogen atom or a group chosen among a ($C_1$-$C_3$)alkyl group, a —COOR$_1$ group, and a —CN group,
R$_1$ is a hydrogen atom or a ($C_1$-$C_3$)alkyl group:
with the proviso that
when R and R′ are not simultaneously a hydrogen atom,
when n is 1, R is not a methyl group in ortho or para position with respect to Z, Z being N,
when R′ is a hydrogen atom, R is not a bromine atom or a chlorine atom,
when R is a hydrogen atom, R′ is not a methyl or ethyl group, a —COOH group, a COOC$_2$H$_5$ group or a bromine atom, said bromine atom being in ortho position of the bond linked to NR″,
or one of its pharmaceutically acceptable salt.

Still according to this particular embodiment, the present invention more particularly focuses on compounds of formula (Ia), as such, wherein:
R independently represent a hydrogen atom, a —NO$_2$ group, a ($C_1$-$C_3$)fluoroalkyl group, a ($C_1$-$C_3$)alkoxy group, a —CN group, a ($C_1$-$C_3$) alkyl group, a —COOR$_1$ group or a halogen atom,
R″ is as defined in formula (Ia),
R$_1$ is as defined above,
R′ is a hydrogen atom, a halogen atom or a ($C_1$-$C_3$) alkyl group,
n′ is 1,
n is 1 or 2,
with the proviso that
when n is 1, R is not a methyl group in ortho or para position with respect to Z, Z being N,
R is not a bromine atom or a chlorine atom when R′ is a hydrogen atom,
or one of its pharmaceutically acceptable salt.

Still according to this particular embodiment, the present invention more preferably focuses on compounds of formula (Ia′), as such,

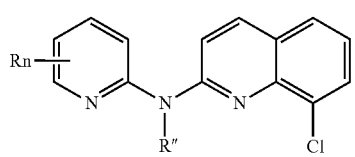

(Ia′)

wherein:
R independently represent a hydrogen atom, a —COOR$_1$ group, a ($C_1$-$C_3$) alkyl group, —NO$_2$ group, a ($C_1$-$C_3$) fluoroalkyl group, a —CN group, a halogen atom or a hydroxyl group,
R$_1$ is as defined above,
R″ is as defined in formula (Ia),
n is 1 or 2,
or one of its pharmaceutically acceptable salt.

According to another particular embodiment, the present invention encompasses compounds of formula (Ib), as such,

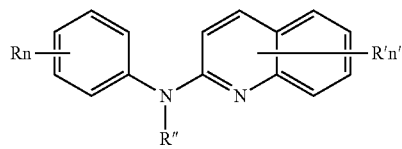

(Ib)

wherein:
R′ and R″ are as defined in formula (Ib),
n is 1, and
R is a hydrogen atom or a ($C_1$-$C_3$)fluoroalkoxy group,
or one of its pharmaceutically acceptable salt.

According to another particular embodiment, the present invention encompasses compounds of formula (Ic), as such,

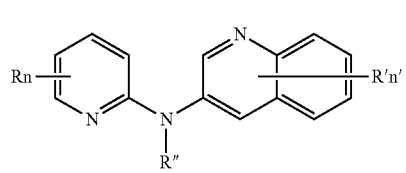

(Ic)

wherein:
R independently represent a hydrogen atom, a halogen atom or a group chosen among a ($C_1$-$C_3$)alkyl group, a ($C_1$-$C_3$)fluoroalkyl group, a —CN group, a hydroxyl group, a —COOR$_1$ group, a —NO$_2$ group, a —NR$_1$R$_2$ group and a ($C_1$-$C_3$)alkoxy group,
R$_1$ and R$_2$ are independently a hydrogen atom or a ($C_1$-$C_3$)alkyl group,
n is 1 or 2, and advantageously 1,
n′ is 1 or 2,
R″ is as defined in formula (Ic),
R′ is a hydrogen atom or a group chosen among a ($C_1$-$C_3$)alkyl group, a —NO$_2$ group, a —NR$_1$R$_2$ group and a ($C_1$-$C_3$)alkoxy group, with the proviso that
R and R′ are not simultaneously a hydrogen atom,
R is not a bromine atom when R′ is a hydrogen atom,
or one of its pharmaceutically acceptable salt.

Still according to this particular embodiment, the present invention more particularly focuses on compounds of formula (Ic), as such,
wherein:
R is a hydrogen atom, a ($C_1$-$C_3$)fluoroalkyl group, a ($C_1$-$C_3$)alkyl group, a ($C_1$-$C_3$)alkoxy group, a —NO$_2$ group or a —COOR$_1$ group,
n, R″, n′ and R$_1$ are as defined in formula (Ic),
R′ is a hydrogen atom or a group chosen among a ($C_1$-$C_3$)alkyl group, a —NO$_2$ group, a —NR$_1$R$_2$ group and a ($C_1$-$C_3$)alkoxy group, and is preferably a hydrogen atom,
or one of its pharmaceutically acceptable salt.

According to another particular embodiment, the present invention encompasses compounds of formula (Id), as such,

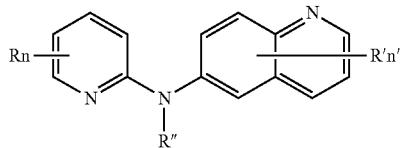
(Id)

wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group and a —NR$_1$R$_2$ group, R$_1$ and R$_2$ are independently a hydrogen atom or a $(C_1-C_3)$alkyl group, n is 1 or 2, and advantageously 1, n' is 1 or 2, R" is as defined in formula (I) and is advantageously a hydrogen atom, R' is a hydrogen atom or a group chosen among a $(C_1-C_3)$alkyl group, a —NO$_2$ group, a —NR$_1$R$_2$ group and a $(C_1-C_3)$alkoxy group, with the proviso that when R' is a hydrogen atom, R is different from a —NO$_2$ group, a —NH$_2$ group or a —COOH group, or one of its pharmaceutically acceptable salt.

Still according to this particular embodiment, the present invention more particularly focuses on compounds of formula (Id), as such, wherein, R is a hydrogen atom, a $(C_1-C_3)$alkyl group, a $(C_1-C_3)$ alkoxy group or a $(C_1-C_3)$fluoroalkyl group, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, and advantageously a hydrogen atom, R" is as defined in formula (I) and is advantageously a hydrogen atom, n is 1 or 2, and advantageously 1, n' is 1 or 2, or one of its pharmaceutically acceptable salt.

According to another particular embodiment, the present invention encompasses compounds of formula (Ie)

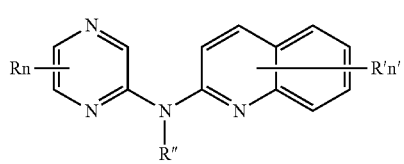
(Ie)

wherein:
R, R', R" n and n' are as defined in formula (I),
with the proviso that
when R is a hydrogen atom, R' is not a bromine atom,
or one of its pharmaceutically acceptable salt.

According to another particular embodiment, the present invention encompasses compounds of formula (Ii'), as such,

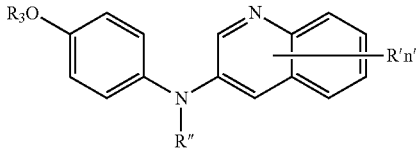
(Ii')

wherein:
R$_3$ is a $(C_1-C_3)$fluoroalkyl group or a $(C_1-C_3)$alkyl group,

R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R$_1$ and R$_2$ are independently a hydrogen atom or a $(C_1-C_3)$alkyl group, R" is as defined above and is advantageously a hydrogen atom, n' is as defined above and is advantageously 1, with the proviso that when R' is a hydrogen atom, R$_3$ is not a methyl group or a trifluoromethyl group or one of its pharmaceutically acceptable salt.

According to another particular embodiment, the present invention encompasses compounds of formula (Ij'), as such,

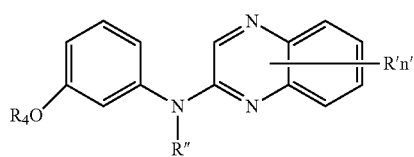
(Ij')

wherein:
R$_4$ is a $(C_1-C_3)$fluoroalkyl group or a $(C_1-C_3)$alkyl group,

R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R$_1$ and R$_2$ are independently a hydrogen atom or a $(C_1-C_3)$alkyl group, R" is as defined above and is advantageously a hydrogen atom, n' is as defined above and is advantageously 1, with the proviso that when R' is a hydrogen atom, R$_4$ is not a methyl group
or one of its pharmaceutically acceptable salt.

According to another particular embodiment, the present invention encompasses compounds of formula (Ij"), as such,

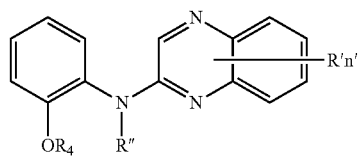
(Ij")

wherein:
R$_4$ is a $(C_1-C_3)$fluoroalkyl group or a $(C_1-C_3)$alkyl group,

R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a (C$_1$-C$_3$)alkoxy group and a —CN group, R$_1$ and R$_2$ are independently a hydrogen atom or a (C$_1$-C$_3$)alkyl group, R" is as defined above and is advantageously a hydrogen atom, n' is as defined above and is advantageously 1, or one of its pharmaceutically acceptable salt.

According to another particular embodiment, the present invention encompasses compounds of formula (Ij'"), as such,

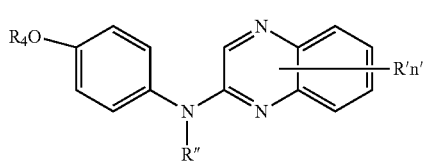

wherein:

R$_4$ is a (C$_1$-C$_3$)fluoroalkyl group or a (C$_1$-C$_3$)alkyl group,

R' is a hydrogen atom or a group chosen among a (C$_1$-C$_3$)alkyl group, a halogen atom, a hydroxyl group, a —NO$_2$ group, a —NR$_1$R$_2$ group, a (C$_1$-C$_3$)alkoxy group and a —CN group, R$_1$ and R$_2$ are independently a hydrogen atom or a (C$_1$-C$_3$)alkyl group, R" is as defined above and is advantageously a hydrogen atom, n' is as defined above and is advantageously 1, with the proviso that when R' is a chlorine atom or a hydrogen atom, R$_4$ is not an ethyl group or a methyl group, when R' is a methyl group or a tertio-butyl group, R$_4$ is not a methyl group, or one of its pharmaceutically acceptable salt.

According to another particular embodiment, the present invention encompasses compounds of formula (Ik), as such,

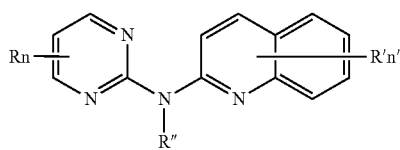

wherein:

R independently represent a hydrogen atom, a halogen atom or a group chosen among a (C$_1$-C$_3$)alkyl group, a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group and a (C$_1$-C$_3$)alkoxy, R$_1$ and R$_2$ are independently a hydrogen atom or a (C$_1$-C$_3$)alkyl group, n is 1 or 2, and is advantageously 1, n' is 1 or 2, R" is as defined in formula (Ik), R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a (C$_1$-C$_3$)alkoxy group and a —CN group, or one of its pharmaceutically acceptable salt.

Still according to this particular embodiment, the present invention more particularly focuses on compounds of formula (Ik), as such, wherein:

R is a hydrogen atom,

R" is as defined in formula (Ik),

R' is a hydrogen atom, a halogen atom or a (C$_1$-C$_3$) alkyl group, n is 1 or 2, and is advantageously 1, n' is 1 or 2, or one of its pharmaceutically acceptable salt.

According to another particular embodiment, the present invention encompasses compounds of formula (Io), as such,

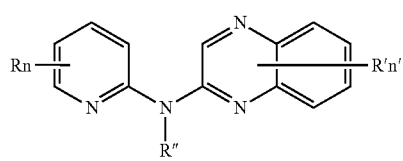

wherein:

R independently represent a hydrogen atom, a halogen atom or a group chosen among a (C$_1$-C$_3$)alkyl group, a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group and a (C$_1$-C$_3$)alkoxy group, R$_1$ and R$_2$ are independently a hydrogen atom or a (C$_1$-C$_3$)alkyl group, n is 1, 2 or 3, n' is 1 or 2, R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a (C$_1$-C$_3$)alkoxy group and a —CN group, R" is a hydrogen atom or a (C$_1$-C$_4$)alkyl group, with the proviso that when R is a hydrogen atom and n' is 1, R' is not a hydroxyl group, or one of its pharmaceutically acceptable salt.

Still according to this particular embodiment, the present invention more particularly focuses on compounds of formula (Io), as such, wherein:

R is a hydrogen atom, a (C$_1$-C$_3$)alkyl group or a —CN group, n is 1, 2 or 3, n' is 1 or 2, R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a (C$_1$-C$_3$)alkoxy group and a —CN group, and preferably is a hydrogen atom or a (C$_1$-C$_3$)alkyl group, R$_1$ is as defined in formula (Io), R" is a hydrogen atom or a (C$_1$-C$_4$)alkyl group, or one of its pharmaceutically acceptable salt.

According to another particular embodiment, the present invention encompasses compounds of formula (Ip), as such,

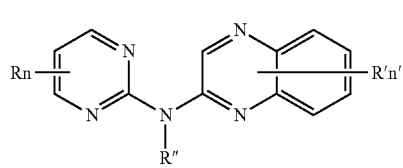

wherein:

R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group and a ($C_1$-$C_3$)alkoxy group, R$_1$ and R$_2$ are independently a hydrogen atom or a ($C_1$-$C_3$)alkyl group, n is 1 or 2, and advantageously 1, n' is 1 or 2, R' is a hydrogen atom or a group chosen among a ($C_1$-$C_3$)alkyl group, a halogen atom, a hydroxyl group, a —COOR$_1$ group, a —NO$_2$ group, a —NR$_1$R$_2$ group, a ($C_1$-$C_3$)alkoxy group and a —CN group, R" is a hydrogen atom or a ($C_1$-$C_4$)alkyl group, with the proviso that R and R' are not simultaneously a hydrogen atom, when n and n' are 2 then R and R' are not simultaneously a methyl group.

or one of its pharmaceutically acceptable salt.

According to another particular embodiment, the present invention encompasses compounds of formula (Ir), as such,

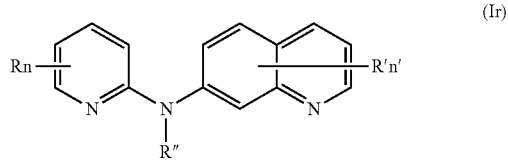

wherein:

R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group and a ($C_1$-$C_3$)alkoxy group, R$_1$ and R$_2$ are independently a hydrogen atom or a ($C_1$-$C_3$)alkyl group, n is 1 or 2, and advantageously 1, n' is 1 or 2, R' is a hydrogen atom or a group chosen among a ($C_1$-$C_3$)alkyl group, a halogen atom, a hydroxyl group, a —COOR$_1$ group, a —NO$_2$ group, a —NR$_1$R$_2$ group, a ($C_1$-$C_3$)alkoxy group and a —CN group, R" is a hydrogen atom or a ($C_1$-$C_4$)alkyl group, or one of its pharmaceutically acceptable salt.

Still according to this particular embodiment, the present invention more particularly focuses on compounds of formula (Ir), as such, wherein:

R is a hydrogen atom or a ($C_1$-$C_3$)alkyl group,

R' is a ($C_1$-$C_3$)alkoxy group or a —NR$_1$R$_2$ group,

R" is a hydrogen atom or a ($C_1$-$C_4$)alkyl group, n and n' are 1,

R$_1$ and R$_2$ are independently a hydrogen atom or a ($C_1$-$C_3$)alkyl group, or one of its pharmaceutically acceptable salt.

Among said compounds as such, compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts are of particular interest.

The present invention therefore extends to compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts, as such.

More preferably, compounds (1), (2), (5)-(7), (10)-(16), (18), (21)-(44), (46)-(74), (105)-(108), (124)-(130), (135)-(141), (145)-(147), (150)-(154), (159), (160)-(165), (168) and their pharmaceutically acceptable salts are of particular interest.

The present invention therefore extends more preferably to compounds (1), (2), (5)-(7), (10)-(16), (18), (21)-(44), (46)-(74), (105)-(108), (124)-(130), (135)-(141), (145)-(147), (150)-(154), (159), (160)-(165), (168) and their pharmaceutically acceptable salts, such as hydrochloride, hydrobromide, tartrate, fumarate, citrate, trifluoroacetate, ascorbate, triflate, mesylate, tosylate, formate, acetate and malate.

Still more preferably, the present invention extends to compounds (2), (5), (7), (10), (13), (15), (16), (18), (25), (26), (28), (31)-(36), (38), (39), (41), (42), (59), (61), (105)-(108), (125), (128), (135)-(138), (145)-(147) and their pharmaceutically acceptable salts, such as hydrochloride, hydrobromide, tartrate, fumarate, citrate, trifluoroacetate, ascorbate, triflate, mesylate, tosylate, formate, acetate and malate.

The new compounds of the present invention, i.e. compounds of formula (Ia), (Ib), (Ic), (Id), (Ie), (Ik), (Ii'), (Ij'), (Ij"), (Ij'"), (Io), (Ip) and (Ir) and the specific compounds as listed above, are not only useful as agent for inhibiting, preventing or treating premature aging but can also be used as agent for inhibiting, preventing or treating AIDS or cancer, and more particularly colorectal cancer, pancreatic cancer, lung cancer including non-small cell lung cancer, breast cancer, bladder cancer, gall bladder cancer, liver cancer, thyroid cancer, melanoma, uterine/cervical cancer, oesophageal cancer, kidney cancer, ovarian cancer, prostate cancer, head and neck cancer and stomach cancer, etc.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 (above, see EMBODIMENT I). The chemical structures and spectroscopic data of some compounds of formula (I) of the invention are illustrated respectively in the following Table I (above) and Table II (above, see EMBODIMENT I).

The following examples illustrate in detail the preparation of compounds (2), (3), (4), (7), (8), (26), (31), (82), (105), (113), (128), (135), (136), (137), (138), (142), (146), (13), (108), (16), (123), and (38) according to the invention. The structures of the products obtained have been confirmed by NMR spectra.

Embodiment III: Examples

Typical Procedure for Pd-Catalysed Aminations

To a solution of 2-chloro quinoline (82 mg, 0.5 mmol, 1 equiv) in tert-butanol (2 mL) were added the amino pyridine derivative/aniline (0.55 mmol, 1.1 equiv), Cs$_2$CO$_3$ (456 mg, 1.4 mmol, 2.8 equiv), Xantphos (5.8 mg, 0.01 mmol, 2 mol %), Pd(OAc)$_2$ (2.2 mg, 0.01 mmol, 2 mol %). The reaction mixture was heated at 90° C. and stirred for 20 hours under argon. The reaction mixture was concentrated under reduced pressure. The residue was purified by column chromatography on silica gel to yield compounds (2), (3), (4) and (8).

Example 1

2-(Quinolin-2-ylamino)-isonicotinic acid—(2) of table I $^1$H NMR (300 MHz, DMSO) δ 13.16 (s, 1H), 8.72 (d, J=5.2, 1H), 8.63 (d, J=9.0, 1H), 8.28-8.13 (m, 2H), 8.05 (d, J=8.0, 1H), 7.90 (t, J=7.5, 1H), 7.74-7.67 (m, 2H), 7.67-7.59 (m, 2H).

MS (electrospray) m/z (%) 266.1 (100) [M+H]$^+$.

Example 2

(4-Methyl-pyridin-2-yl)-quinolin-2-yl-amine—(3) of table I $^1$H NMR (300 MHz, CDCl$_3$) δ 8.92 (s, 1H), 8.21 (d, J=5.3, 2H), 7.95 (d, J=8.9, 1H), 7.89 (d, J=8.4, 1H), 7.67 (d, J=8.0, 1H), 7.62 (t, J=7.7, 1H), 7.40-7.28 (m, 2H), 6.78 (d, J=5.1, 1H), 2.41 (s, 3H).

$^{13}$C NMR (75 MHz, CDCl$_3$) δ 154.3, 153.3, 149.5, 147.3, 137.7, 129.8, 127.6, 127.1, 124.6, 123.7, 118.7, 114.1, 113.4, 21.7.

MS (electrospray) m/z (%) 236.2 (100) [M+H]$^+$.

Example 3

Pyridin-2-yl-quinolin-2-yl-amine—(4) of table I $^1$H NMR (300 MHz, CDCl$_3$) δ 8.38 (d, J=8.4, 1H), 8.31 (dd, J=1.0, 4.9, 1H), 8.01 (d, J=8.9, 1H), 7.87 (d, J=8.4, 1H), 7.77-7.68 (m, 3H), 7.64 (t, J=7.7, 1H), 7.36 (t, J=7.5, 1H), 7.31 (d, J=8.9, 1H), 6.94 (dd, J=5.0, 7.2, 1H).

$^{13}$C NMR (75 MHz, CDCl$_3$) δ 154.1, 153.1, 147.8, 147.3, 138.3, 137.8, 129.9, 127.6, 127.2, 124.6, 123.8, 117.4, 114.0, 113.0.

MS (electrospray) m/z (%) 222.2 (100) [M+H]$^+$.

Example 4

Quinolin-2-yl-(4-trifluoromethoxy-phenyl)-amine—(8) of table I $^1$H NMR (300 MHz, CDCl$_3$) δ 7.97 (d, J=8.8, 1H), 7.82 (d, J=8.4, 1H), 7.69 (t, J=9.4, 3H), 7.62 (t, J=7.7, 1H), 7.34 (t, J=7.5, 1H), 7.23 (d, J=8.7, 2H), 6.92 (d, J=8.9, 1H), 6.74 (s, 1H).

$^{13}$C NMR (75 MHz, CDCl$_3$) δ 153.9, 147.6, 144.4, 139.3, 138.1, 130.1, 127.7, 127.1, 124.4, 123.7, 122.5, 122.2, 121.0, 119.1, 112.2.

MS (electrospray) m/z (%) 305.0 (100) [M+H]$^+$.

According to route (A), the compound of formula (III) is placed in a protic solvent such as tert-butanol. The compound of formula (IV) is then added in a 1.1 molar ratio with respect to the compound of formula (III) in presence of an inorganic base, such as Cs$_2$CO$_3$ or K$_2$CO$_3$, in a 2.8 molar ratio, in the presence of a diphosphine, such as Xantphos (4,5-Bis(diphenylphosphino)-9,9-dimethylxanthene), or X-Phos 2-Dicyclohexylphosphino-2',4',6'-triisopropylbiphenyl in a 2 mol % amount relative to the total amount of compound of formula (III), and in the presence of a catalyst, such as Pd(OAc)$_2$, or Pd$_2$dba$_3$ in a 2 mol % amount relative to the total amount of compound of formula (III). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compounds (7), (26), (31), (8), (82), (105), (113), (128), (135), (136), (137), (138), (142), (146).

According to route (B), the compound of formula (V) is placed in a protic solvent such as tert-butanol. The compound of formula (VI) is then added in a 1.1 molar ratio with respect to the compound of formula (V) in presence of Cs$_2$CO$_3$ in a 2.8 molar ratio, in the presence of Xantphos (4,5-Bis(diphenylphosphino)-9,9-dimethylxanthene) in a 2 mol % amount relative to the total amount of compound of formula (V), and in the presence of a Pd(OAc)$_2$, in a 2 mol % amount relative to the total amount of compound of formula (V). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compound (13), (108), (16), (123), (38).

Example 5: Compound (7) of Table I

According to route (A), a mixture of 2-chloroquinoline (1.3 g), 2-amino-5-cyanopyridine (1.1 g), Pd(OAc)$_2$ (36.5 mg), XantPhos (94 mg) and Cs$_2$CO$_3$ (7.4 g) in 32 mL of t-BuOH gave compound (7) (1.6 g).

Example 6: Compound (26) of Table I

According to route (A), a mixture of 2,6-dichloroquinoline (98.5 mg), 6-amino-3-picoline (59.4 mg), Pd(OAc)$_2$ (2.2 mg), XantPhos (5.8 mg) and Cs$_2$CO$_3$ (456 mg) in 2 mL of t-BuOH gave compound (26) (92.3 mg).

Example 7: Compound (38) of Table I

According to route (B), a mixture of 2-aminoquinoline (79.2 mg), 3-bromo-2-methoxypyridine (71.5 mg), Pd(OAc)$_2$ (2.2 mg), XantPhos (5.8 mg) and Cs$_2$CO$_3$ (456 mg) in 2 mL of t-BuOH gave compound (38) (73.5 mg).

Example 8: Compound (31) of Table I

According to route (A), a mixture of 2-chloroquinoline (81.5 mg), 2-amino-3-picoline (55 μL), Pd(OAc)$_2$ (2.2 mg), XantPhos (5.8 mg) and Cs$_2$CO$_3$ (456 mg) in 2 mL of t-BuOH gave compound (31) (87.1 mg).

Example 9: Compound (8) of Table I

According to route (A), a mixture of 2-chloroquinoline (1.1 g), 4-(trifluoromethoxy)aniline (1.0 mL), Pd(OAc)$_2$ (31.4 mg), XantPhos (80.9 mg) and Cs$_2$CO$_3$ (6.4 g) in 28 mL of t-BuOH gave compound (8) (1.3 g).

Example 10: Compound (82) of Table I

According to route (A), a mixture of 2-chloroquinoline (81.5 mg), 2-methyl-4-(trifluoromethoxy)aniline (81 μL), Pd(OAc)$_2$ (2.2 mg), XantPhos (5.8 mg) and Cs$_2$CO$_3$ (456 mg) in 2 mL of t-BuOH gave compound (82) (64 mg).

Example 11: Compound (13) of Table I

According to route (B), a mixture of 3-aminoquinoline (79 mg), 2-bromo-5-methylpyridine (101 mg), Pd(OAc)$_2$ (2.2 mg), XantPhos (5.8 mg) and Cs$_2$CO$_3$ (456 mg) in 2 mL of t-BuOH gave compound (13) (84.4 mg).

Example 12: Compound (105) of Table I

According to route (A), a mixture of 3-bromoquinoline (103.5 mg), 6-amino-3-picoline (59.4 mg), Pd(OAc)$_2$ (2.2 mg), XantPhos (5.8 mg) and Cs$_2$CO$_3$ (456 mg) in 2 mL of t-BuOH gave compound (105) (66.5 mg).

Example 13: Compound (108) of Table I

According to route (B), a mixture of 6-aminoquinoline (79.0 mg), 2-bromo-3methoxypyridine (94.0 mg), Pd(OAc)$_2$ (2.2 mg), XantPhos (5.8 mg) and Cs$_2$CO$_3$ (456 mg) in 2 mL of t-BuOH gave compound (108) (75.9 mg).

Example 14: Compound (16) of Table I

According to route (B), a mixture of 6-aminoquinoline (79.3 mg), 2-bromo-6methylpyridine, Pd(OAc)$_2$ (2.2 mg), XantPhos (5.8 mg) and Cs$_2$CO$_3$ (456 mg) in 2 mL of t-BuOH gave compound (16) (81.2 mg).

Example 15: Compound (113) of Table I

According to route (A), a mixture of 2-chloroquinoline (81.5 mg), aminopyrazine (52.3 mg), Pd(OAc)$_2$ (2.2 mg), XantPhos (5.8 mg) and Cs$_2$CO$_3$ (456 mg) in 2 mL of t-BuOH gave compound (113) (60.7 mg).

Example 16: Compound (123) of Table I

According to route (B), a mixture of 3-bromoquinoline (103.5 mg), p-anisidine (67.7 mg), Pd(OAc)$_2$ (2.2 mg), XantPhos (5.8 mg) and Cs$_2$CO$_3$ (456 mg) in 2 mL of t-BuOH gave compound (386) (65 mg).
$^1$H NMR (300 MHz, CDCl$_3$) δ 8.62 (d, J=2.8, 1H), 7.98 (d, J=7.4, 1H), 7.61-7.54 (m, 1H), 7.45 (ddd, J=1.9, 4.9, 7.1, 3H), 7.18 (d, J=8.9, 2H), 6.94 (d, J=8.9, 2H), 5.86 (s, 1H), 3.84 (s, 3H). $^{13}$C NMR (75 MHz, CDCl$_3$) δ 156.26, 144.27, 143.25, 139.18, 134.42, 129.25, 129.18, 127.24, 126.40, 126.04, 123.03, 115.13, 114.26, 55.79.

Example 17: Compound (128) of Table I

According to route (A), a mixture of 2-chloroquinoline (81.5 mg), 2-aminopyrimidine (52.3 mg), Pd(OAc)$_2$ (2.2 mg), XantPhos (5.8 mg) and Cs$_2$CO$_3$ (456 mg) in 2 mL of t-BuOH gave compound (128) (53.3 mg).

Example 18: Compound (135) of Table I

According to route (A), a mixture of 2-chloroquinoxaline (82.0 mg), 2-aminopyridine (51.7 mg), Pd(OAc)$_2$ (2.2 mg), XantPhos (5.8 mg) and Cs$_2$CO$_3$ (456 mg) in 2 mL of t-BuOH gave compound (135) (47.7 mg).

Example 19: Compound (136) of Table I

According to route (A), a mixture of 2-chloroquinoxaline (82.0 mg), 2-amino-3methylpyridine (59.4 mg), Pd(OAc)$_2$ (2.2 mg), XantPhos (5.8 mg) and Cs$_2$CO$_3$ (456 mg) in 2 mL of t-BuOH gave compound (136) (35.4 mg).

Example 20: Compound (137) of Table I

According to route (A), a mixture of 2-chloroquinoxaline (82.0 mg), 2-amino-5-cyanopyridine (65.4 mg), Pd(OAc)$_2$ (2.2 mg), XantPhos (5.8 mg) and Cs$_2$CO$_3$ (456 mg) in 2 mL of t-BuOH gave compound (137) (79.6 mg).

Example 21: Compound (138) of Table I

According to route (A), a mixture of 2-chloroquinoxaline (82.0 mg), 6-amino-2-picoline (59.4 mg), Pd(OAc)$_2$ (2.2 mg), XantPhos (5.8 mg) and Cs$_2$CO$_3$ (456 mg) in 2 mL of t-BuOH gave compound (138) (89.4 mg).

Example 22: Compound (142) of Table I

According to route (A), a mixture of 2-chloroquinoxaline (82.0 mg), 2-aminopyrimidine (52.3 mg), Pd(OAc)$_2$ (2.2 mg), XantPhos (5.8 mg) and Cs$_2$CO$_3$ (456 mg) in 2 mL of t-BuOH gave compound (142) (47.0 mg).
$^1$H NMR (300 MHz, CDCl3) δ 10.07 (s, 1H), 8.57 (d, J=4.7, 2H), 8.04 (d, J=7.8, 1H), 7.83 (d, J=7.9, 1H), 7.68 (t, J=8.6, 1H), 7.58 (t, J=7.4, 1H), 6.92 (t, J=4.6, 1H).
MS (ESI) [M+H]+=224

Example 23: Compound (146) of Table I

According to route (A), a mixture of 4-methoxy-7-chloro-quinoline* (500.0 mg), 2-amino-4-methylpyridine (0.310 g) XPhos (123.0 mg), K$_2$CO$_3$ (1.41 g) and Pd2dba3 (118.0 mg) in 14 mL of t-BuOH gave compound 146 (500 mg).

Preparation of 4-methoxy-7-chloro-quinoline

Into a 1-Neck round-bottom flask 4,7-dichloro-quinoline, (5.0 g, 0.025 mol) was dissolved in 1.25 M of hydrogen chloride in methanol (16 mL). The mixture was heated to reflux overnight. After 16 hours of heating, the mixture was cooled to room temperature. The mixture was concentrated under reduce pressure. The solid was dissolved in sodium bicarbonate (50 mL, 0.6 mol) (saturated aqueous solution) and the solution was extracted with Ethyl acetate (100 mL, 1 mol) (4×25 ml). The organic layer was washed with sodium chloride (50 mL, 0.8 mol) (saturated aqueous solution) (2×25 ml) and was dried over Na$_2$SO$_4$ and was concentrated under reduce pressure to give 4-methoxy-7-chloro-quinoline (4.5 g pale yellow powder).
MS (ESI) [M+H]+=194

Example 24

Pharmacological Data

The compounds of the invention have been the subject of pharmacological tests which have demonstrated their relevance as active substances in therapy and in particular for preventing, inhibiting or treating pathological or nonpathological conditions linked with premature aging.

The following materials and methods have been used.

Material and Methods

Minigene Constructs Reproduce Aberrant Splicing of LMNA mRNA, Leading to HGPS

Figure 1B:
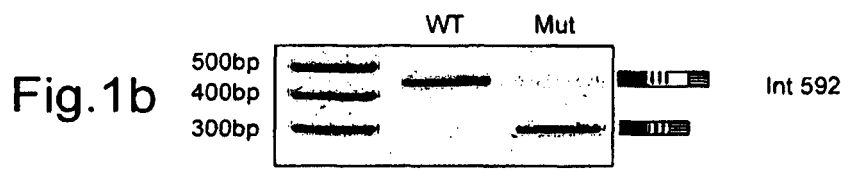
FIG. 1b is an illustration of the results of such experiments (i.e., using this system the splicing event activated by the GGC>GGT mutation in exon 11 of the LMNA gene was confirmed by transfections in cultured HeLa cells (see lanes WT and Mut))
Figure 1C:
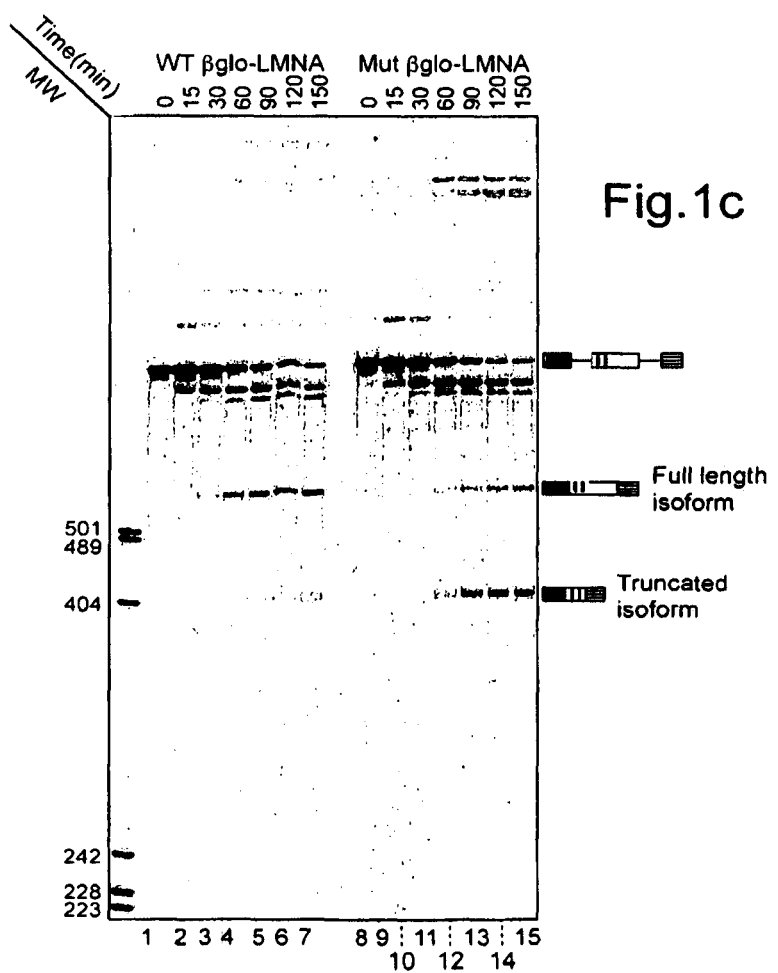
FIG. 1c illustrates the results of transfection experiments of minigene constructs containing or not the point mutation demonstrated that like in Progeria patients the mutation leads to a switch from the use of the normal splice site (intron 11 position 1) to the use of the cryptic splice site upstream of the mutation (exon 11 position 1819).

In order to identify and characterize the factor(s) involved in the use of the cryptic 5' splice site in exon 11 of LMNA, an ex vivo system has been developed that recapitulates this splicing event. The cloning of mutant and wild type constructs (FIG. 1A, for schematic representation) were carried out using a TOPO-TA cloning vector in which is inserted a minigene containing 142 nts of β-Globin first exon, 130 nts β-Globin first intron, 270 nts LMNA exon 11 either wild type or mutant, 322 nts intron 11 and 46 nts exon 12. Using this system the splicing event activated by the GGC>GGT mutation in exon 11 of the LMNA gene was confirmed by transfections in cultured HeLa cells (FIG. 1B, lanes WT and Mut) as well as in vitro splicing experiments using in vitro synthesized radiolabeled substrate (Panel C). Transfection experiments of minigene constructs containing or not the point mutation demonstrated that like in Progeria patients the mutation leads to a switch from the use of the normal splice site (intron 11 position 1) to the use of the cryptic splice site upstream of the mutation (exon 11 position 1819) (FIG. 1, Panel C, compare lanes WT and Mut). Note that following a kinetics of in vitro splicing for 150 minutes, aberrant splicing is observed with the wild type substrate (FIG. 1C, Lanes 1-7), implying that the mutation is not a perquisite for cryptic splice site usage. The mutation simply enhances the efficacy of selection of this cryptic splice site (FIG. 1C, Lanes 8-15).

Figure 2A:
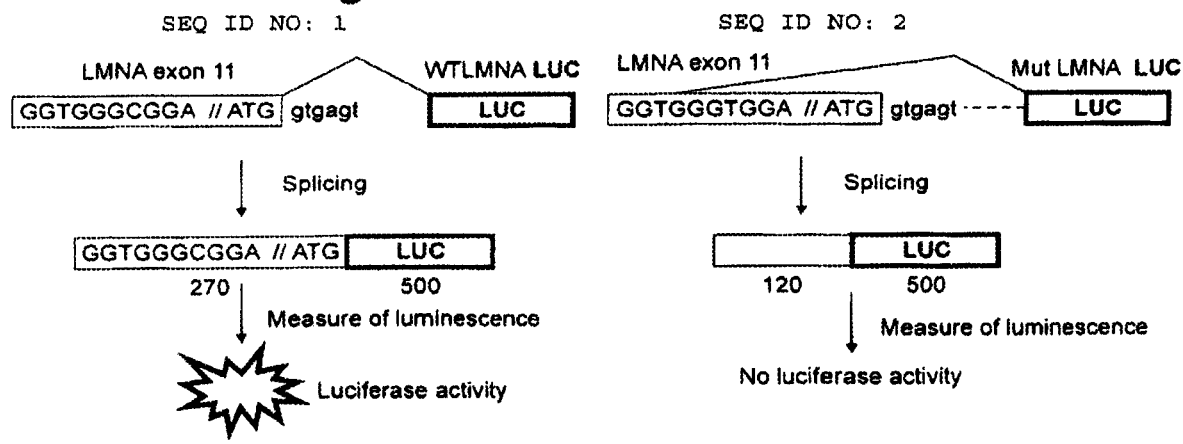
FIG. 2a is schematic representation of the construction of a plasmid in which exon 11, intron 11 and part of exon 12 of LMNA gene were fused with luciferase cDNA.
Figure 2B:
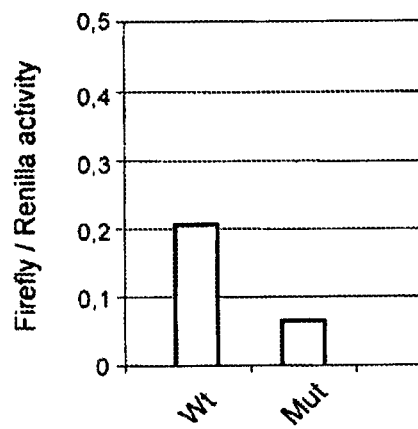
FIG. 2b is an illustration of the results of Luciferase assays.
Figure 2C:
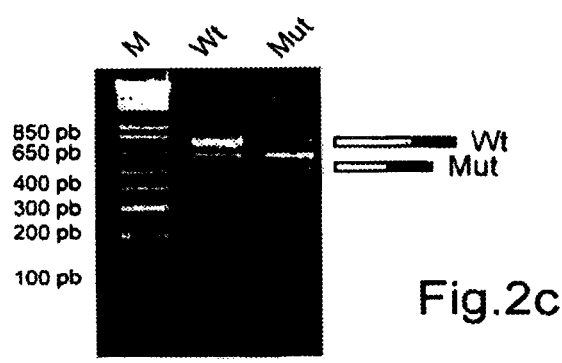
FIG. 2c is an illustration of the results of RT-PCR.

Advantage has been taken of the luciferase system. The luciferase assay is an extremely sensitive and rapid assay. Linear results are seen over at least eight orders of magnitude of enzyme concentration. Moreover, the luciferase assay is well suited for high-throughput applications. To conduct a Mid-throughput screening (MTS) for compounds repressing LMNA aberrant splicing, we have constructed a plasmid in which exon 11, intron 11 and part of exon 12 of LMNA gene were fused with luciferase cDNA (FIG. 2). Both wild type (WtLMNA-luc)(SEQ ID NO: 1) and mutant (MutLMNA-luc)(SEQ ID NO: 2) substrate harbouring exon 11 mutation have been constructed. In these constructs we have generated a single initiation codon in exon 11 such as correct splicing will lead to luciferase expression, while aberrant splicing will skip the initiation codon and thereby prevent luciferase expression. After transfection in HeLa cells, Luciferase assays (FIG. 2B) and RT-PCR (FIG. 2C) indicate that WtLMNA-luc produces predominantly wild type splicing and large amount of luciferase activity, whereas MutLMNA-luc recapitulate the aberrant splicing profile with reduced luciferase expression (FIGS. 2B and C, compare Wt and Mut). In order to use this system in MTS, we have generated a stable 293 cell lines containing a single integrated copy of luciferase reporter containing LMNA mutation (MutLMNA-luc cell line) using the flp system from INVITROGEN. This system allows us to perform a MTS for compounds able to enhance luciferase activity.

Plasmids Constructs.

LMNA sequences (1278 bp of exon 11, intron 11 and 46 bp of exon 11) were PCR-amplified from either control or patient's cells genomic DNA with specific primer PCR fragments were purified with Concert Rapid PCR purification system (Invitrogen) and subcloned at the BamHI and EcoRI restriction sites of the pSpβm3S1 plasmid containing the βGlobin cassette (Labourier et al., 1999—Recognition of exonic splicing enhancer sequences by the Drosophila splicing repressor RSF1. Nucleic Acids Res. 27, 2377-2386) to give the βGlo3S1LMNAwt and βGlo3S1LMNAmut constructs. The chimeric βGlo-LMNA sequences were then inserted into the pcDNA3.1D/V5-His-TOPO vector (Invitrogen) to be used in transfection and in vitro splicing experiments. A single initiation codon ATG was kept in exon 11 of LMNA and LMNA sequences described above were fused at their 3' end to Fyrefly luciferase cDNA (LM-NAlucWT) in order that removal of intron 11 generates a transcript that encode a fusion protein harbouring luciferase activity, whereas usage of the cryptic splice site of mutated exon 11 (LMNAlucMut) will remove the initiation codon preventing luciferase expression. Both sequences were cloned in pcDNA3 Flp-In vector (Invitrogen).

Transfection and RT-PCR.

HeLa cells transfections with splicing reporter constructs were performed with lipofectAMINE 2000 reagent (Invitrogen) according to the manufacturer's instructions. Twenty four hours after transfection, total RNA was purified with RNA-PLUS™ (Quantum Bioprobe). First strand cDNA was synthesized from 2 µg of RNA with the Amersham-Pharmacia First strand cDNA synthesis kit. For PCR analyses, 1/15 of the reaction was amplified with Taq polymerase (Invitrogen). The cycle number was kept to a minimum to maintain linearity. PCR products were separated on a 1.5% agarose gel containing ethidium bromide and visualized under UV light.

A stable 293 cell line containing a single copy of LMNAlucMut minigene was obtained using the Flp-In system from (Invitrogen) according to manufacture procedure. Several clones were obtained and only one clone was used to screen the whole chemical library (293FLP LMNA LUC cells #8).

Nuclear Extracts Preparation, Splicing and Complementation Assays.

HeLa cells nuclear extracts were prepared according to (Dignam et al., 1983—Eukaryotic gene transcription with purified components. Methods Enzymol. 101, 582-598). Pre-mRNA were synthesized by in vitro transcription in the presence of 20 units of T7 RNA polymerase, 1 µg of the suitable linearized plasmids and 5 µM [α-$^{32}$P] UTP (3000 Ci/mmol) in 25 µl reactions according to manufacturer conditions. In vitro transcripts were quantified by Cerenkov counting. Splicing reactions were performed under standard conditions as described previously (Tazi et al., 1986—A protein that specifically recognizes the 3' splice site of mammalian pre-mRNA introns is associated with a small nuclear ribonucleoprotein. Cell 47, 755-766). Splicing products were analyzed by electrophoresis on 7% denaturing polyacrylamide gels and revealed by autoradiography.

Material

293FLP LMNA LUC cells #8

Hygromycin B at 50 mg/mL (invitrogen 10687-010)

Dulbecco's Modified Eagle Medium (D-MEM) (1×)+ GlutaMAX, liquid (invitrogen 31966-021)

Dulbecco's Phosphate Buffered Saline (D-PBS) (1×), liquid (invitrogen 14190-169)

Trypsin 2.5%

Foetal calf serum (FCS)

Penicillin (P)

Streptomycin (S)

Passive Lysis Buffer (PLB) (5×) (Promega)

Bradford Reagent (B6916)

Luciferase assay buffer

96 Well Plate sterile, V-shape (greiner bio-one 651180)

96 Well Microplate sterile, flat bottom (greiner bio-one 655180)

96 Well Microplate, flat bottom, Chimney Well (greiner bio-one 655075)

CellTiter 96® AQueous One Solution (Promega G3581)

Methods

First Day

Plate at 500 µM

In a 96 Well Plate sterile, V-shape one put 0.5 µl of drug compounds at 50 mM and then add 49.5 µl of 10% DMSO.

Replica Plate

One pipets 47 µl of drug at 500 µM and adds 200 µL of DMEM+Hygromycin B. At this stage the concentration of drug compound is 10 µM. One shares out 100 µl in a 96 Well Microplate sterile, flat bottom (further called luciferase plate) and 50 µl in other one (further called toxicity plate).

One washes 293FLP LMNA LUC cells once with D-PBS then adds 1 ml trypsin EDTA. Incubation at 37° C. for 2-3 minutes is proceeded. Then one adds 9 ml DMEM (with 10% FCS, P/S).

One takes 7 µl of cell suspension and adds 14 µL blue trypan to count cells. Meanwhile cell suspension is centrifugated at 1200 rpm for 5 minutes at room temperature (RT).

Cell concentration is brought at 105 cells per ml with DMEM+Hygromycin B to have 104 cells per 100 µl.

Luciferase Plate

100 µl of suspension cells is added (at 104 cells per 100 µl) so final concentration of compounds is 5 µM.

Toxicity Plate

50 µl of suspension cells is added. The final concentration of compounds is 5 µM.

48 Hours Later

Toxicity Plate

20 µl of CellTiter 96® AQueous One Solution is added per well. Incubation is proceeded at 37° C. for 2 h. Absorbance is red at 490 nm.

Luciferase Plate

Medium of the wells is gently removed then washed once by adding slowly 150 µl of D-PBS 1×. D-PBS is removed. 40 µl of PLB 1× is added and incubated at RT for 30 minutes.

20 µl of cell lysate is put in a 96 Well Microplate, flat bottom, Chimney Well. 70 µl of luciferin assay substrate is added. One read luminescence for 1 second.

200 µl of Bradford reagent is added on the remaining cell lysate (20 µl). Incubation is proceeded at RT for 30 min then one can read absorbance at 595 nm. A range has to be made. Usually 5 different concentrations are tested: 0.25, 0.5, 0.75, 1 and 1.25 mg/ml.

Results

The compounds according to the present invention demonstrate an increase of luciferase activity ranging between 3 and 7 fold compared to control untreated MutLMNA-luc cell line.

In particular, the results are as follows for some of the compounds according to the present invention.

| Compound number | Increase of luciferase activity |
| --- | --- |
| 7 | 3.33 |
| 34 | 4.18 |
| 36 | 3.06 |
| 31 | 5.07 |
| 26 | 6.20 |
| 8 | 3.35 |
| 105 | 3.25 |
| 135 | 4.58 |
| 136 | 5.20 |
| 137 | 4.64 |
| 138 | 8.22 |
| 142 | 4.47 |
| 2 | 3.77 |
| 3 | 4.54 |
| 4 | 4.43 |
| 5 | 2.02 |
| 17 | 3.66 |
| 18 | 2.85 |
| 25 | 3.49 |
| 28 | 2.99 |
| 32 | 2.96 |
| 33 | 2.14 |
| 35 | 2.74 |
| 38 | 5.81 |
| 39 | 4.29 |
| 41 | 3.32 |
| 42 | 3.87 |
| 45 | 3.08 |
| 59 | 2.49 |
| 61 | 2.04 |
| 82 | 3.41 |
| 83 | 2.74 |
| 86 | 2.77 |
| 102 | 2.06 |
| 9 | 2.47 |
| 10 | 2.01 |
| 13 | 3.46 |
| 106 | 2.77 |
| 15 | 2.17 |
| 16 | 4.56 |
| 107 | 2.20 |
| 108 | 4.57 |
| 109 | 2.79 |
| 113 | 2.28 |
| 120 | 2.38 |
| 123 | 2.94 |
| 125 | 2.59 |
| 128 | 3.08 |
| 145 | 3.87 |
| 146 | 4.18 |
| 147 | 2.94 |

Therefore, the result of the tests carried out on the compounds disclosed in the present invention show that said compounds may be useful to inhibit, prevent and/or treat diseases with premature aging and that are likely related to an aberrant splicing of the nuclear lamin A gene. Among all, said disease may include Hutchinson Guilford Progeria Syndrome (HGPS), progeria, premature aging associated with HIV infection, muscular dystrophy, Charcot-Marie-Tooth disorder, Werner syndrome, but also atherosclerosis, insulin resistant type II diabetes, cataracts, osteoporosis and aging of the skin such as restrictive dermopathy.

For this purpose an effective amount of a said compound may be administered to a patient suffering from premature aging and in particular from progeria, and from the previous cited diseases.

The present invention is also related to the use of at least a compound chosen among a compound of anyone of formula (I), (I'), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for the manufacture of a pharmaceutical composition intended for the treatment of pathological or nonpathological conditions linked with premature aging and in particular progeria.

The present invention also encompasses pharmaceutical compositions comprising at least a compound chosen among new compounds of formula (Ia), (Ia'), (Ic), (Id), (Ii'), (Ij'), (Ij''), (Ij'''), (Ik), (Io), (Ip) and (Ir) as defined above and compounds (1), (2), (5)-(7), (10)-(16), (18), (21)-(44), (46)-(74), (105)-(108), (124)-(130), (135)-(141), (145)-(147), (150)-(154), (159), (160)-(165), (168), as defined above or any pharmaceutically acceptable salt thereof.

Thus, these pharmaceutical compositions contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

The present invention is also related to the use of at least a compound chosen among a compound of anyone of formula (I), (I'), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for the manufacture of a pharmaceutical composition intended for inhibiting, preventing and/or treating pathological or nonpathological conditions linked with premature aging and in particular progeria but also all the previous listed diseases.

The present invention further relates to a method of treatment of patients suffering form premature aging or anyone of the previous listed disease, which comprises at least a step of administration to a patient suffering thereof of an effective amount of a compound of anyone of formula (I), (I'), (Ia), (Ib), (Ic), (Id), (Ie), (If), (Ig), (Ih), (Ti), (Ij), (Ik), (Il), (Im), (Io), (Ip), (Iq), (Ir), (Iee) and (1) to (168) or one of its pharmaceutically acceptable salts.

What is claimed is:

1. A compound, or a pharmaceutically acceptable salt thereof, selected from the group consisting of:

a compound of formula (Ig):

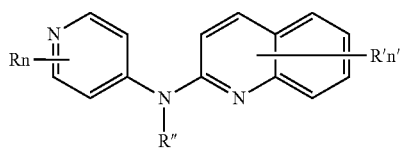

(Ig)

wherein:
- R independently represents a hydrogen atom, a halogen atom, a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, or a $(C_1-C_3)$alkoxy group,
- n is 1 or 2,
- n' is 1 or 2,
- R' is a hydrogen atom, a $(C_1-C_3)$alkyl group, a halogen atom, a —NO$_2$ group, a —COOR$_1$ group, a —NR$_1$R$_2$ group, a —CN group, or a $(C_1-C_3)$alkoxy group,
- R" is a hydrogen atom or a $(C_1-C_4)$alkyl group,
- R$_1$ and R$_2$ are independently a hydrogen atom or a $(C_1-C_3)$alkyl group,
- R and R' are not simultaneously a hydrogen atom, and when n and n' are each 1 and R is a hydrogen atom, then R' is not a —COOH group;

a compound of formula (Ii'):

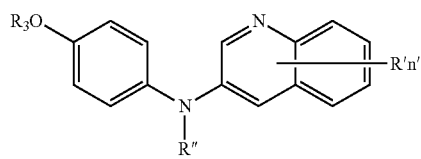

(Ii')

wherein:
- R$_3$ is a $(C_1-C_3)$fluoroalkyl group or a $(C_1-C_3)$alkyl group,
- R' is a hydrogen atom, a halogen atom, a $(C_1-C_3)$alkyl group, a —COOR$_1$ group, a —NO$_2$ group, a —NR$_1$R$_2$ group, a $(C_1-C_3)$alkoxy group, or a —CN group,
- R$_1$ and R$_2$ are independently a hydrogen atom or a $(C_1-C_3)$alkyl group,
- R" is a hydrogen atom or a $(C_1-C_4)$alkyl group, and
- n' is 1 or 2
- with the proviso that when R' is a hydrogen atom, R$_3$ is not a methyl group or a trifluoromethyl group;

a compound of formula (Ik):

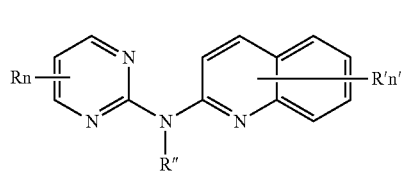

(Ik)

wherein:
- R independently represents a hydrogen atom, a halogen atom, a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, or a $(C_1-C_3)$alkoxy,
- R$_1$ and R$_2$ are independently a hydrogen atom or a $(C_1-C_3)$alkyl group,
- n is 1 or 2,
- n' is 1 or 2,
- R" is a hydrogen atom or a $(C_1-C_4)$alkyl group, and
- R' is a hydrogen atom, a halogen atom, a $(C_1-C_3)$alkyl group, a —COOR$_1$ group, a —NO$_2$ group, a —NR$_1$R$_2$ group, a $(C_1-C_3)$alkoxy group and a —CN group; and a compound of formula (Ip):

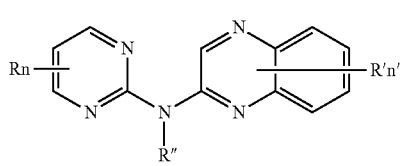

wherein:
R independently represents a hydrogen atom, a halogen atom, a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, or a ($C_1$-$C_3$)alkoxy group, R$_1$ and R$_2$ are independently a hydrogen atom or a ($C_1$-$C_3$)alkyl group, R" is a hydrogen atom or a ($C_1$-$C_4$)alkyl group, n' is 1 or 2, n is 1 or 2, and R' is a hydrogen atom, a halogen atom, a ($C_1$-$C_3$)alkyl group, a —COOR$_1$ group, a —NO$_2$ group, a —NR$_1$R$_2$ group, a ($C_1$-$C_3$)alkoxy group, or a —CN group, with the proviso that:

R and R' are not simultaneously a hydrogen atom, and when n and n' are 2 then R and R' are not simultaneously a methyl group.

2. The compound, or a pharmaceutically acceptable salt thereof, of claim 1, wherein the compound is a compound of the formula (Ig):

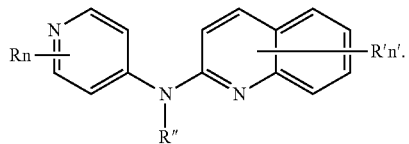

3. The compound, or a pharmaceutically acceptable salt thereof, of claim 1, wherein the compound is a compound of the formula (Ii'):

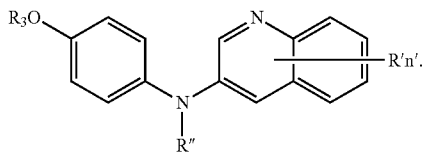

4. The compound, or a pharmaceutically acceptable salt thereof, of claim 1, wherein the compound is a compound of the formula (Ik):

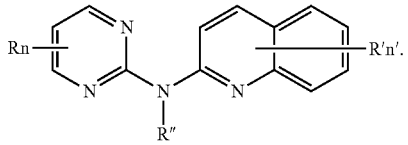

5. The compound, or a pharmaceutically acceptable salt thereof, of claim 1, wherein the compound is a compound of the formula (Ip):

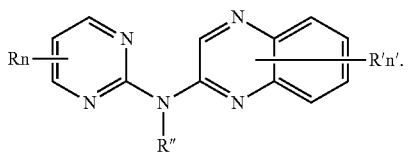

6. The compound of claim 1, wherein the pharmaceutically acceptable salt is selected from the group consisting of a hydrochloride salt, a hydrobromide salt, a tartrate salt, a fumarate salt, a citrate salt, a trifluoroacetate salt, an ascorbate salt, a triflate salt, a mesylate salt, a tosylate salt, a formate salt, an acetate salt, and a malate salt.

7. A pharmaceutical composition comprising at least one compound, or a pharmaceutically acceptable salt thereof, of claim 1 and a pharmaceutically acceptable carrier.

8. A compound, or a pharmaceutically acceptable salt thereof, selected from the group consisting of:

(119) 8-chloro-N-(pyridin-4-yl)quinolin-2-amine (128) N-(pyrimidin-2-yl)quinolin-2-amine (129) 8-chloro-N-(pyrimidin-2-yl)quinolin-2-amine, and (130) 4-methyl-N-(pyrimidin-2-yl)quinolin-2-amine.

9. The compound of claim 8, wherein the pharmaceutically acceptable salt is selected from the group consisting of a hydrochloride salt, a hydrobromide salt, a tartrate salt, a fumarate salt, a citrate salt, a trifluoroacetate salt, an ascorbate salt, a triflate salt, a mesylate salt, a tosylate salt, a formate salt, an acetate salt, and a malate salt.

10. A pharmaceutical composition comprising at least one compound, or a pharmaceutically acceptable salt thereof, of claim 8 and a pharmaceutically acceptable carrier.

* * * * *

SEQUENCE LISTING

```
<160> NUMBER OF SEQ ID NOS: 8

<210> SEQ ID NO 1
<211> LENGTH: 847
<212> TYPE: DNA
<213> ORGANISM: Mus musculus
<220> FEATURE:
<221> NAME/KEY: misc_feature
<223> OTHER INFORMATION: G0S2

<400> SEQUENCE: 1
tgcagtcagg gctcaggcca gtgagccagg aggcggatcc cggacaaaag atataaggac    60
tctgttcaca gagcgctgca gctgcggagt gtccctccca aagagcagca gctgagggaa   120
gaagaacgcc aaagccagtc tgacgcaagg acgcctgacc ttctccagca agtgctgcct   180
ctcttcccac tgcaccctag gcccagccac ccacagccca gagctcagat ggaaagtgtg   240
caggagctga tccctctggc caaggagatg atggcgcaga agccccgagg gaagctagtg   300
aagctatacg tgctgggcag tgtgctggcg ctcttcggtg tggtgctcgg cctagttgag   360
acggtgtgca gcccttttcac agccgccagc cgtctgcgcg accaagaggc tgcagtggtg   420
gagctgcggg aagcgtgtga acagcagtcc ctccacaagc aggccctgct ggcaggaggc   480
aaggcacagg aggcgaccct gtgcagccgg gccctgtccc tccggcagca cgcctcttaa   540
ggccggtgac tgacagagaa gggagacaca gatcatgacc caggtgggca acagagtcac   600
atgctgtttc aaggtgccac cgaatccaga actgacccca cacagatcac ctaagggtc    660 tgggactgat ttgctgctgt gcagcacgca ctgtgatttg ccctaggctg tgcgagcaat   720
caaggagcta tcactttgca ttagagaagg agacaggctt tttatacagt tatttttatt   780
gttattatta ttattgcaat gactatcgtt ttgcattttg aaataaaaac cttttatact   840
ctaaaaa                                                              847

<210> SEQ ID NO 2
<211> LENGTH: 978
<212> TYPE: DNA
<213> ORGANISM: Homo sapiens
<220> FEATURE:
<221> NAME/KEY: misc_feature
<223> OTHER INFORMATION: G0S2

<400> SEQUENCE: 2
tggctctgac cgcgctggcc tgggccggag agcccaggag gcgtgtctca gagaaaagat    60
ataagcggcc cccggacgct aaagcggtgc cagcggcgga gtctccaact gggagagctg   120
cagctgccga gaggaggaga acgctgaggt cggtcggacc aacggacgcg ctgaccgctg   180
```

-continued

| | |
|---|---|
| ccaactgcag ctcgcgctgc ctcctgctcg cgccgtgcca ctaaggtcat tcccgcctcc | 240 |
| gagagcccag agccgagatg gaaacggtcc aggagctgat ccccctggcc aaggagatga | 300 |
| tggcccagaa gcgcaagggg aagatggtga agctgtacgt gctgggcagc gtgctggccc | 360 |
| tcttcggcgt ggtgctcggc ctgatggaga ctgtgtgcag ccccttcacg gccgccagac | 420 |
| gtctgcggga ccaggaggca gccgtggcgg agctgcaggc cgccctggag cgacaggctc | 480 |
| tccagaagca agccctgcag gagaaaggca agcagcagga cacggtcctc ggcggccggg | 540 |
| ccctgtccaa ccggcagcac gcctcctagg aactgtggga gaccagcgga gtgggaggga | 600 |
| gacgcagtag acagagacag accgagagag gaatggagag acagaggggg cgcgcgcaca | 660 |
| ggagcctgac tccgctggga gagtgcagga gcacgtgctg tttttattt ggacttaact | 720 |
| tcagagaaac cgctgacatc tagaactgac ctaccacaag catccaccaa aggagtttgg | 780 |
| gattgagttt tgctgctgtg cagcactgca ttgtcatgac atttccaaca ctgtgtgaat | 840 |
| tatctaaatg cgtctaccat tttgcactag ggaggaagga taaatgcttt ttatgttatt | 900 |
| attattaatt attacaatga ccaccatttt gcatttgaa ataaaaaaac tttttatacc | 960 |
| ataaaaaaaa aaaaaaaa | 978 |

<210> SEQ ID NO 3
<211> LENGTH: 25
<212> TYPE: RNA
<213> ORGANISM: Artificial Sequence
<220> FEATURE:
<223> OTHER INFORMATION: siRNA anti-sense strand against G0S2

<400> SEQUENCE: 3
aaagggcugc acaccgucuc aacua           25

<210> SEQ ID NO 4
<211> LENGTH: 25
<212> TYPE: RNA
<213> ORGANISM: Artificial Sequence
<220> FEATURE:
<223> OTHER INFORMATION: control siRNA anti-sense strand

<400> SEQUENCE: 4
cguuggaauc gaguauuccu gggaa           25

<210> SEQ ID NO 5
<211> LENGTH: 64
<212> TYPE: DNA
<213> ORGANISM: Artificial Sequence
<220> FEATURE:
<223> OTHER INFORMATION: DNA fragment for expressing miRNA against G0S2

<400> SEQUENCE: 5
tgctgttcgg tggcaccttg aaacaggttt tggccactga ctgacctgtt tcagtgccac    60
cgaa    64

<210> SEQ ID NO 6
<211> LENGTH: 64
<212> TYPE: DNA
<213> ORGANISM: Artificial Sequence
<220> FEATURE:
<223> OTHER INFORMATION: DNA fragment for expressing miRNA against G0S2

<400> SEQUENCE: 6
cctgttcggt ggcactgaaa caggtcagtc agtggccaaa acctgtttca aggtgccacc    60
gaac    64

```
<210> SEQ ID NO 7
<211> LENGTH: 25
<212> TYPE: RNA
<213> ORGANISM: Artificial Sequence
<220> FEATURE:
<223> OTHER INFORMATION: siRNA sense strand against Hsd17b4

<400> SEQUENCE: 7
gagcauuagu cauugugaac gacuu                                    25

<210> SEQ ID NO 8
<211> LENGTH: 25
<212> TYPE: RNA
<213> ORGANISM: Artificial Sequence
<220> FEATURE:
<223> OTHER INFORMATION: siRNA anti-sense strand against Hsd17b4

<400> SEQUENCE: 8
aagucguuca caaugacuaa ugcuc                                    25
```